United States Patent [19]
Narumiya et al.

[11] Patent Number: 6,111,072
[45] Date of Patent: Aug. 29, 2000

[54] RHO TARGET PROTEIN HUMAN MDIA AND GENE ENCODING SAME

[75] Inventors: Shuh Narumiya, Kyoto; Nobuaki Takahashi, Yokohama, both of Japan

[73] Assignee: Kirin Beer Kabushiki Kaisha, Tokyo-to, Japan

[21] Appl. No.: 08/899,595

[22] Filed: Jul. 24, 1997

[30] Foreign Application Priority Data

Aug. 26, 1996 [JP] Japan .................................. 9-242701
Mar. 25, 1997 [JP] Japan .................................. 9-090170

[51] Int. Cl.[7] .................................................. C07K 1/00
[52] U.S. Cl. ........................................................ 530/350
[58] Field of Search ........................... 530/350; 536/23.1; 435/69.1, 252.3, 320.1, 7.1

[56] References Cited

PUBLICATIONS

Creighton. Proteins: Structures and molecular properties. WH Freeman and Company, New York. pp. 23–28, 1993.
Entrez Protein Query. ORF YNL271c. EMBL Accession No. Z71547, Apr. 29, 1996.
Wasserman, S. FH proteins as cytoskeletal organizers. Trends Cell Biol. 8(3):111–115, 1998.
Ishizaki et al, "The small GTP–binding protein Rho binds to and activates a 160 kDa Ser/Thr protein kinase homologous to myotonic dystrophy kinase", *The EMBO Journal vol. 15 No. 8* pp 1885–1893 (1996).

H. Qadota et al., "Identification of Yeast Rho1p GTPase as a Regulatory Subunit of 1,3–β–Glucan Synthase", Science, vol. 272, Apr. 12, 1996, p. 279–281.
J. Drgonova et al., "Rho1p, a Yeast Protein at the Interface Between Cell Polarization and Morphogenesis", Science, vol. 272, Apr. 12, 1996, p. 277–278.
H. Nonaka et al., "A Downstream Target of RHO1 Small GTP–binding Protein is PKC1, a Homolog of Protein Kinase C, Which Leasds to Activation of the MAP Kinase Cascade in *Saccharomyces cerevisiae*", The EMBO Journal, vol. 14, No. 23, 1995, pp. 5931–5938.

(List continued on next page.)

*Primary Examiner*—Karen Cochrane Carlson
*Assistant Examiner*—Devesh Srivastava
*Attorney, Agent, or Firm*—Foley & Lardner

[57] ABSTRACT

An objective of the present invention is to provide an activated Rho protein target protein derived from a human and a gene coding for the same. The present invention provides a protein derived from a human and a derivative thereof which has the following characteristics: (1) having activated Rho protein binding activity, (2) having profilin binding activity, (3) the gene coding for the protein being located at q31.2 of chromosome 5, and (4) having a molecular weight of about 150 kDa as measured by SDS-PAGE. Respiratory tract hypersensitivity, bronchial asthma, acute myelocytic leukemia (AML) and myelodysplasia syndrome (MDS) can be diagnosed using the nucleotide sequence coding for this protein.

3 Claims, 21 Drawing Sheets

OTHER PUBLICATIONS

Naoki Watanabe et al., "p140mDia, a mammalian homolog of *Drosophila diaphanous,* is a target protein for Rho small GTPase and is a ligand for profilin", The EMBO Journal, vol. 16, No. 11, 1997, pp. 3044–3056.

K. Kimura et al., Regulation of Myosin Phosphatase by Rho and Rho–Associated Kinase (Rho–Kinase), Science, vol. 273, Jul. 12, 1996, pp. 245–248.

T. Reid et al., "Rhotekin, a New Putative Target for Rho Bearing Homology to a Serine/Threonine Kinase, PKN, and Rhophilin in the Rho–binding Domain", The J. of Biological Chemistry, vol. 271, No. 23, 1996, pp. 13556–13560.

T. Matsui et al., "Rho–associated kinase, a novel serine/threonine kinase, as a putative target for the small GTP protein Rho", The EMBO Journal, vol. 15, No. 9, 1996, pp. 2208–2216.

T. Leung et al., "A Novem Serine/Threonine Kinase Binding the Ras–related RhoA GTPase which Translocates Kinase to Peripheral Membranes", J. of Biol. Chem., vol. 270, No. 49, 1995, pp 29051–19054.

P. Madaule et al., "A novel partner for the GTP–bound forms of rho and rac", FEBS Letters 337:1995 pp. 243–248.

G. Watanabe et al., "Protein Kinase N (PKN) and PKN–Related Protein Rhophilin as Targets of Small GTPase Rho", Science, vol. 271, Feb. 1996, pp. 645–650.

T. Nishiyama et al., "Regulation of cytoskeleton by Rho", Experimental Medicine, vol. 12, No. 8, 1994, pp. 991–996.

H. Kohno et al., "Bni1p implicated in cytoskeletal control is a putative target of Rho1p small GTP binding in *Saccharomyces cerevisiae*", The EMBO Journal, vol. 15, No. 22, 1996, pp. 6060–6068.

D. Castrillon et al., "diaphanous is required for cytokinesis in Drosophila and shares domains of similarity with the products of the limb deformity gent", Development 120, 1994, pp. 3367–3377.

S. Emmons et al., "cappuccino, a Drosophila material effect gene required for polarity of the egg and embryo, is related to the vertebrate limb deformity locus", Genes & Development, 9:2482–2494, 1995.

R. Woychik et al., "'Formins': proteins deduced from the alternative transcripts of the limb deformity gene", Nature, vol. 346, Aug. 1990, pp. 850–853.

K. Hirata et al., "Involvement of rho p21 in the GTP–enhanced Calcium Ion Sensitivity of Smooth Muscle Contraction", J. Biol. Chem., vol. 267, No. 13, 1992, pp. 8719–8722.

M. Amano et al., "Phosphorylation and Activation of Myosin by Rho–associated Kinase (Rho–kinase)", J. Biol. Chem., vol. 271, No. 34, 1996, pp. 20246–20249.

T. Leung et al., "The p160 RhoA–Binding Kinase ROKα is a Member of a Kinase Family and is Involved in the Reorganization of the Cytoskeleton", Molecular and Cellular Biology, vol. 16, No. 10, 1996, pp. 5313–5327.

O. Nakagawa et al., "ROCK–I and ROCK–II, Two Isoforms of Rho–associated Coil–coil Forming Protein Serine/Threonine Kinase in Mice", FEBS Letters 392(1996), pp. 189–193.

M. Amano et al., "Formation of Actin Stress Fibers and Focal Adhesions Enhanced by Rho–Kinase", Science, vol. 275, Feb. 1997, pp. 1308–1311.

A. Ridley et al., "The Small GTP–binding Protein rho Regulates the Assembly of Focal Adhesions and Actin Fibers in Response to Growth Factors", Cell, vol. 70, Aug. 1992, pp. 389–399.

A. Ridley et al., "Signal Transduction Pathways Regulating Rho–mediated Stress Fibre Formation: requirement tyrosine kinase", The EMBO Journal, vol. 13, No. 11, 1994, pp. 2600–2610.

H. Paterson et al., "Microinjection of Recombinant $p21^{rho}$ Induces Rapid Changes in Cell Morphology", J. of Cell Biology, vol. 111, 1990, pp. 1001–1007.

N. Morii et al., "A rho Gene Product in Human Blood Platelets", J. of Biol. Chem., vol. 267, No. 29, Oct. 1992, pp. 20921–20926.

T. Tominaga et al., "Inhibition of PMA–induced, LFA–1–dependent Lymphocyte Aggregation of ADP Ribosylation the Small Molecular Weight GTP Binding Protein, rho", J. of Cell Biology, vol. 120, No. 6, 1993, pp. 1529–1537.

A. Nusrat et al., "Rho protein regulates tight junctions and perijunctional actin organization in polarized epithelia", Pro. Natl. Acad. Sci. USA, vol. 92, 1996, pp. 10629–10633.

C. Laudanna et al., "Role of Rho in Chemoattractant–Activated Leukocyte Adhesion Through Integrins", vol. 271, Feb. 1996, pp. 981–983.

K. Takaishi et al., "Involvement of Rho p21 small GTP–binding protein and its regulator in the HGF–induced cell motility", Oncogene (1994) 9:273–279.

K. Kishi et al., "Regulation of Cytoplasmic Division of Xenopus Embryo by rho p21 and its Inhibitory GDP/GTP Exchange Protein (rho GDI)", J. of Cell Biology, vol. 120, No. 5, 1993, pp. 1187–1195.

I. Mabuchi et al., "a rho–like protein is involved in the organisation of the contractile ring in dividing sand dollar eggs", Zygote 1, Nov. 1993, pp. 325–331.

G. Prendergast et al., "Critical role of Rho in cell transformation by oncogenic Ras", Oncogene, 1995, 10:2289–2296.

R. Khosravi–far et al., "Activation of Rac1, RhoA, and Mitogen–Activated Protein Kinases is Required for Ras Transformation", Molecular and Cellular Biology, vol. 15, No. 11, Nov. 1995, pp. 6443–6453.

P. Lebowitz et al., "Evidence that Farnesyltransferase Inhibitors Suppress Ras Transformation by Interfering with Rho Activity", Molecular and Cellular Biology, vol. 15, No. 12, 1995, pp. 6613–6622.

R. Qiu et al., "A Role for Rho in Ras Transformation", Proc. Natl. Acad. Sci. USA, vol. 92, Dec. 1995, pp. 11781–11785.

N. Lamarche et al., "GAPs for rho–related GTPases", Reviews, TIG Dec. 1994, vol. 10, No. 12, pp. 436–440.

M. Noda et al., "Involvement of rho GTPγS–induced enhancement of phosphorylation of 20 kDa mysoin light in vascular smooth muscel cells: inhibition of phosphatase activity", FEBS Letters 367, 1995, pp. 246–250.

M. Gong et al., "Role of guanine nucleotide–binding proteins—ras–family or trimeric proteins or both—in $Ca_{2+}$ sensitization of smooth muscle", Proc. Natl. Acad. Sci. USA, vol. 93, Feb. 1996, pp. 1340–1345.

J. Zhang et al., "Activation of Platelet Phosphatidylinositide 3–Kinase Requires the Small GTP–binding Protein Rho", J. of Biological Chemistry, vol. 268, No. 30, 1993, pp. 22251–22254.

L. Chong et al., "The Small GTP–binding Protein Rho Regulates a Phosphatidylinositol 4–Phosphate 5–Kinase in Mammalian Cells", Cell, vol. 79, Nov. 1994, pp. 507–513.

C. Hill et al., The Rho Family GTPases RhoA, Rac1, and CDC42Hs Regulate Transcriptional Activation by Cell, vol. 81, Jun. 1995, pp. 1159–1170.

J. Collard, "Signaling pathways regulated by Rho–like proteins: A possible role in tumor formation and metastasis (Review)", International J. of Oncology, 8: 0–00, 1996, pp. 1–8.

M. Hart et al., Cellular Transformation and Guanine Nucleotide Exchange Activity are Catalyzed by a Common Domain on the dbl Oncogene Product, J. of Biological Chemistry, vol. 269, No. 1, 1994, pp. 62–65.

Y. Horii et al., "A novel oncogene, ost, encodes a guanine nucleotide exchange factor that potentially links Rho and Rac signaling pathways", EMBO Journal, vol. 13, No. 20, 1994, pp. 4776–4786.

K. Yoshioka et al., "Participation of rhop21 in serum–dependent invasion by rat ascites hepatoma cells", FEBS Letters 372 (1995), pp. 25–28.

J. Hartwig et al., "Thrombin Receptor Ligation and Activated Rac Uncap Actin Filament Barbed Ends through Phosphoinositide Synthesis in Permeabilized Human Platelets", Cell, vol. 82, 1995, pp. 643–653.

P. Janmey, "Phosphoinositides and Calcium as Regulators of Cellular Actin Assembly and Disassembly", Annu. Rev. Physiol., 1994, 56:169–91.

D. Pantaloni et al., "How Profilin Promotes Actin Filament Assembly in the Presence of Thymosin $\beta 4$", Cell, vol. 75, Dec. 1993, pp. 1007–1014.

J. Theriot et al., "The Three Faces of Profilin", Cell, vol. 75, Dec. 1993, pp. 835–838.

K. Takaishi et al., "Translocation of activated Rho from the cytoplasm to membrane ruffling area, cell–cell adhesion sites and cleavage furrows", Oncogene, 1995, 11:39–48.

N. Kumagai et al., "ADP–ribosylation of rho p21 Inhibits Lysophosophatidic Acid–induced Protein Tyrosine Phosphorylation and Phosphatidylinositol 3–Kinase Activation in Cultured Swiss 3T3 Cells", J. of Biological Chemistry, vol. 268, No. 33, Nov. 1993, pp. 24535–24538.

S. Rankin et al., "Botulinum C3 exoenzyme blocks the tryosine phosphorylation of $p125^{FAK}$ and paxilin induced by bombesin and endothelin", FEBS Letters 354 (1994), pp. 315–319.

M. Seckl et al., "Guanosine 5'–3–O–(Thio)triphosphate Stimulates Tyrosine Phosphorylation of $p125^{FAK}$ and Paxillin in Permeabilized Swiss 3T3 Cells", J. of Biol. Chem., vol. 270, No. 12, Mar. 1995, pp. 6984–6990.

D. Postma et al., "Genetic Susceptibility to Asthma—Bronchial Hyperresponsiveness Coinherited with a major Gene for Atopy", The New England Journal of Medicine, Oct. 5, 1995, pp. 894–900.

N. Watanabe et al., "Cloning and analysis of novel Rho target protein, p140", abstract, Japanese Biochemical Society in Japan. Aug. 26, 1996.

FIG. 3A

```
              ▼
MEPSGGGLGP GRGTRDKKKG RSPDELPATG GDGGKHKKFL ERFTSMRIKK    50
EKEKPNSAHR NSSASYGDDP TAQSLQDISD EQVLVLFEQM LVDMNLNEEK   100
QQPLREKDIV IKREMVSQYL HTSKAGMNQK ESSRSAMMYI QELRSGLRDM   150
HLLSCLESLR VSLNNNPVSW VQTFGAEGLA SLLDILKRLH DEKEETSGNY   200
DSRNQHEIIR CLKAFMNNKF GIKTMLETEE GILLLVRAMD PAVPNMMIDA   250
AKLLSALCIL PQPEDMNERV LEAMTERAEM DEVERFQPLL DGLKSGTSIA   300
LKVGCLQLIN ALITPAEELD FRVHIRSELM RLGLHQVLQE LREIENEDMK   350
VQLCVFDEQG DEDFFDLKGR LDDIRMEMDD FGEVFQIILN TVKDSKAEPH   400
FLSILQHLLL VRNDYEARPQ YYKLIEECVS QIVLHKNGTD PDFKCRHLQI   450
DIERLVDQMI DKTKVEKSEA KATELEKKLD SELTARHELQ VEMKKMENDF   500
EQKLQDLQGE KDALDSEKQQ ITAQKQDLEA EVSKLTGEVA KLSKELEDAK   550
NEMASLSAVV VAPSVSSSAA VPPAPPLPGD SGTVIPPPPP PPPLPGGVVP   600
PSPPLPPGTC IPPPPPLPGG ACIPPPPPQLP GSAAIPPPPP LPGVASIPPP   650
```

FIG. 3B

```
PPLPGATAIP PPPPLPGATA IPPPPPLPGG TGIPPPPPPL PGSVGVPPPP  700
PLPGGPGLPP PPPPFPGAPG IPPPPPGMGV PPPPPFGFGV PAAPVLPFGL  750
TPKKVYKPEV QLRRPNWSKF VAEDLSQDCF WTKVKEDRFE NNELFAKLTL  800
AFSAQTKTSK AKKDQEGGEE KKSVQKKKVK ELKVLDSKTA QNLSIFLGSF  850
RMPYQEIKNV ILEVNEAVLT ESMIQNLIKQ MPEPEQLKML SELKEEYDDL  900
AESEQFGVVM GTVPRLRPRL NAILFKLQFS EQVENIKPEI VSVTAACEEL  950
RKSENFSSLL ELTLLVGNYM NAGSRNAGAF GFNISFLCKL RDTKSADQKM 1000
TLLHFLAELC ENDHPEVLKF PDELAHVEKA SRVSAENLQK SLDQMKKQIA 1050
DVERDVQNFP AATDEKDKFV EKMTSFVKDA QEQYNKLRMM HSNMETLYKE 1100
LGDYFVFDPK KLSVEEFFMD LHNFRNMFLQ AVKENQKRRE TEEKMRRAKL 1150
AKEKAEKERL EKQQKREQLI DMNAEGDETG VMDSLLEALQ SGAAFRKKRG 1200
PRQVNRKAGC AVTSLLASEL TKDDAMAPGP VKVPKKSEGV PTILEEAKEL 1250
VGRAS*
```

28S –

18S – heart lung brain kidney testis skeletal muscle thymus spleen liver stomach small intestine colon

F I G. 5 contig. map of human mDia

FIG. 15A

| | |
|---|---|
| Human | MRAKPLGFQGRGAWAGGAGGREGVLAEAGKGRRGPGIPGGVGAGSPASVN |
| Mouse | ------------------------------------------------- |

| | |
|---|---|
| Human | IKKEKEKPNSAHRNSSASYGDDPTAQSLQDVSDEQVLVLFEQMLLDMNLN |
| | ||||||||||||||||||||||||||||| ||||||||||||| ||||| |
| Mouse | IKKEKEKPNSAHRNS<u>SASYGDDPTAQSLQD</u>ISDEQVLVLFEQMLVDMNLN |

| | |
|---|---|
| Human | RDMPLLSCLESLRVSLNNNPVSWVQTFGAEGLASLLDILKRLHDEKEETA |
| | ||| |||||||||||||||||||||||||||||||||||||||||||| |
| Mouse | <u>RDMH</u>LLSCLESLRVSLNNNPVSWVQTFGAEGLASLLDILKRLHDEKEETS |

A

| | |
|---|---|
| Human | IDAAKLLSALCILPQPEDMNERVLEAMTERAEMDEVERFQPLLDGLKSGT |
| | ||||||||||||||||||||||||||||||||||||||||||||||||| |
| Mouse | <u>IDAAKLLSALCIL</u>PQPEDMNERVLEAMTERAEMDEVERFQPLLDGLKSGT |

| | |
|---|---|
| Human | DMRVQLNVFDEQGEEDSYDLKGRLDDIRMEMDDFNEVFQILLNTVKDSKA |
| | || ||| |||||| || ||||||||||||||||| ||||| ||||||||| |
| Mouse | DMKVQLCVFDEQGDEDFFDLKGRLDDIRMEMDDFGEVFQIILNTVKDSKA |

| | |
|---|---|
| Human | LQIEIEGLIDQMIDKTKVEKSEAKAAELEKKLDSELTARHELQVEMKKME |
| | ||| || | ||||||||||||||| ||||||||||||||||||||||||| |
| Mouse | LQIDIERLVDQMIDKTKVEKSEAKATELEKKLDSELTARHELQVEMKKME |

| | |
|---|---|
| Human | EDAKKEMASLSAAAITVPPSVPSRAPVPPAPPLPGDSGTIIPPPPAPGDS |
| | |||| ||||||| | ||| | | |||||||||||| ||||| | |
| Mouse | EDAK<u>NEMASLSAVV</u>--VAPSVSSSAAV<u>PPAPPLPGDSGTVIPPPP-P</u>--- |

FIG. 15B

```
RDMEPPGGSLGPGRGTRDKKKGRSPDELPSA-GGDGGKSKKFLERFTSMR    99
   ||| || ||||||||||||||||||||| | |||||| |||||||||||
--MEPSGGGLGPGRGTRDKKKGRSPDELP-ATGGDGGKHKKFLERFTSMR    47

EEKQQPLREKDIIIKREMVSQYLYTSKAGMSQKESSKSAMMYIQELRSGL    199
|||||||||| ||||||||| ||||||| ||||| ||||||||||||||
EEKQQPLREKDIVIKREMVSQYLHTSKAGMNQKESSRSAMMYIQELRSGL    147

GSYDSRNKHEIIRCLKAFMNNKFGIKTMLETEEGILLLVRAMDPAVPNMM    299
  |||||  ||||||||||||||||||||||||||||||||||||||||
GNYDSRNQHEIIRCLKAFMNNKFGIKTMLETEEGILLLVRAMDPAVPNMM    247

TIALKVGCLQLINALITPAEELDFRVHIRSELMRLGLHQVLQDLREIENE    399
 |||||||||||||||||||||||||||||||||||||||||| |||||
SIALKVGCLQLINALITPAEELDFRVHIRSELMRLGLHQVLQELREIENE    347

EPHFLSILQHLLLVRNDYEARPQYYKLIEECISQIVLHKNGADPDFKCRH    499
||||||||||||||||||||||||||||||| ||||||||| ||||||
EPHFLSILQHLLLVRNDYEARPQYYKLIEECVSQIVLHKNGTDPDFKCRH    447

SXFEQKLQDLQGEKDALHSEKQQIATE-KQDLEAEVSQLTGEVAKLTKEL    598
 ||||||||||||||| |||||| |  |||||||| ||||||||| |||
NDFEQKLQDLQGEKDALDSEKQQI-TAQKQDLEAEVSKLTGEVAKLSKEL    546

TTPPPPPPPPPP-PPLPGGVCISSPPSLPGGTA-ISPPPP-LSGDATIP    695
  ||| |   || |||| | ||  || ||||  | |||| | |   ||
--PPPLPGGVVPPSPPLPPGTCIPPPPPLPGG-ACI-PPPPQLPGSAAIP    636
```

FIG. 16A

```
Human   PPPPLPEGVG-IPSPSSLPGGTAIPPPPPLPGSAR-IPPPPPPLPGSAG
        ||||||  ||  || |   |||  |||||||||||   ||||||  ||| |
Mouse   PPPPLP-GVASIPPPPPLPGATAIPPPPPLPG-ATAIPPPPP-LPGGTG
                          B
Human   PPPFGFGVPAAPVLPFGLTPKKLYKPEVQLRRPNWSKLVAEDLSQDCFW
        ||||||||||||||||||||||||| |||||||||||| |||||||||
Mouse   PPPFGFGVPAAPVLPFGLTPKKVYKPEVQLRRPNWSKFVAEDLSQDCFW Human   KVLDSKTAQNLSIFLGSFRMPYQEIKNVILEVNEAVLTESMIQNLIKQM
        ||||||||||||||||||||||||||||||||||||||||||||||||
Mouse   KVLDSKTAQNLSIFLGSFRMPYQEIKNVILEVNEAVLTESMIQNLIKQM Human   VENIKPEIVSVTAACEELRKSESFSNLLEITLLVGNYMNAGSRNAGAFG
        |||||||||||||||||||||||| | ||| |||||||||||||||||
Mouse   VENIKPEIVSVTAACEELRKSENFSSLLELTLLVGNYMNAGSRNAGAFG
                                                       C
Human   VSAENLQKNLDQMKKQISDVERDVQNFPAATDEKDKFVEKMTSFVKDAQ
        ||||||||  ||||||| ||||||||||||||||||||||||||||||
Mouse   VSAENLQKSLDQMKKQIADVERDVQNFPAATDEKDKFVEKMTSFVKDAQ Human   KENQKRRETEEKMRRAKLAKEKAEKERLEKQQKREQLIDMNAEGDETGV
        ||||||||||||||||||||||||||||||||||||||||||||||||
Mouse   KENQKRRETEEKMRRAKLAKEKAEKERLEKQQKREQLIDMNAEGDETGV Human   VSKNSETFPTILEEAKELVGRAS
        |  | ||||||||||||||||||
Mouse   VPKKSEGVPTILEEAKELVGRAS
```

FIG. 16B

```
IPPPPPPLPGEAGMPPPPPPLPGGPGIPPPPP-FPGGPGIPPPPPGMGMPP       792
IIIIIIIII  I IIIIII IIIIII IIIII III IIIIIIIIII II
IPPPPPPLPGSVGVPPPPP-LPGGPGLPPPPPPFPGAPGIPPPPPGMGVPP       732

TKVKEDRFENNELFAKLTLTFSAQTKTSKAKKDQEGGEEKKSVQKKKVKEL       892
IIIIIIIIIIIIIIIIIII IIIIIIIIIIIIIIIIIIIIIIIIIIIIII
TKVKEDRFENNELFAKLTLAFSAQTKTSKAKKDQEGGEEKKSVQKKKVKEL       832

PEPEQLKMLSELKDEYDDLAESEQFGVVMGTVPRLRPRLNAILFKLQFSEQ       992
IIIIIIIIIII IIIIIIIIIIIIIIIIIIIIIIIIIIIIIIIIIIIIII
PEPEQLKMLSELKEEYDDLAESEQFGVVMGTVPRLRPRLNAILFKLQFSEQ       932

FNISFLCKLRDTKSTDQKMTLLHFLAELCENDYPDVLKFPDELAHVEKASR      1092
IIIIIIIIIIIIII IIIIIIIIIIIIIII I IIIIIIIIIIIIIIIII
FNISFLCKLRDTKSADQKMTLLHFLAELCENDHPEVLKFPDELAHVEKASR      1032

EQYNKLRMMHSNMETLYKELGEYFLFDPKKLSVEEFFMDLHNFRNMFLQAV      1192
IIIIIIIIIIIIIIIIIII II IIIIIIIIIIIIIIIIIIIIIIIIIII
EQYNKLRMMHSNMETLYKELGDYFVFDPKKLSVEEFFMDLHNFRNMFLQAV      1132

MDSLLEALQSGAAFRRKRGPRQANRKAGCAVTSLLASELTKDDAMAAVPAK      1292
IIIIIIIIIIIIIIIIIIIII IIIIIIIIIIIIIIIIIIIIII  I I
MDSLLEALQSGAAFRRKRGPRQVNRKAGCAVTSLLASELTKDDAMAPGPVK      1232

1315

1255
```

RHO TARGET PROTEIN HUMAN MDIA AND GENE ENCODING SAME

BACKGROUND OF THE INVENTION

1. Field of the Invention

The present invention relates to a Rho target protein derived from Homo sapiens and more specifically relates to a gene encoding the same and a diagnostic agent containing the same.

2. BACKGROUND ART

A group of small GTP-binding proteins (G-proteins) with molecular weights of 20,000–30,000 with no subunit structure is observed in organisms. To date, over fifty or more members have been found as the superfamily of the small G-proteins in a variety of organisms, from yeast to mammals. The small G-proteins are divided into four families of Ras, Rho, Rab and the others based on homologies of amino acid sequences. It has been revealed that the small G-proteins control a variety of cellular functions. For example, the Ras protein is considered to control cell proliferation and differentiation, and the Rho protein is considered to control cell morphological change, adhesion and motility.

The Rho protein, having GDP/GTP-binding activity and intrinsic GTPase activity, is believed to be involved in cytoskeletal responses to extracellular signals such as lysophosphatidic acid (LPA) and certain growth factors. When the inactive GDP-binding Rho is stimulated, it is transformed to the active GTP-binding Rho protein (hereinafter referred to as "the activated Rho protein") by GDP/GTP exchange proteins such as Smg GDS, Dbl or Ost. The activated Rho protein then acts on target proteins to form stress fibers and focal contacts, thus inducing the cell adhesion and motility (Experimental Medicine, Vol. 12, No. 8, 97–102 (1994); Takai, Y. et al., Trends Biochem. Sci., 20, 227–231 (1995)). On the other hand, the intrinsic GTPase activity of the Rho protein transforms the activated Rho protein to the GDP-binding Rho protein. This intrinsic GTPase activity is enhanced by what is called GTPase-activating proteins (GAP) (Lamarche, N. & Hall, A. et al., TIG, 10, 436–440 (1994)).

The Rho family proteins, including RhoA, RhoB, RhoC, Rac1, Rac2 and Cdc42, share more than 50% sequence identity with each other. The Rho family proteins are believed to be involved in the biological responses inducing the formation of stress fibers and focal contacts in response to extracellular signals such as lysophosphatidic acid (LPA) and growth factors (A. J. Ridley & A. Hall, Cell, 70, 389–399 (1992); A. J. Ridley & A. Hall, EMBO J., 1353, 2600–2610 (1994)). The subfamily Rho is also considered to be implicated in physiological functions associated with cytoskeletal rearrangements, such as cell morphological change (H. F. Parterson et al., J. Cell Biol., 111, 1001–1007 (1990)), cell adhesion (Morii, N. et al., J. Biol. Chem., 267, 20921–20926 (1992); T. Tominaga et al., J. Cell Biol., 120, 1529–1537 (1993); Nusrat, A. et al., Proc. Natl. Acad. Sci. USA, 92, 10629–10633 (1995); Landanna, C. et al., Science, 271, 981–983 (1996)), cell motility (K. Takaishi et al., oncogene, 9, 273–279 (1994)), and cytokinesis (K. Kishi et al., J. Cell Biol., 120, 1187–1195 (1993); I. Mabuchi et al., Zygote, 1, 325–331 (1993)). In addition, it has been suggested that the Rho is involved in the regulation of smooth muscle contraction (K. Hirata et al., J. Biol. Chem., 267, 8719–8722 (1992); M. Noda et al., FEBS Lett., 367, 246–250 (1995); M. Gong et al., Proc. Natl. Acad. Sci. USA, 93, 1340–1345 (1996)), and the expression of phosphatidylinositol 3-kinase (PI3 kinase) (J. Zhang et al., J. Biol. Chem., 268, 22251–22254 (1993)), phosphatidylinositol 4-phosphate 5-kinase (PI4,5-kinase) (L. D. Chong et al., Cell, 79, 507–513 (1994)) and c-fos (C. S. Hill et al., Cell, 81, 1159–1170 (1995)).

Recently, it has also be found that Ras-dependent tumorigenesis is suppressed when the Rho protein of which the amino acid sequence has been partly substituted is introduced to cells, revealing that the Rho protein plays an important role in Ras-induced transformation, that is, tumorigenesis (G. C. Prendergast et al., Oncogene, 10, 2289–2296 (1995); Khosravi-Far, R. et al., Mol. Cell. Biol., 15, 6443–6453 (1995); R. Qiu et al., Proc. Natl. Acad. Sci. USA, 92, 11781–11785 (1995); Lebowitz, P. et al., Mol. Cell, Biol., 15, 6613–6622 (1995)).

It has also been demonstrated that mutation of GDP/GTP-exchange proteins which act on the Rho protein results in cell transformation (Collard, J., Int. J. Oncol., 8, 131–138 (1996); Hart, M. et al., J. Biol. Chem., 269, 62–65 (1994); Horii, Y. et al., EMBO J., 13, 4776–4786 (1994)).

In addition, the Rho protein has been elucidated to be involved in cancer cell invasion, that is, metastasis (Yoshioka, K. et al., FEBS Lett., 372, 25–28 (1995)). The cancer cell invasion is closely dependent on changes in cancer cell activity to form cell adhesion. In this context, the Rho protein is also known to be involved in the formation of cell adhesion (see above Morii, N. et al. (1992); Tominaga, T. et al. (1993); Nusrat, A. et al. (1995); Landanna C. et al. (1996)).

Furthermore, the involvement of phosphoinositide kinases in Rho signaling was reported. Rho (Chong, L. D. et al., Cell, 79, 507–513, 1994) and Rac (Hartwig, J. H. et al., Cell, 82, 643–653, 1995), another member of Rho family low-molecular-weight G protein, were demonstrated to stimulate the synthesis of phosphatidylinositol bisphosphate (PIP2) in different cell systems. Since the binding of PIP2 is believed to regulate functions of many actin-associated proteins (Janmey, P. A., Ann. Rev. Physiol., 56, 169–191, 1994), its synthesis in subcellular localization may promote focal actin rearrangement. One of the proteins regulated by PIP2 is profilin, which makes a complex with actin monomer and releases actin upon PIP2 binding. Profilin also promotes actin filament assembly in the presence of thymosin β4 (Pantaloni, D. and Carlier, M-F, Cell, 75, 1007–1014, 1993). Focal accumulation of profilin is, therefore, supposed to be important in actin reorganization (Theriot, J. A. and Mitchison, T. J., Cell, 75, 835–838, 1993).

The actin cytoskeleton plays an important role in cell motility, morphology, phagocytosis and cytokinesis. It is spatially and dynamically rearranged, which provides forces for morphological changes and cell surface movement in most eukaryotic cells. The rearrangement of actin is caused rapidly by extracellular stimuli and a series of actin-binding proteins are believed to act synergistically in polymerization, crosslinking and anchoring of actin filaments. The low-molecular-weight G protein Rho has been shown to be required for a variety of actin-dependent cellular processes such as platelet aggregation (Morii, N. et al., J. Biol. Chem., 267, 20921–20926, 1992), lymphocyte adhesion (Tominaga, T. et al., J. Cell. Biol., 120, 1529–1537, 1993), acceleration of cell motility (Takaishi, K. et al., Oncogene, 11, 39–48, 1995), and contractile ring formation and cytokinesis (Kishi, K. et al., J. Cell. Biol., 120, 1187–1195, 1993 and Mabuchi, I. et al., Zygote, 1, 325–331, 1993). In cultured fibroblasts, microinjection of Rho protein rapidly induces formation of the actin stress fibers or focal adhesion. In contrast, inactivation of Rho by a botulinum C3 extracellular enzyme (ADP-ribosyltransferase) inhibits this process (Ridley, A. J. and Hall, A., Cell, 70, 389–399, 1992). The treatment with the C3 extracellular enzyme also inhibits lysophosphatidic acid (LPA)-, endothelin- or GTPγS-induced tyrosine phosphorylation of focal adhesion kinase (FAK) and paxillin (Kumagai, N. et al., J. Biol. Chem., 268, 24535–24538, 1993; Rankin, S. et al., FEBS Lett., 354, 315–319, 1994; Ridley, A. J. and Hall, A., Cell, 70, 389–399, 1992; and Seckl, M.J. et al., J. Biol. Chem., 270, 6984–6990, 1995). These results indicate that Rho protein regulates signal transduction pathways linking the extracellular stimuli to the rearrangement of actine cytoskeleton.

Rho protein is believed to have many target molecules and regulate a number of the signal transduction pathways. Recently, several proteins have been reported as possible target molecules in mammals. These proteins are protein kinase N (PKN) (Watanabe, G. et al., Science, 271, 645–648, 1996; Amano, M. et al., Science 271, 648–650, 1996), rhophilin (Watanabe, G. et al., Science, 271, 645–648, 1996), citron (Madaule, P. et al., FEBS Lett., 377, 243–248, 1995), pl6OROCK (Ishizaki, T. et al., EMBO J., 15, 1885–1896, 1996), ROKα (Leung, T. et al., J. Biol. Chem., 270, 29051–29054, 1995), Rho-associated kinase (Matsui, T. et al., EMBO J., 15, 1885–1893 (1996), rhotekin (Reid, T. et al., J. Biol. Chem., 271, 9816–9822, 1996), myosin light-chain phosphatase (Kimura, K. et al., Science, 273, 245–248, 1996), murine mDia (Narumiya, Shu et al., Proceedings of Joint Annual Conference of The Japanese Society of Biochemistry and The Japanese Society of Molecular Biology, pp31 and 319, 1996). All these proteins bind to GTP-binding RhoA protein, except that citron binds also to GTP-binding Rac1 protein.

Recently, the following target proteins of Rho protein in *Saccharomyces cerevisiae* have been reported: Pkc1P (Nonaka, H. et al., EMBO J., 14, 5931–5938, 1995; Kamada, Y. et al., J. Biol. Chem., 271, 9193–9196, 1996), 1,3-β-glucan synthesizing enzyme (Drgonova, J. et al., Science, 272, 277–279, 1996; Qadota, H. et al., Science, 272, 279–281) and Bni1p (Kohno, H. et al., EMBO J., 15, 6060–6068, 1996).

On the other hand, Bni1p of *Saccharomyces cerevisiae* (Kohno, H. et al., 1996, loc. cit.), *Drosophila diaphanous* (Castrillion, D. H. and Wasserman, S. A., Development, 120, 3367–3377, 1994), *Drosophila cappuccino* (Emons et al., Genes and Dev., 9, 2482–2494, 1995), murine formin (Woychick et al., Nature 346, 850–853, 1990) and murine mDia (Narumiya et al., 1996, loc. cit.) are known as proteins containing a poly-proline region and an FH-2 region.

However, there has been no report on a human Rho target protein which binds to profilin to regulate rearrangement of Rho protein and actin cytoskeleton insofar far as the inventors of the present invention know.

SUMMARY OF THE INVENTION

The inventors of the present invention have now identified a Rho target protein (murine mDia) using an yeast two hybrid system. It is a mammalian homolog of *Drosophila diaphanous* required for cytokinesis and contains repetitive poly-proline stretches and a formin homology (FH-2) domain. Murine mDia selectively binds to the GTP-bound form of Rho through its amino-terminal region and binds to an actin binding protein, profilin. Murine mDia, profilin and Rho protein were co-localized in membrane ruffles of spreading fibroblasts and in the cleavage furrow of dividing cells and were recruited by fibronectin-coated latex beads to the plasma membrane beneath the beads. These results suggest that one of the mechanisms for Rho protein-induced actin rearrangement is its recruitment of the profilactin complex via mDia at a specific site in the cells.

Furthermore, the present inventors successfully cloned cDNA of a human counterpart (human mDia) of murine mDia, a target protein of the activated Rho protein (Example 10). Furthermore, the position (locus) of the human mDia gene on a chromosome was determined using a probe and a primer comprising of a partial sequence of the human mDia cDNA. As a result, the locus of the human mDia gene was found to be identical to the loci of bronchial asthma and respiratory tract hypersensitivity gene and to the region on the chromosome where deletion or rearrangement is observed in acute myelocytic leukemia (AML) and myelodysplasia syndrome (MDS). These findings suggest that the mutation (amplification, deletion or rearrangement) of the mDia gene or the decrease or acceleration of its expression is a risk factor of bronchial asthma and one of characteristics of AML and MDS. The present invention is based on these findings.

Accordingly, an objective of the present invention is to provide a human Rho target protein having profilin-binding activity.

Another objective of the present invention is to provide a nucleotide sequence coding for said protein, a vector containing said nucleotide sequence, a host cell transformed by said vector, a method of producing said protein and a screening method to inhibit the binding between the activated Rho protein or profilin and its target protein.

Another objective of the present invention is to provide a partial fragment of the gene coding for said protein, a probe containing said partial fragment, a diagnostic agent containing said probe or said nucleotide sequence and a method of detecting mutations in the mDia gene using said probe.

The protein according to the present invention is a human-derived protein which has the following characteristics (referred to as "human mDia" in this specification):

(1) having the activated Rho protein binding activity,
(2) having the profilin binding activity,
(3) the gene coding for the protein being located at human chromosome 5q31.2, and
(4) having a molecular weight of about 150 kDa as measured by SDS-PAGE.

As mentioned above, known proteins having the binding activity to the activated Rho protein include protein kinase N (PKN), rhophilin, citron, p160ROCK, Rho kinase, ROKα, rhotekin, a myosin-binding subunit of myosin light chain phosphatase and mouse mDia for mammalian cells; and Pkc1P, 1,3-β-glucan synthesizing enzyme and Bni1p for *Saccharomyces cerevisiae*. However, the present inventors have confirmed that the human mDia is a protein different from these proteins.

Among these proteins, Bni1p of Saccharomyces cerevisiae has the poly-proline region and the FH-2 region in addition to the activated Rho binding region (Example 2 and FIG. 4); however, homology of the amino acid sequence of human mDia to that of Bni1p is extremely low.

Furthermore, *Drosophila diaphanous* and *cappuccino* have a poly-proline region and an FH-2 region and diaphanous further has an amino acid sequence homologous to that of the activated Rho-binding region. However, homology of the amino acid sequence of human mDia to those of diaphanous and cappuccino is extremely as low as in the case of Bni1p.

BRIEF DESCRIPTION OF THE DRAWINGS

FIG. 1 is a photograph showing binding of clone 50 and Rho protein in a two hybrid system. Val, Asn, WT and Cdc42 represent RhoA$^{Val14}$, RhoA$^{Asn19}$, wild-type RhoA and Cdc42Hs, respectively. ΔAsn and ΔWT represent Rho$^{Asn19}$ and wild-type RhoA truncated at Ala$^{181}$. A Lex-binding domain without fusion to other proteins and lamin were used as a negative control.

The RhoA$^{Val14}$ truncated at Ala$^{181}$ was not used in this experiment because it bound a VP16-activated domain without fusion to other proteins showing high LacZ activity.

Figure 2:
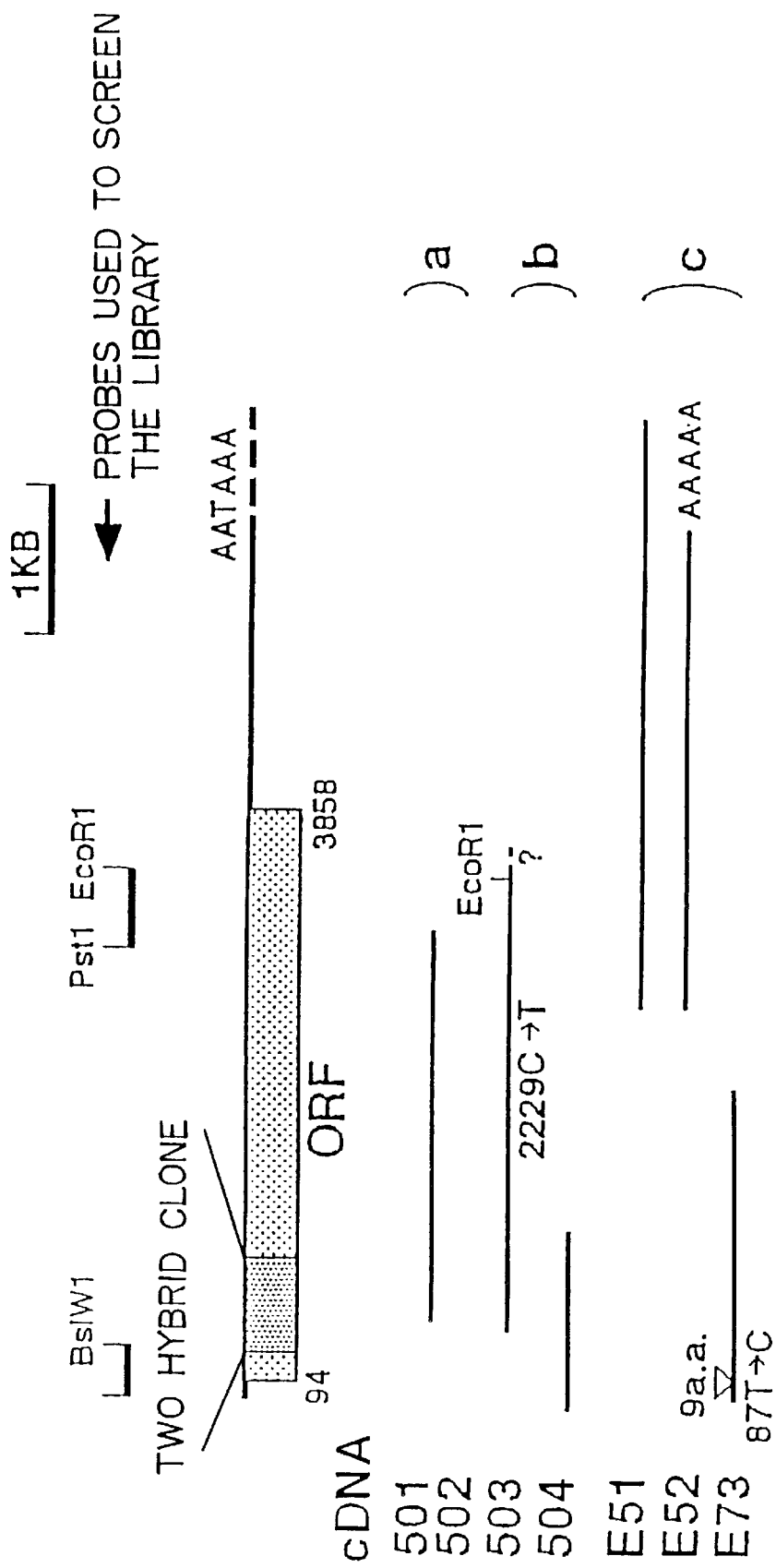

FIG. 2 is a schematic representation of isolated murine mDia (p140mDia).

ORF is shown by a dotted box. Conversions in bases from T to C at nucleotide 78 in 503 cDNA and from C to T at nucleotide 229 in E73 cDNA were found. Libraries a, b and c represent mouse brain library 936309 (Stratagene), ML3000a (Clontech) and a mouse embryo library, respectively. Insertion of 9 amino acids was observed in E73 cDNA.

FIG. 3 shows a deduced amino acid sequence of p140mDia (SEQ ID NO: 1). The sequence obtained by a two hybrid system is shown with a thick underline and the repetitive structure of the proline-rich region is shown with a broken underline and the FH-2 region is shown with a thin underline. The arrowhead indicates the insertion site for the 9 amino acids.

Figure 4:
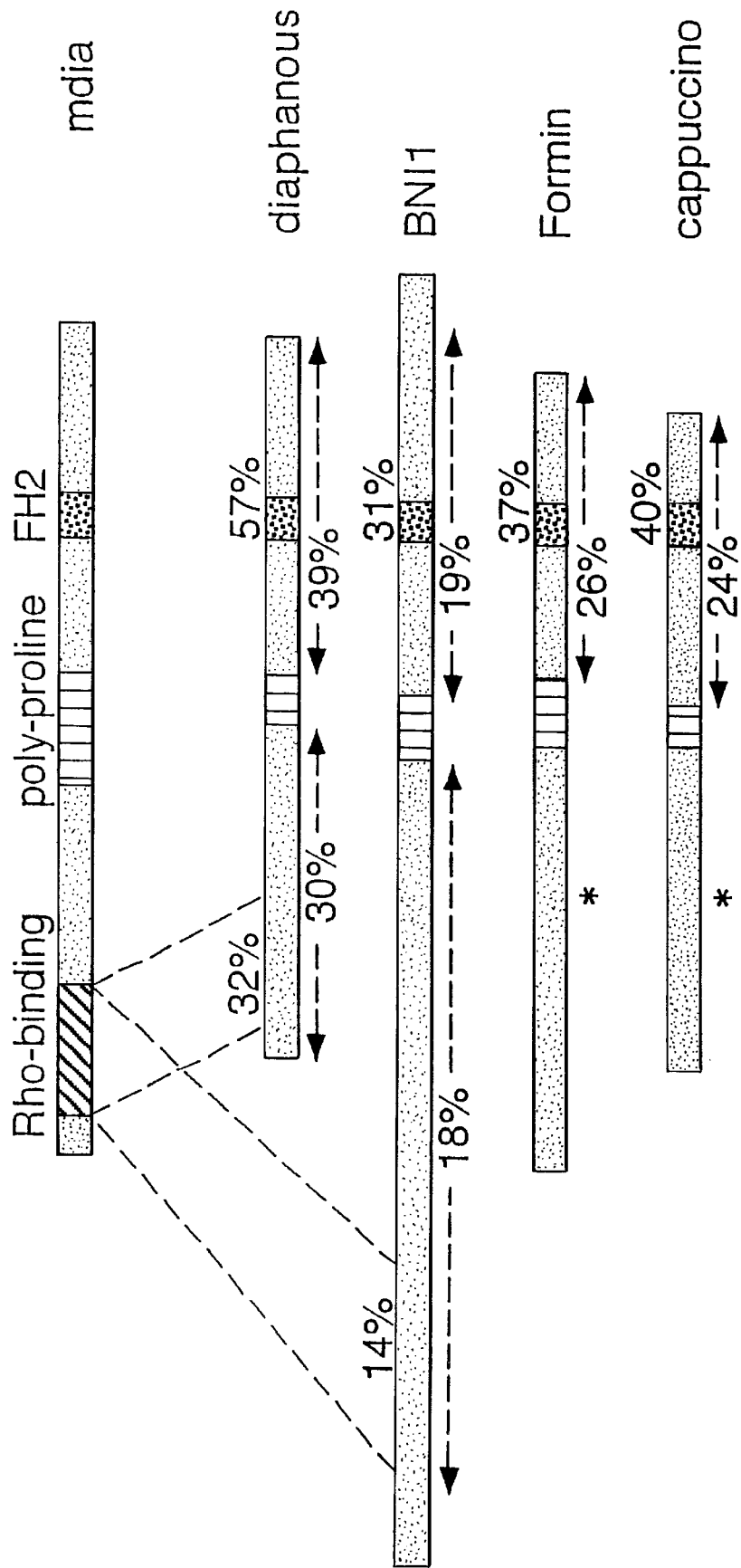

FIG. 4 is a schematic representation for comparison of p140mDia and other proteins having the FH-2 region. The sequence of p140mDia was compared with those of *Drosophila diaphanous*, *S. cerevisiae* Bni1p, rat formin and *Drosophila cappuccino*. The comparison was made in the deduced Rho-binding region (Rho-binding), in the region between the N-terminal and the proline-rich region (polyproline), in the FH-2 region and in the region between the proline-rich region and the C-terminal region. Homology in amino acid sequences is shown by percentage. No homology was observed in the N-terminal regions of formin and cappuccino. All the sequences shown to have the polyproline stretches in the middle of the sequences and homologous sequences in the half of the C-terminal side.

FIG. 5 shows RNA blots (electrophoretic photograph) by Northern blot analysis demonstrating distribution of p140mDia in the tissue of various murine organs.

Figure 6:
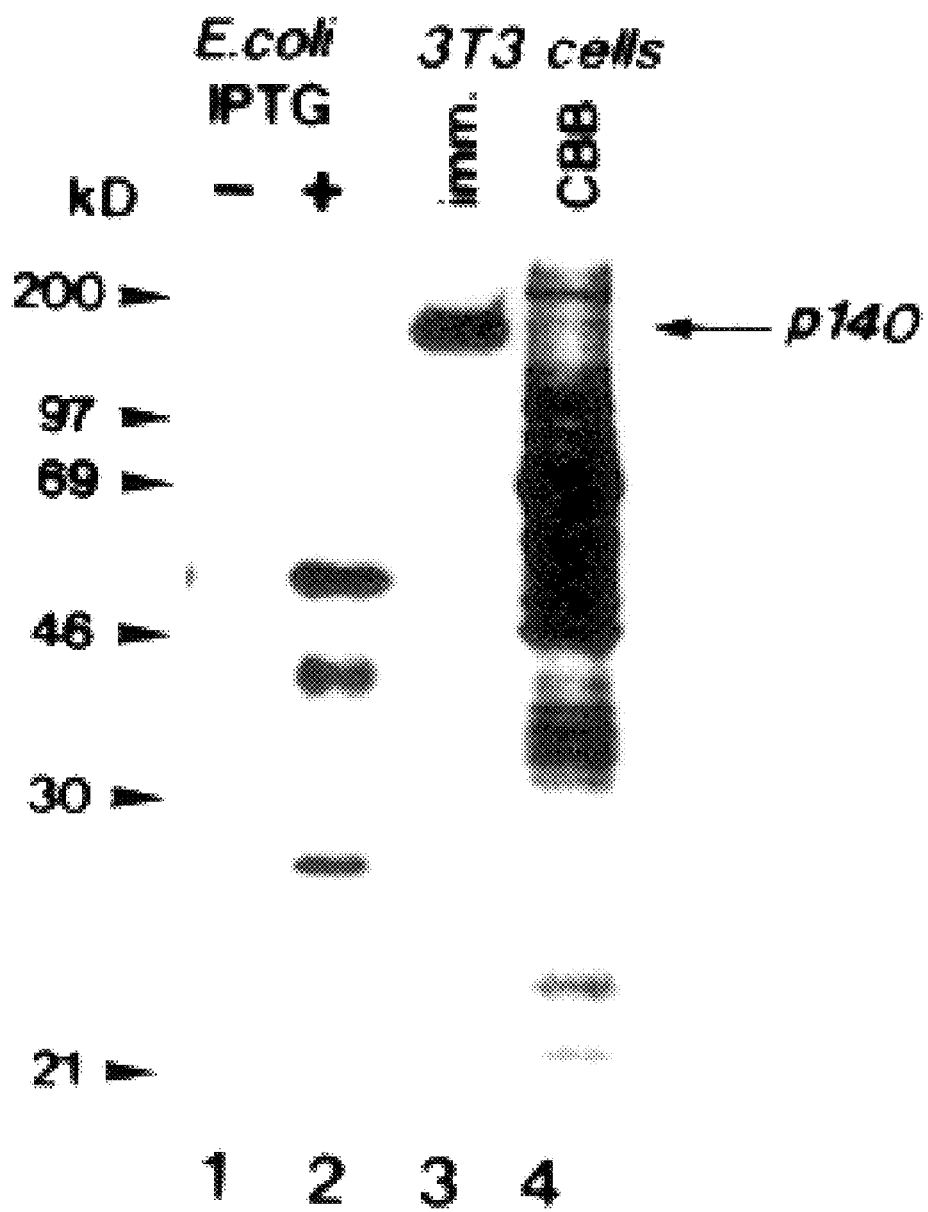

FIG. 6 is an electrophoretic photograph showing the specificity of anti-p140mDia antibody.

Antiserum (AP50) is an antibody to the peptide encoded by clone 50 obtained by a two hybrid system. Its specificity was examined by Western blotting against whole lysates of *Escherichia coli*, which expresses recombinant protein, before induction (lane 1) and after induction (lane 2) and a whole lysate of Swiss 3T3 cells (lane 3). Lane 4 shows a CBB-stained whole cell lysate.

Figure 7:
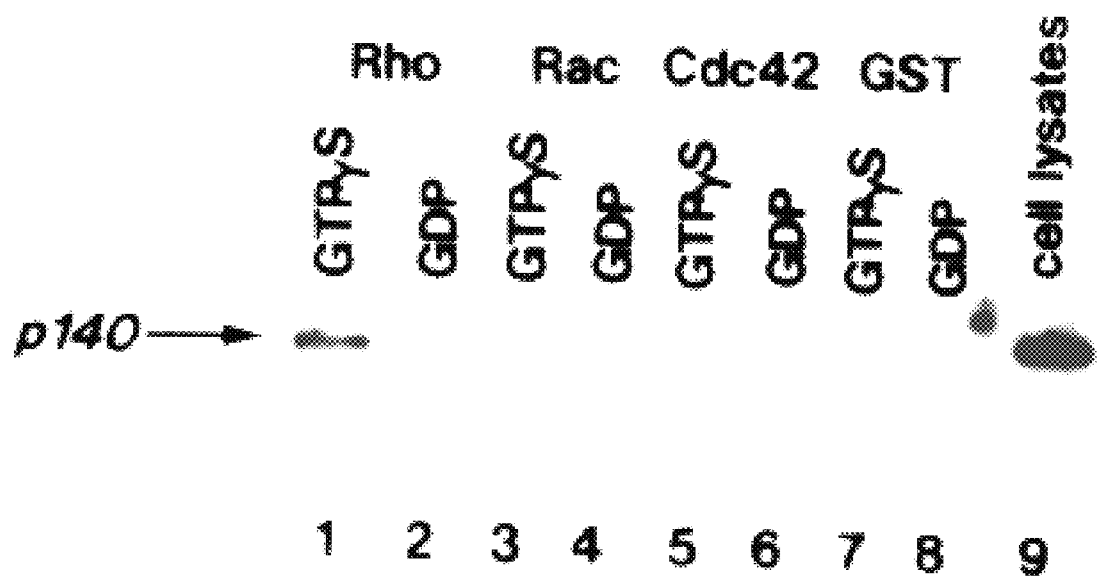

FIG. 7 is an electrophoretic photograph showing precipitation of p140mDia by GTPγS-binding-type Rho protein. A whole lysate of Swiss 3T3 cells was incubated with GTPγS binding-type or GDP binding-type GST-Rho, GST-Rac, GST-Cdc42 or GST. Bound proteins were precipitated by glutathione agarose beads and analyzed by immunoblotting using anti-p140mDia antibody. In lane 9 (cell lysate), p140mDia in the whole cell lysate was detected by the antibody.

Figure 8:
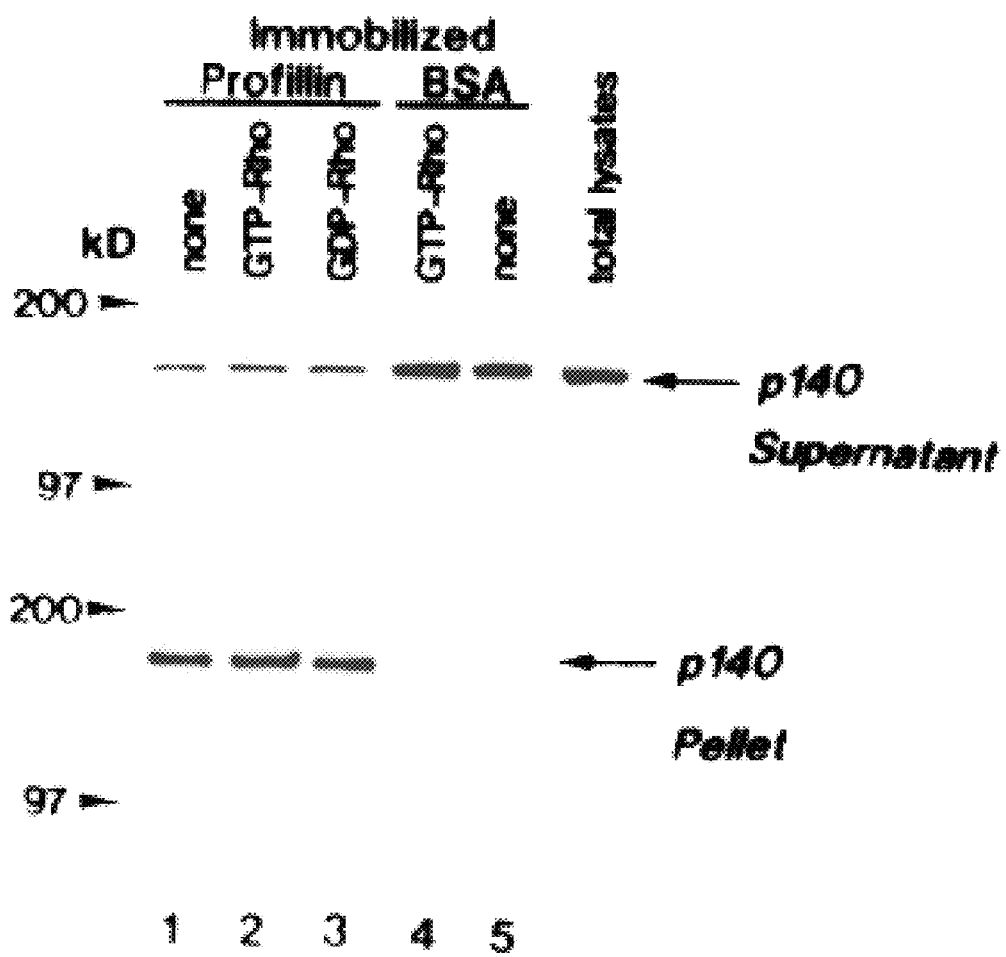

FIG. 8 is an electrophoretic photograph showing in vitro binding of p140mDia to profilin. A Swiss 3T3 cell lysate was incubated in the presence or absence of the GTPγS- or GDP-binding-type GST-Rho protein with agarose beads immobilized with profilin or BSA to precipitate bound proteins. The resultant pellet and supernatant were analyzed by immunoblotting using anti-p140mDia antibody.

Figure 9:
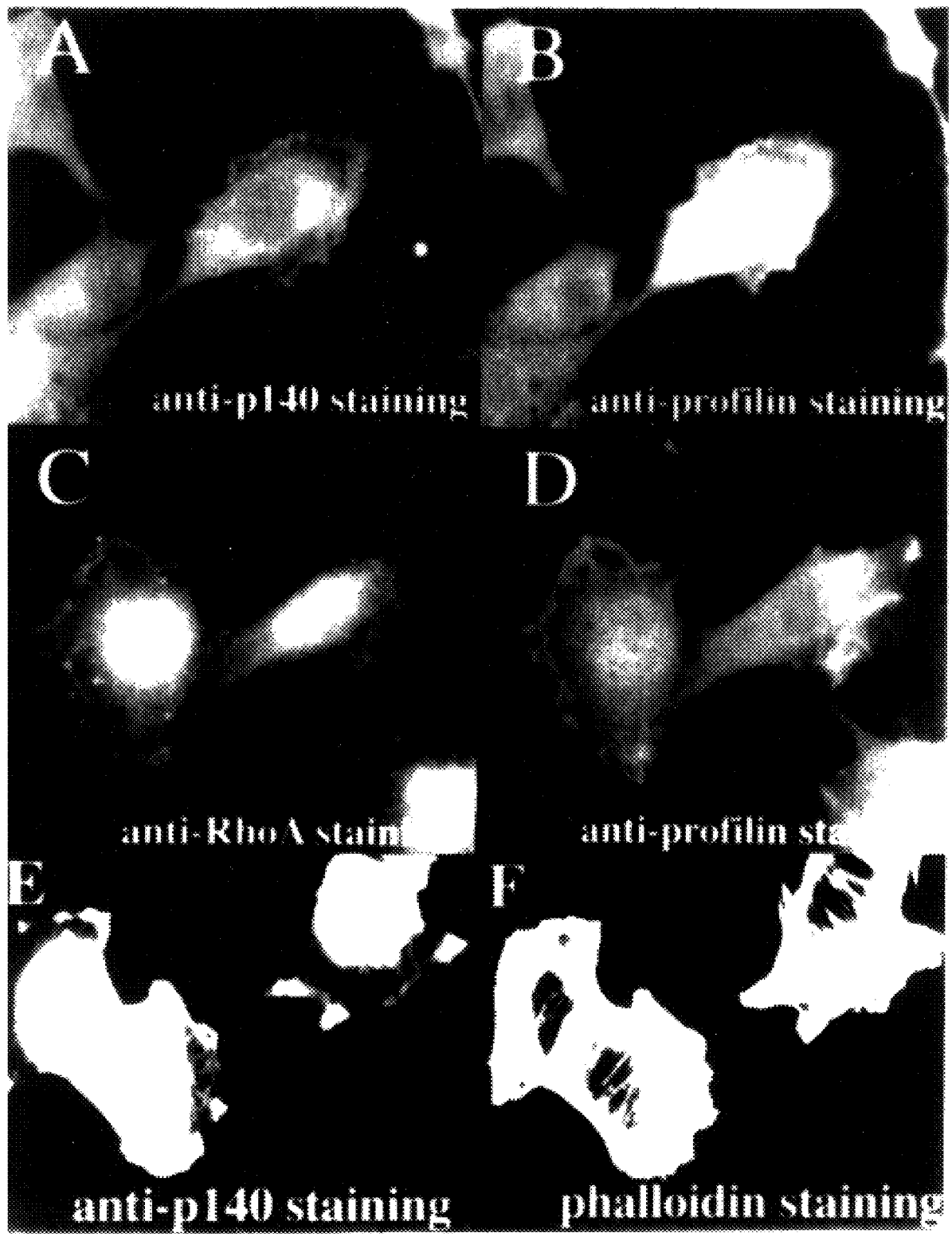

FIG. 9 shows microscopic photographs (photographs of morphology of organism) demonstrating co-localization of RhoA and p140mDia and profilin in membrane ruffles of spreading fibroblasts (HT1080 human fibrosarcoma cells (A–D); Swiss 3T3 mouse fibroblasts (E and F)). The cells were cultured, immobilized, stained simultaneously with anti-p140mDia antibody (A and E), anti-RhoA polyclonal antibody (C) or murine anti-profilin monoclonal antibody (B and D) or rhodamine-phalloidin (F) and photographed using a standard fluorescence microscopy.

Figure 10:
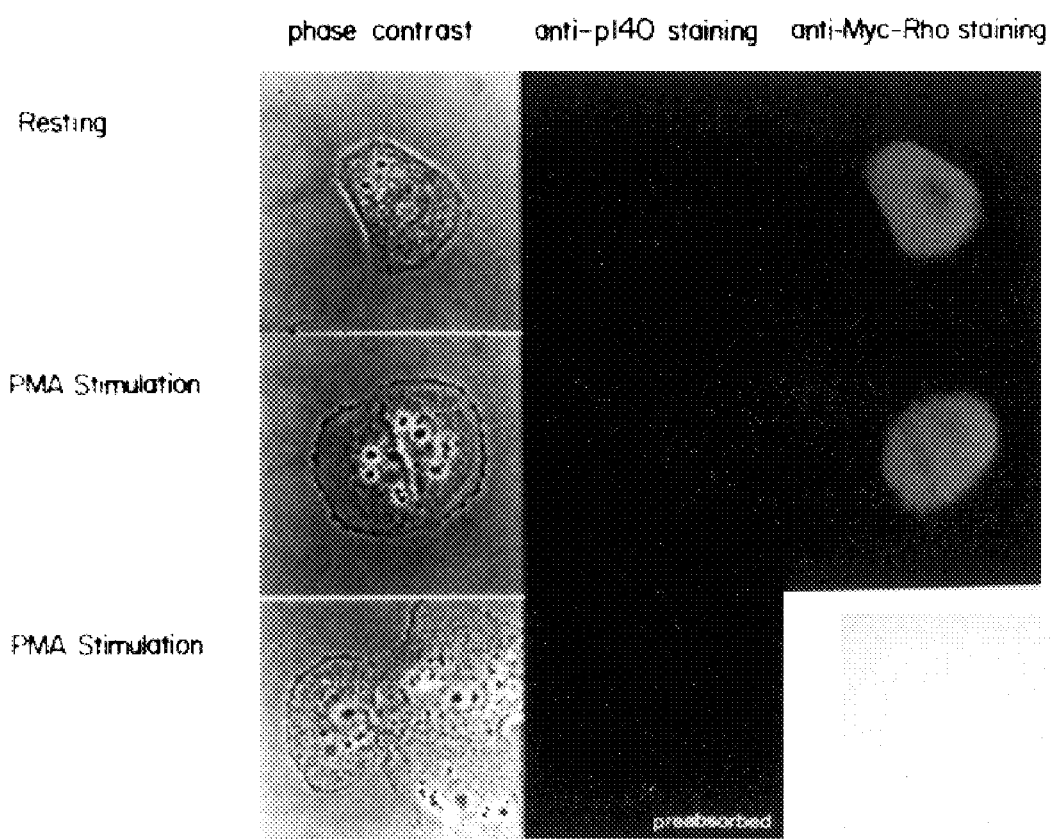

FIG. 10 shows microscopic photographs (photographs of morphology of organism) demonstrating co-localization of myc-labeled RhoA, p140mDia and profilin in membrane ruffles of spreading sMDCK cells stimulated by phorbol myristate acetate (PMA). sMDCK cells in resting phase (A-C) or sMDCK cells stimulated by PMA (D-H) were immobilized and then stained with anti-p140mDia antibody (B, E and H) or monoclonal anti-myc antibody (C and F). Staining using anti-p140mDia antiserum, which was preabsorbed by an excess amount of recombinant peptides, is demonstrated in H. Phase contrast microscopic photographs of each cells are shown in A, D and G. A, B and C refer to the photographs from left to right on the top, D, E and F refer to photographs from left to right in the middle, and G and H refer to photographs from left to right on the bottom.

Figure 11:
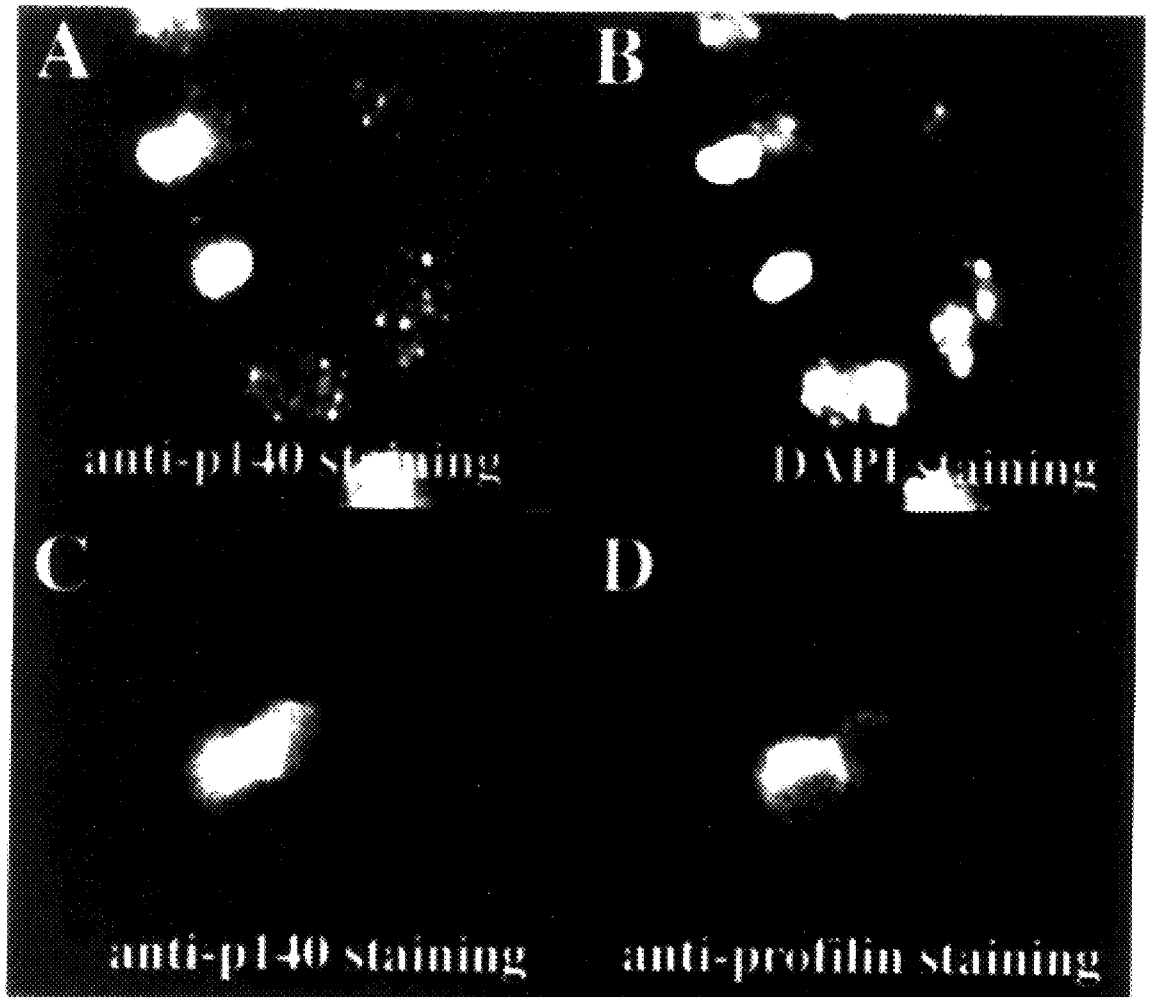

FIG. 11 shows microscopic photographs (photographs of morphology of organism) demonstrating concentration of p140mDia in cleavage furrows of dividing cells (Swiss 3T3 cells in A and B; HeLa cells in C and D). Cells in logarithmic growth phase stained with anti-p140mDia antibody (anti-p140) (A and C) and cells simultaneously stained with DAPI (B) or 2H11 monoclonal anti-profilin antibody (anti-profilin) (D) were photographed using a standard fluorescence microscopy.

Figure 12:
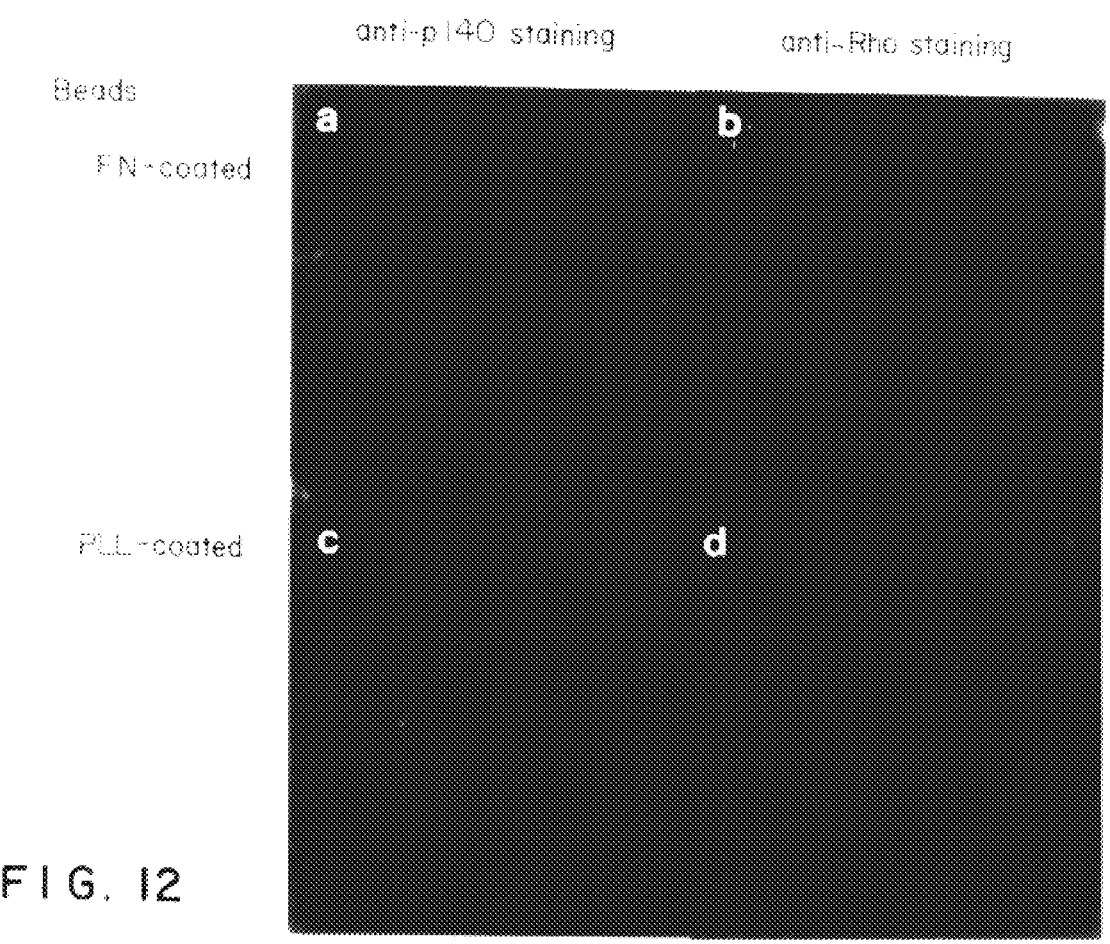

FIG. 12 shows micrographic photographs demonstrating clusters of RhoA and p140mDia which appear around fibronectin-coated beads in a Rho-depending manner. Swiss 3T3 cells incubated for 48 hours were used. Inoculated cells were incubated for 15 minutes with latex beads coated with fibronectin (FN-coated) (a and b) or poly-L-lysine (PLL-coated) (c and d). After fixation, the cells were stained with anti-p140mDia antibody (anti-p140) (a and c) or anti-Rho antibody (anti-Rho) (b and d).

Figure 13:
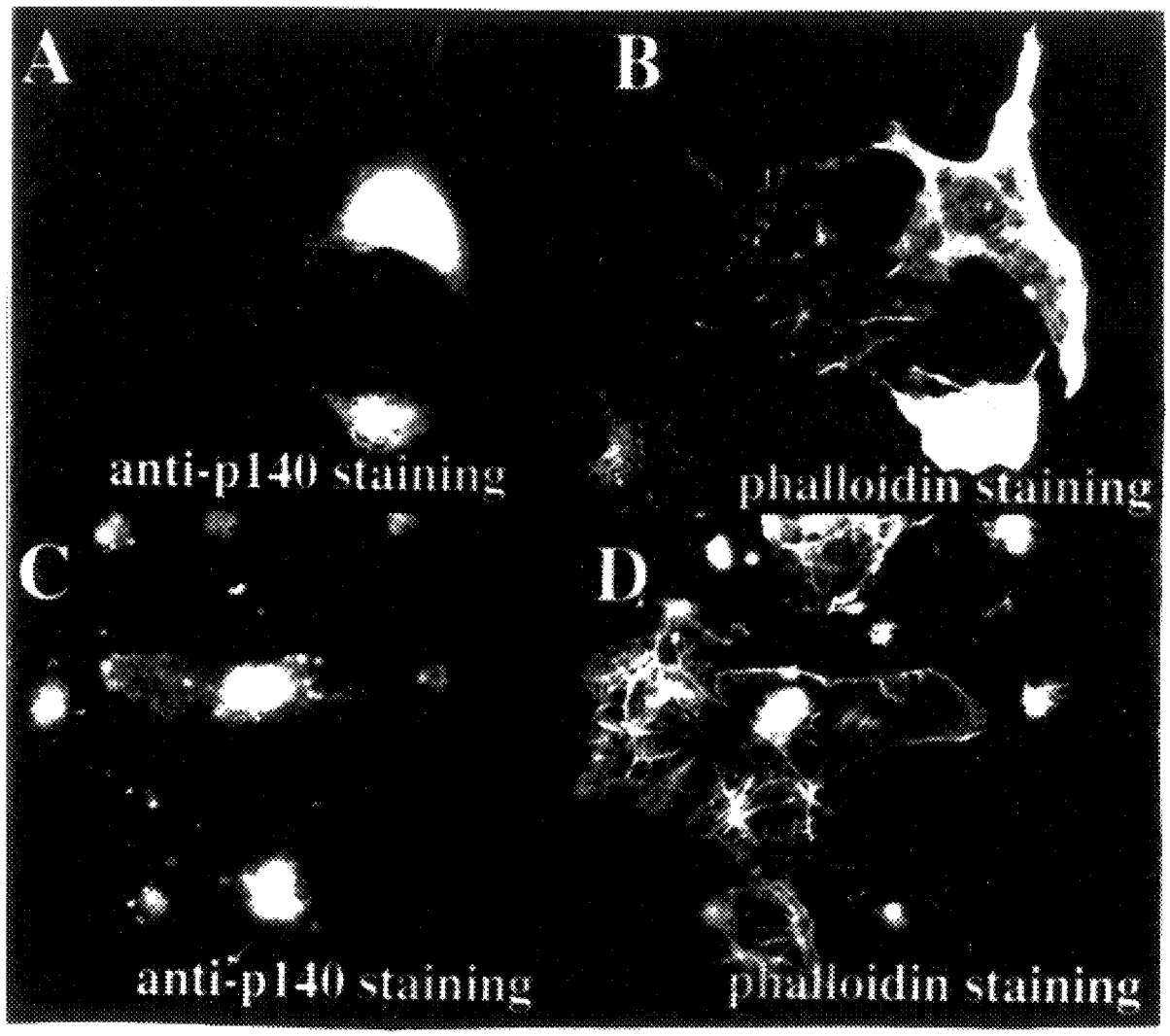

FIG. 13 shows photographs demonstrating temporal expression of p140mDia in COS-7 cells. COS cells were transfected using an expression vector for p140mDia alone (A and B) or an expression vector for a C3 extracellular enzyme alone (C and D). Transfection for the C3 extracellular enzyme was carried out using a C3 extracellular expression vector having FLAG epitope. The resultant cells were fixed and then stained with the anti-p140mDia antibody (anti-p140) alone (A and C) or simultaneously actin was stained with rhodamine-phalloidin (B and D).

Figure 14:
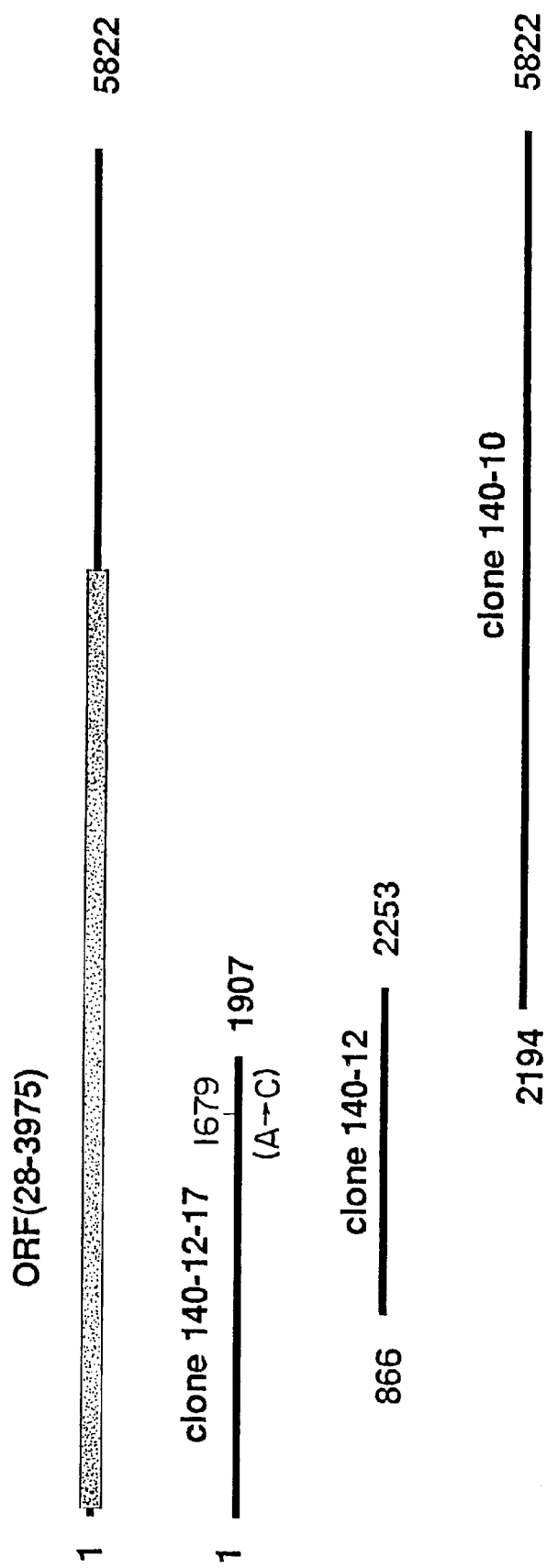

FIG. 14 illustrates the configuration of the whole length of cDNA and individual clone fragments of human mDia cDNA. An open reading frame (ORF) is shown by a thick bar. Numbers are base positions according to SEQ ID No. 4.

FIG. 15 shows comparison of amino acid sequences between human mDia (SEQ ID NO: 3) and murine mDia (SEQ ID NO: 1). Numbers are amino acid numbers according to SEQ ID Nos. 1 and 3. Matched amino acid residues are indicated with vertical lines. In the human mDia sequence, the amino acid residue at 551 designated by "X" is aspartic acid (Asp:D) or alanine (Ala:A). An underline A represents the Rho-binding region.

FIG. 16 is a continuation of FIG. 15 showing comparison of amino acid sequences between human mDia and murine mDia. Numbers are amino acid positions according to SEQ ID Nos. 1 and 3. Matched amino acid residues are indicated with vertical lines. An underline B represents the proline-rich region and an underline C represents the FH-2 region.

Figure 17:
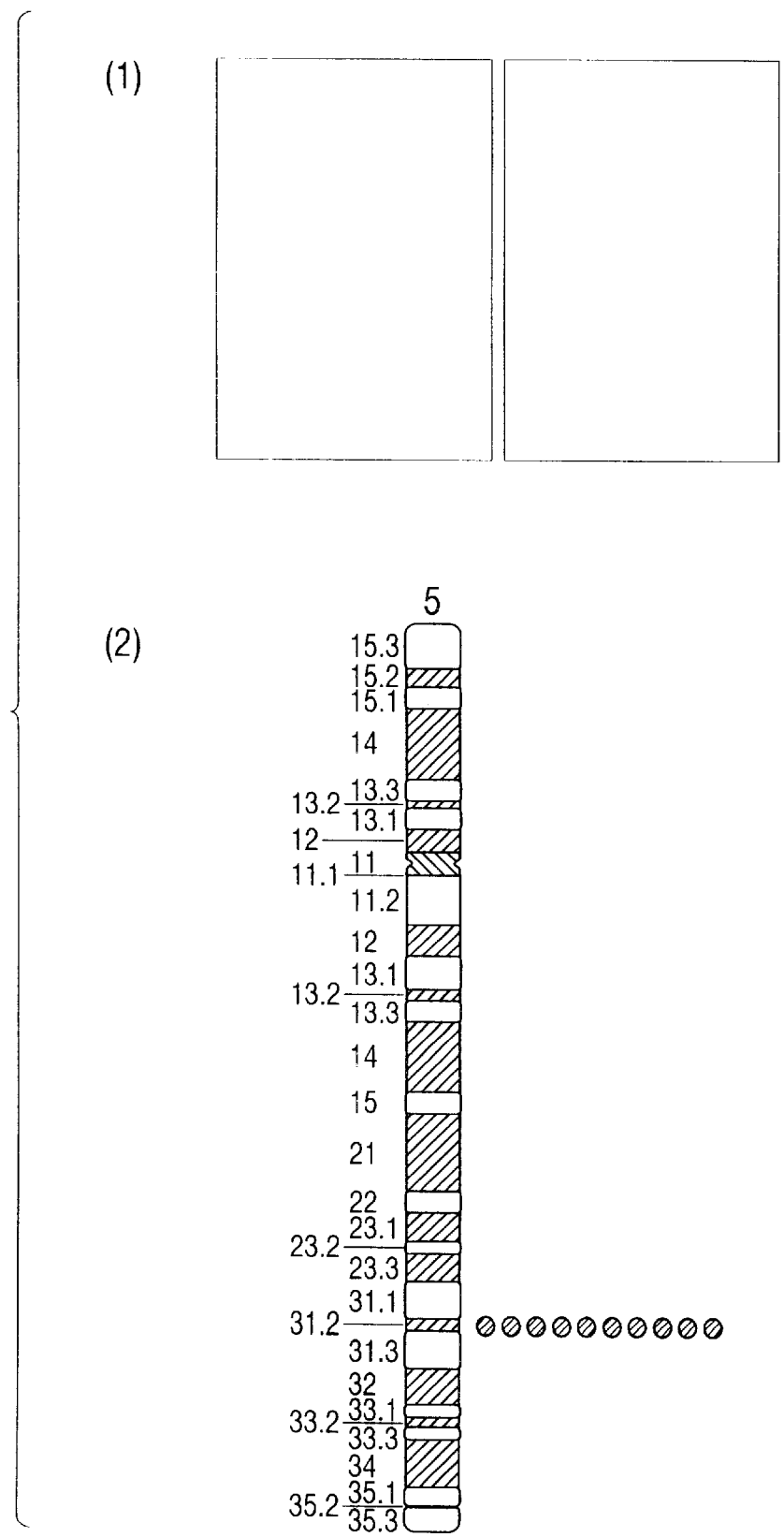

FIG. 17 shows microscopic photographs and a drawing demonstrating the position of the human mDia gene on the chromosome.

(1) shows microscopic photographs (photographs of chromosome) demonstrating results of FISH analysis. A FISH signal on chromosome 5 is shown by an arrow in (A). (B) is the same microscopic photograph in cell dividing phase as A, in which chromosome 5 was stained with DAPI for identification.

(2) is a schematic presentation of the results of (1).

Figure 18:
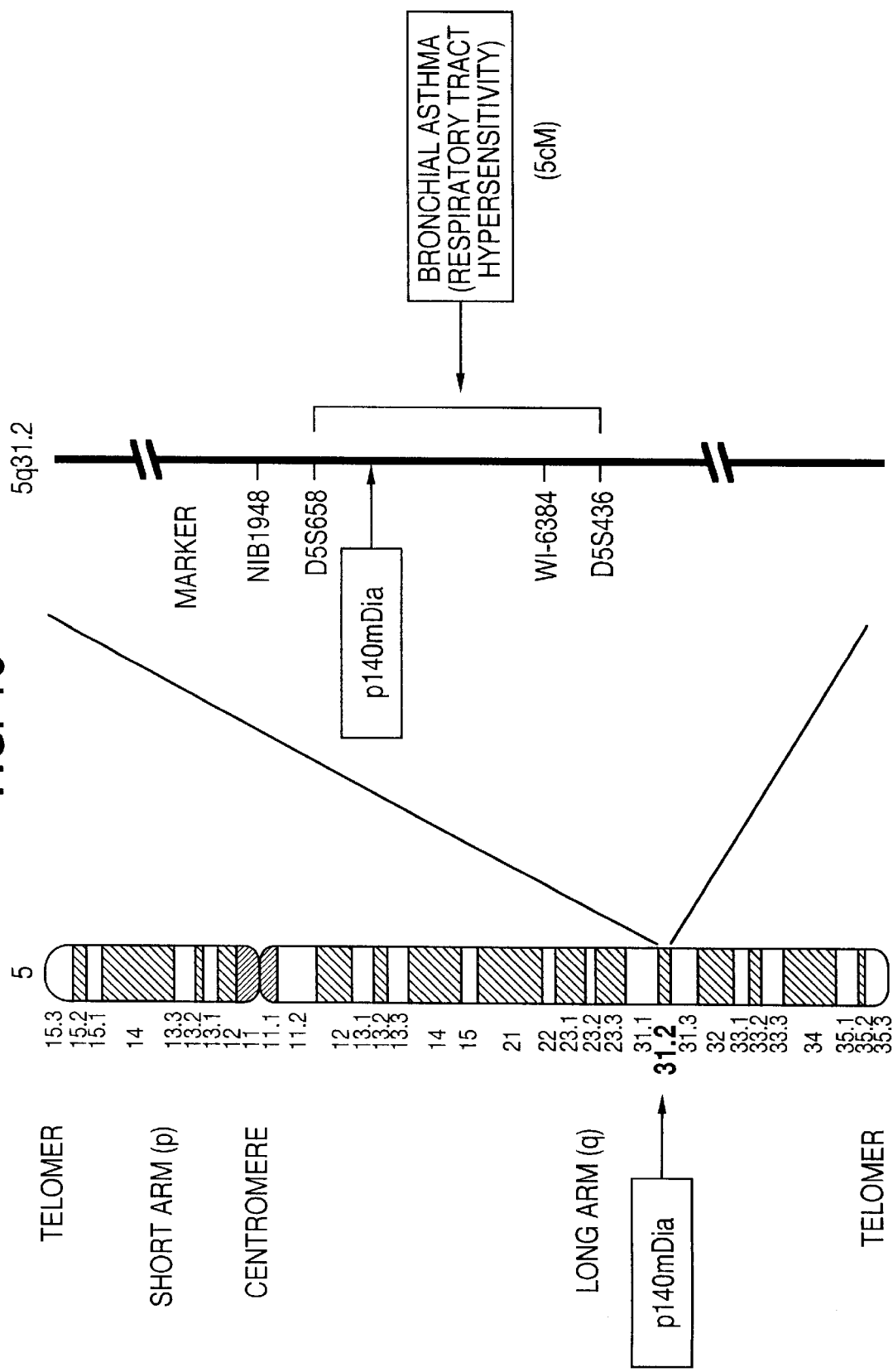

FIG. 18 shows relationship of the position of the human mDia gene (p140mDia) on the chromosome and the area associated with bronchial asthma (respiratory tract hypersensitivity).

DETAILED DESCRIPTION OF THE INVENTION

Definition

The term "amino acid" herein refers to the meaning including either of optical isomers, i.e., an L-isomer and a D-isomer. Thus, the term "peptide" herein refers to the meaning including not only peptides constituted by L-amino acids solely but also peptides comprising D-amino acids partially or totally.

Furthermore, the term "amino acid" herein refers to the meaning including not only twenty α-amino acids which constitute natural proteins but also other α-amino acids as well as β-, γ- and δ-amino acids, non-natural amino acids, and the like. Thus, amino acids with which peptides are substituted or amino acids inserted into peptides as shown below are not restricted to twenty α-amino acids which constitute natural proteins but may be other α-amino acids as well as β-, γ- and δ-amino acids, non-natural amino acids, and the like. Such β-, γ- and δ-amino acids include β-alanine, γ-aminobutyric acid or ornithine. In addition, the amino acids other than those constituting natural proteins or the non-natural amino acids include 3,4-dihydroxyphenylalanine, phenylglycine, cyclohexylglycine, 1,2,3,4-tetrahydroisoquinolin-3-carboxylic acid or nipecotinic acid.

The term "the protein according to the present invention" refers to the meaning including a derivative of the protein.

The term "nucleotide sequence" herein refers to RNA sequences as well as DNA sequences.

A position of mutation in a mutant protein is indicated by referring to the amino acid residue before mutation (one letter), the position of the amino acid to be substituted, and the amino acid residue after mutation (one letter). For example, "human mDia (D551A)" means the amino acid sequence of human mDia, in which the amino acid residue 551, D (Asp: aspartic acid), is substituted by A (Ala: alanine).

Protein

The protein of the present invention is a protein having activated Rho protein binding activity and profilin binding activity or a derivative thereof. Examples of the Rho protein include the RhoA protein, the RhoB protein, the RhoC protein and the RhoG protein.

In the present invention, the term "protein having activated Rho protein binding activity" means a protein which is evaluated by one skilled in the art to bind to the activated Rho protein, e.g., proteins which are evaluated to bind to the activated Rho protein when examined under the same conditions as in Examples 1 and 5.

The protein of the present invention contains the poly-proline region and the FH-2 region in addition to the Rho protein binding region (Examples 2 and 11).

The poly-proline region refers to a region which is characterized by repetition of the sequence IPPPPPLPG or its homologous sequences (motif). The poly-proline region of the mouse mDia protein corresponds to the amino acid sequence 571–737 in SEQ ID NO: 1, and that of human mDia protein corresponds to the amino acid sequence 626–797 in SEQ ID NO: 3. The protein according to the present invention can bind with profilin in its poly-proline region (Example 6).

The FH-2 region refers to a common region which is present relatively close to the C-terminal of the amino acid sequence of formin-related proteins, e.g., *Saccharomyces cerevisiae* Bni1p, mouse formin and *Drosophila cappuccino* and *diaphanous* (Castrillon, D. H. and Wasserman, S. A., Development, 120, 3367–3377, 1994). The FH-2 regions of mouse mDia and human mDia proteins correspond to amino acid sequences 945–1010 in SEQ ID NO: 1 and 1005–1070 in SEQ ID NO: 3, respectively.

Furthermore, the protein according to the present invention is characterized by that it is strongly expressed in the mouse lung, testis, thymus, liver and stomach.

In the present invention, the term "protein having profilin binding activity" means a protein that is evaluated by those skilled in the art to bind to the profilin, for example, proteins which are evaluated to bind to the profilin when examined under the same conditions as in Example 6.

In this specification, the Rho protein includes Rho proteins which have been modified in such a manner that binding between the Rho protein and the protein according to the present invention is not substantially damaged. The modified Rho proteins include an RhoA mutant (RhoA$^{Val14}$) in which the amino acid 14 is substituted by valine.

The protein according to the present invention is derived from humans. Further, the molecular weight of the protein of the present invention is about 150 kDa as measured by SDS-PAGE.

The protein according to the present invention can be obtained by expressing, for example, the cDNA sequence of SEQ ID NO: 4 in a host cell (Examples 4 and 9).

The term "a derivative of a protein" herein includes proteins in which an amino group at an amino terminal (N-terminal) or all or a part of amino groups of side chains of amino acids, and/or a carboxyl group at a carboxyl terminal (C-terminal) or all or a part of carboxyl groups of side chains of amino acids, and/or functional groups other than the amino groups and carboxyl groups of the side chains of the amino acids such as hydrogen, a thiol group or an amido group have been modified by appropriate other substituents. The modification by the appropriate other substituents is carried out in order to, for example, protect functional groups in the protein, improve safety and tissue-translocation of the protein or enhance the protein activity. The derivatives of the proteins include:

(1) proteins in which one or more hydrogen atoms of the amino group at the amino terminal (N-terminal) or a part or all of the amino groups of the side chains of the amino acids are replaced by substituted or unsubstituted alkyl groups (which may be straight chain or branched chain or cyclic chain) such as a methyl group, an ethyl group, a propyl group, an isopropyl group, an isobutyl group, a butyl group, a t-butyl group, a cyclopropyl group, a cyclohexyl group or a benzyl group, substituted or unsubstituted acyl groups such as a formyl group, an acetyl group, a caproyl group, a cyclohexylcarbonyl group, a benzoyl group, a phthaloyl group, a tosyl group, a nicotinoyl group or a piperidincarbonyl group, urethane-type protective groups such as a p-nitrobenzyloxycarbonyl group, a p-methoxybenzyloxycarbonyl group, a p-biphenylisopropyl-oxycarbonyl group or a t-butoxycarbonyl group, or urea-type substituents such as a methylaminocarbonyl group, a phenylcarbonyl group or a cyclohexylaminocarbonyl group;

(2) proteins in which the carboxyl groups at the carboxyl terminal (C-terminal) or a part or all of the side chains of the amino acids are esterified (for example, the hydrogen atom(s) are replaced by methyl, ethyl, isopropyl, cyclohexyl, phenyl, benzyl, t-butyl or 4-picolyl), or amidated (for example, unsubstituted amides or C1–C6 alkylamide such as an methylamide, an ethylamide or an isopropylamide are formed; or (3) proteins in which a part or all of the functional groups other than the amino groups and the carboxyl groups of the side chains of the amino acids such as hydrogen, a thiol group or an amino group are replaced by the substituents described in (1) or a trityl group.

Examples of the protein according to the present invention include proteins comprising the following amino acid sequences:
(a) the amino acid sequence of SEQ ID NO: 3, or
(b) the amino acid sequence of SEQ ID NO: 3 having activated Rho protein binding activity and profilin binding activity wherein one or more amino acids are added and/or into said sequence and/or one or more amino acids of said sequence are substituted and/or deleted.

The terms "addition", "insertion", "substitution" and "deletion" herein refer to those which do not damage the activated Rho protein binding activity or profilin binding activity.

Examples of such substitution include D551A.

According to another aspect of the present invention, a protein which has at least the amino acid sequence 115–312 (Rho protein binding region) and the amino acid sequence 626–797 (profilin binding region) in SEQ ID NO: 3 is provided.

As will be described hereinafter, the gene coding for the protein according to the present invention has been shown to relate to respiratory tract hypersensitivity, bronchial asthma, acute myelocytic leukemia (AML) and myelodysplasia syndrome (MDS). Accordingly, the protein according to the present invention is useful to elucidate the mechanisms of these diseases.

The protein according to the present invention has the activated Rho protein binding activity and profilin binding activity. Furthermore, the Rho protein is closely involved in expression of cellular functions, such as tumorigenesis and metastasis as well as cell morphology, cell motility, cell adhesion and cytokinesis (loc. cit.: Takai, Y. et al.; G. C. Prendergast et al.; Khosravi-Far, R. et al.; R. Qiu et al.; Lebowitz, P. et al.; and Yoshioka, K. et al.). Accordingly, the protein according to the present invention is considered to be useful to elucidate the mechanisms of tumorigenesis and metastasis.

Furthermore, according to Examples hereinafter, the protein of the present invention has been shown to be involved in cellular adhesion. Accordingly, the protein of the present invention is useful to elucidate the mechanisms of invasion and metastasis of cancer cells, aggregation and activation of leukocytes (T lymphocytes, B lymphocyte, neutrophils, eosinophils, basophils, macrophages and the like), aggregation and activation of platelets, and the like.

Furthermore, according to Examples hereinafter, the protein of the present invention has been shown to be involved in cytokinesis (particularly cell proliferation). Accordingly, the protein of the present invention is useful to elucidate the mechanisms of growth of cancer and the like.

Human mDia Locus

It will be explained that the mutation of the human mDia gene (amplification, deletion or reconstitution) or decrease or acceleration of its expression is a risk factor of bronchial asthma and one of the characteristics of AML and MDS as follows:

[1] Bronchial asthma and mDia gene locus

As shown in Example 11 hereinafter, the present inventors precisely determined the position of the human mDia gene on the chromosome using the FISH method and the radiation hybrid (RH) method. As a result of the determination by the FISH method using 3.7 kb human mdia CDNA as a probe, the human mDia gene was mapped at 5q31.2 of the long arm of chromosome 5. As a result of determination by the RH method using a primer pair derived from human mDia CDNA, the human mDia gene was mapped at the site 2.02cR close to the telomere side from NIB1948 between the marker NIB1948 and WI-6384 of the long arm of chromosome 5. The presence of the gene related to respiratory tract hypersensitivity in the area near 5q31.2 was assumed but had not been identified. In the present invention, the inventors have now obtained the evidence that the human mDia gene is the causative gene for the respiratory tract hypersensitivity (Table 1 and FIG. 18).

TABLE 1

Relationship between human mDia locus and respiratory tract hypersensitivity locus

| Gene or marker | Distance from short-arm telomere (cM) | Distance from short-arm telomere (cR) | Mapped disease |
|---|---|---|---|
| NIB1948 | 153 | 444 | No data |
| D5S658 | 154 | 445 | Respiratory tract hypersensitivity |
| Human mDia | No data | 446 | No data |
| WI-6384 | No data | 449 | No data |
| D5S436 | 159 | No data | Respiratory tract hypersensitivity |

Bronchial asthma is a disease characterized by paroxysmal dyspnea, wheezing, coughing and sputum caused by a broad range of respiratory tract constriction. Respiratory tract hypersensitivity is one of the risk factors for bronchial asthma, which means that the respiratory tract shows strong contractive reactions (constriction or obstruction) to various stimuli (for example, stimulation by histamine released by mast cells). Predisposing causes for respiratory tract hypersensitivity are not only extrinsic but also intrinsic(genetic). Recently, Postma et al. carried out a genetic linkage analysis using hypersensitivity to histamine as an index to determine the position of causative gene for respiratory tract hypersensitivity on the chromosome (Postma, D. S., N. Eng. J. Med. 333, 894–900, 1995). Results showed that the responsible gene for respiratory tract hypersensitivity is present at 5q31.2 and linked to the genetic markers D5S658 and D5S436 and markers near them (Table 1 and FIG. 18).

The present inventors have revealed, as hereinafter shown in Example 11, that the human mDia gene exists at 5q31.2, a distance of 2.02 cR from the gene marker NIB1948 to the long arm telomere. An analysis of the order and distance (unit: cM and cR) of the positions of the human mDia gene and other genetic markers using WICGR Genome Analysis Service (http://www-genome.wi.mit.edu/) showed the order: chromosome 5 short arm telomere—centromere—NIB1948—D5S658—human mDia gene—D5S436—long arm telomere. Namely, it was found that the human mDia gene is included in the region in which the gene for the respiratory tract hypersensitivity is mapped (about 5 cM between D5S658 and D5S436) (Table 1 and FIG. 18). This shows that the mutation in the human mDia gene can be a cause or a risk factor for the respiratory tract hypersensitivity.

One possible mechanism of accelerating the respiratory tract hypersensitivity is acceleration of sensitivity in contraction of smooth muscle of the respiratory tract. Namely, in patients of the abovementioned respiratory tract hypersensitivity, the sensitivity in contraction of smooth muscle of the respiratory tract to histamine stimulation is considered to be accelerated.

On the other hand, it is known that the activated Rho protein accelerates the sensitivity in smooth muscle contraction (K. Hirata et al., J. Biol. Chem., 267, 8719–8722, 1992). The mechanism is as follows:

(1) The Rho protein is activated in the cells responding to various stimuli.

(2) The activated Rho protein binds to Rho-kinase to activate it (Matsui, T. et al., EMBO J., 15, 2208–2216, 1996; loc. cit., Leung, T. et al.).

(3) The activated Rho-kinase suppresses myosin light-chain phosphatase (Kimura, K. et al., Science, 273, 245–248, 1996) and at the same time, directly phosphorylates myosin light chains (Amano, M. et al., J. Biol. Chem., 271, 20246–20249, 1996). As a results, phosphorylation level of myosin light chains increases.

(4) Myosin ATPase activity is activated by the phosphorylation, and myosin interacts with actin. As a result, smooth muscle contracts.

Rat Rho-kinase is also called as ROKα (Leung, T. et al., J. Biol. Chem., 270, 29051–29054, 1995). Furthermore, presence of isozymes of Rho-kinase are also known (ROCK or ROCK-I; Ishizaki, T. et al., EMBO J., 15, 1885–1893, 1996; Nakagawa, O. et al., FEBS Lett., 392, 189–193, 1996). ROKα and ROCK are also believed to be involved in acceleration of sensitivity in smooth muscle contraction, like Rho kinase.

Rho kinase (ROKα) and /or ROCK are believed to contract cells by accelerating stress fiber formation and focal contract formation in the cells (Lim, L. et al., Mol. Cell. Biol., 16, 5313–5327, 1996; Amano, M. et al., Science, 275, 1308–1311, 1997). As shown in Example 9 hereinafter, the present inventors have found that when mDia is abundantly expressed, the stress fiber formation by the activated Rho protein is suppressed. Accordingly, the abundantly expressed mDia are considered to inhibit somewhere in the signal transduction pathway from the activated Rho protein to the stress fiber formation and focal adhesion formation via Rho-kinase and/or ROCK. This is because, when the function of the Rho protein or Rho-kinase is inhibited, stress fiber formation and focal adhesion formation are also inhibited (Amano, M. et al., Science, 275, 1308–1311, 1997). Since mDia binds to the activated Rho protein (Examples 1 and 5), it is possible that the abundantly expressed mDia competes for binding to the activated Rho protein with Rho-kinase and/or ROCK.

In contrast, if the human mDia gene has a mutation (e.g., deletion, rearrangement and amino acid substitution) or the level of gene expression decreases, the suppression of stress fiber formation decreases or disappears. Accordingly, the stress fiber formation of smooth muscle in the respiratory tract is considered to be promoted and sensitivity in contraction is accelerated. By all accounts, it is believed that the mDia gene has a mutation (e.g., deletion, rearrangement and amino acid substitution) or the level of gene expression is decreased in respiratory tract hypersensitive patients. Accordingly, the nucleotide sequences and probes of the present invention hereinafter are useful for diagnosis of respiratory tract hypersensitivity or bronchial asthma.

[2] Acute myelocytic leukemia (AML) and myelodysplasia syndrome (MDS)

Deletion of the long arm of chromosome 5 (del(5q)) or deletion of whole chromosome 5 (5q$^-$) is a well recognized characteristic for malignant myelocytic diseases such as acute myelocytic leukemia (AML) and myelodysplasia syndrome (MDS). These mutations are particularly frequent (more than 50%) in leukemia patients who have therapeutic history of chemotherapy. Prognosis for cases with mutations in chromosome 5 is extremely poor.

Recently, the minimum deletion area in chromosome 5 in AML and MDS patients has been determined. According to Horrigan, S. K. et al., Blood, 88, 2665–2670, 1996, deletions of 11 gene markers in the area from D5S806 to D5S805 (D5S816, D5S393, IL9, D5S399, D5S479, AFM350YB1, D5S1372, D5S476, D5S414, D5S500 and D5S658) were recognized in most AML and MDS patients.

On the other hand, the present inventors mapped the human mDia gene at the site 2.02cR close to the telomere side from NIB1948 between the marker NIB1948 and WI-6384 of the long arm of chromosome 5. As a result, the human mDia gene was found to be present very close to D5S658. This means that deletion of the human mDia gene is detected in a high rate in the cells from AML and MDS patients. Accordingly, the nucleotide sequence and probe of the present invention hereinafter described are useful to detect the deletion in chromosome 5 in AML and MDS.

Base Sequence

The present invention provides a base sequence encoding the protein according to the present invention. The typical sequence of this nucleotide sequence has a part or all of the DNA sequence of SEQ ID NO: 4.

The DNA sequence 28–3972 of the SEQ ID NO: 4 corresponds to the open reading frame of human mDia.

When the amino acid sequence of the present invention is given, the base sequence encoding it is easily determined and a variety of base sequences encoding the amino acid sequence described in SEQ ID NO: 3 can be selected. Thus, the base sequence encoding the protein according to the present invention means, in addition to a part or all of the DNA sequence described in SEQ ID NO: 4, another DNA sequence encoding the same amino acid sequence and containing a DNA sequence of a degenerate codon(s), and also includes RNA sequences corresponding to these DNA sequences.

The nucleotide sequence according to the present invention may be naturally occurred or obtained totally by synthesis. It may also be synthesized with a part of a sequence derived from the naturally occurring one. The nucleotide sequence according to the present invention can typically be obtained by screening a chromosome library or a cDNA library in accordance with a conventional manner in the field of genetic engineering, for example, by screening using an appropriate DNA probe obtained based on information of the partial amino acid sequence. The chromosome library and cDNA library are commercially available or obtained as described in Kakizuka, A. et al., 1993, cDNA Library Construction (Stein, C. And Holland, P., ed.), Essential Development Biology: A practical Approach, pp223–232, IRL Press, Oxford. Screening can be carried out using the oligonucleotide corresponding to that shown with thick underline in FIG. 3 (clone 50).

Furthermore, the nucleotide sequence according to the present invention can be obtained by multiplication of a specific region using an appropriate primer using the nucleotide sequence of the chromosome library or the cDNA library as a template.

Examples of the nucleotide sequence encoding the protein according to the present invention include the nucleotide of SEQ ID NO: 4 and a part of the DNA sequence of SEQ ID NO: 4, for example, DNA sequences 28–3972 of SEQ ID NO: 4 (corresponding to the open reading frame), 370–963 (corresponding to the Rho protein binding region) and 1903–2418 (the profilin binding region).

Vector and Host Cells

The present invention provides a vector comprising the nucleotide sequence in such a manner that the vector can be replicable and express the protein encoded by the nucleotide sequence in a host cell. In addition, the present invention provides a host cell transformed by the vector. There is no other restriction to the host-vector system. It may express proteins fused with other proteins. Examples of the fusion protein expression system include those expressing MBP (maltose binding protein), GST (Glutathione-S-transferase), HA (hemagglutinin), myc, fas and the like.

Examples of the vector include plasmid vectors (e.g., expression vectors for prokaryotic cells, yeast, insect cells and animal cells), virus vectors (e.g., retrovirus vectors, adenovirus vectors, adeno-associated virus vectors, herpesvirus vectors, Sendai virus vectors, HIV vectors and baculovirus vector), and liposome vectors (e.g., cationic liposome vectors).

The vector according to the present invention may contain, in addition to the nucleotide sequence according to the present invention, other sequences for regulating the expression (e.g., promoter sequence, terminator sequence and enhancer sequence) or a gene marker for selecting host cells (e.g., neomycin resistance gene and kanamycin resistance gene). In addition, the vector may contain the nucleotide sequence according to the present invention in a repeated form (e.g., in tandem). These nucleotide sequences may be introduced according to the conventional manner, and host cells can be transformed by the vector based on the method conventionally used in the field.

The vector according to the present invention may be constructed based on the procedure and manner which have been conventionally used in the field of genetic engineering.

Furthermore, examples of the host cell include *Escherichia coli*, yeasts, insect cells, animal cells (e.g., COS cells, lymphocytes, fibroblasts, CHO cells, blood cells and tumor cells).

The transformed host cell is cultured in an appropriate medium and the protein according to the present invention can be obtained from the cultured product. Thus, another embodiment of the present invention provide a process for preparing the protein according to the present invention. The culture of the transformed host cell and culture condition may be essentially the same as those for the cell to be used. In addition, the protein according to the present invention may be recovered from the culture medium and purified according to the conventional manner.

Probe/Diagnostic Usage

The present invention provides a nucleotide sequence which is selected from the group consisting of (a) a nucleotide sequence containing a sequence of at least 15 consecutive nucleotide DNA sequences obtained from the sequence of SEQ ID NO: 4, (b) a nucleotide sequence complementary to the nucleotide sequence (a), and (c) a nucleotide sequence which hybridizes with the nucleotide sequence (a) or (b) under stringent conditions.

Examples of the sequence as mentioned above include DNA sequences of SEQ ID NO: 4, e.g., 2194–5822 (clone 140-10), 866–2253 (Clone 140-12), 1–1907 (except that A at 1679 is substituted by C) (Clone 140-12-17), 1274–1293, 866–1293 (Example 10), 1226–1244 (Example 11 (2)) and 1327–1347, and those complementary to those sequences.

The DNA sequence of SEQ ID NO: 5 is a chain complementary to the DNA sequence of SEQ ID NO: 4. Accordingly, examples of the chain complementary to the DNA sequences include DNA sequences in SEQ ID NO: 5, i.e., 1–3629, 3570–4957, 3916–5822 (except that C at 4144 is substituted by A), 4530–4549 (Example 10), 4530–4957, 4579–4597 and 4476–4496 (Example 11 (2)).

The present invention also provides a nucleotide sequence which is selected from the group consisting of:

(d) a nucleotide sequence containing a sequence of at least consecutive 15 nucleotide DNA sequences obtained from the sequence of SEQ ID NO: 6, (e) a nucleotide sequence complementary to the nucleotide sequence (d), and (f) a nucleotide sequence which hybridizes with the nucleotide sequence (d) or (e) under stringent conditions.

Examples of the sequences as mentioned above include the DNA sequence of 95–727 (corresponding to an intron) of SEQ ID NO: 6 and the complementary sequence to this sequence.

The DNA sequence of SEQ ID NO: 7 is a chain complementary to the DNA sequence of SEQ ID NO: 6. Accordingly, the chain complementary to the DNA sequence is the DNA sequence 29–661 of SEQ ID NO: 7.

The sequence of SEQ ID NO: 6 is a DNA sequence derived from human genome, containing an intron. The intron exists between 1319 and 1320 of the nucleotide sequence of SEQ ID NO: 4.

In the present invention, the term "stringent conditions" in hybridization are defined as hybridization conditions in Southern hybridization method (Example 10), PCR method (Examples 10 and 11 (2)) and FISH method (Example 11 (1)), in which the abovementioned sequences are used as probes or primers.

According to the present invention, a probe comprising the nucleotide sequence as mentioned above and a label is provided. A detectable label can be selected from those known by one skilled in the art, which include substances that interact (e.g., avidin and biotin), enzymes (e.g., peroxidase and alkaline phosphatase), radioactive isotopes (e.g., $^{32}P$ and $^{35}S$), fluorescent agents (e.g., FITC and europium) and antigens (e.g., digoxigenin).

The labeling method may be selected depending on labeling molecules, which include nick translation, chemical (or photochemical) cross linkage, oligonucleotide chemical synthesis and chelation.

The method of labeling the nucleotide sequence may be selected depending on labeling molecules; the label can be detected using fluorescence-, enzyme- or ferritin-labeled antibodies, avidin-FITC, β-galactosidase, gold colloid or the like.

As mentioned above, the human mDia gene is revealed to be associated with respiratory tract hypersensitivity, bronchial asthma, acute myelocytic leukemia (AML) and myelodysplasia syndrome (MDS). Accordingly, diagnoses of these diseases (including presymptomatic diagnoses such as prenatal diagnoses) can be done using the nucleotide sequence and probe of the present invention (hereinafter referred to simply as the probe).

According to the present invention, a diagnostic drug containing the probe as mentioned above is provided.

The diagnosis can be carried out by taking a gene sample (e.g., chromosomes and genomic DNAs) from a patient and measuring the level of hybridization between the probe and the gene sample. Examples of a method to measure the level of hybridization includes FISH method, Southern hybridization method and PCA method.

(1) FISH method

In the FISH method, a specimen, in which a chromosome of cells (e.g., lymphocytes) isolated from humans are fixed, and the abovementioned probes are hybridized and the mDia gene on the chromosome is mapped. In normal human cells, the mDia gene is mapped exclusively at a site of q31.2 on the long arm of a pair of chromosome 5 (5q31.2) as described in Examples hereinafter.

On the other hand, in cells of patients of respiratory tract hypersensitivity, bronchial asthma, acute myelocytic leukemia (AML) and myelodysplasia syndrome (MDS), chromosomes with no signal for the mDia gene (in which the mDia gene is deleted), chromosomes with a strong signal for the mDia gene (in which the mDia gene is amplified) or chromosomes with a signal for the mDia gene at a site other than 5q31.2 (in which the mDia gene is translocated) are detected. Such mutations (e.g., deletion, amplification and translocation) are characteristic changes in either of the diseases as mentioned above. Accordingly, the diseases as mentioned above can be diagnosed by measuring the level of hybridization using the FISH method or detecting the position of the mDia gene on the chromosome.

The FISH method can be carried out, for example, under the conditions described in Example 11 (1). Practically, hybridization is carried out under optimal conditions selected from a range of those conditions depending on the purpose of the experiment, kinds of probe, DNA to be hybridized with or the like. Conditions for the FISH method can be referred to Heng, H. H. Q. et al., Proc. Natl. Acad. Sci. USA, 89, 9509–9503, 1992; Heng, H. H. Q. and Tsui, L.C., In situ hybridization protocols: Methods in Molecular Biology, Choo, K. H. A. (Ed.), Humana Press, New Jersey, pp.109–122, 1994; Choo, K. H. A., ed., Methods in Molecular Biology: In situ hybridization protocols. (Choo, K. H. A., ed.), pp. 35–49, 1994, Humana Press, Clifton, N.J., USA and Gerhard, D. S. et al., Proc. Natl. Acad. Sci. USA, 78, 3755–3759, 1981.

(2) Southern Hybridization Method

In Southern hybridization method (J. Sambrook et al., Molecular Cloning 2nd ed., Ch. 9, 1989, Cold Spring Harbor laboratory Press, New York), a genomic DNA is isolated from isolated human cells (e.g., lymphocytes) and digested with appropriate restriction enzymes, after which a digested DNA fragment is isolated by gel electrophoresis. Next, the isolated DNA fragment is transferred to a filter for hybridization with the abovementioned probe on the filter. Patients with the abovementioned diseases are generally divided into a group with no hybridization, a group with a lower level of hybridization (i.e., a part or all of the mDia gene is deleted) or a group with increased level of hybridization (i.e., the mDia gene is amplified) as compared to healthy subjects, or a group exhibiting the DNA fragment hybridized with the probe, which is different in size and numbers from those of healthy subjects.

Furthermore, the position of the mDia gene on the chromosome of a patient can be detected by combining Southern hybridization with a human/rodent somatic cell hybrid panel (Macera, M. J. et al., Genomics, 13, 829–831, 1992). In this way, the presence or absence of deletion or translocation of the mDia gene of patients can be detected (see Example 11 (2)).

Such mutations (e.g., deletion, amplification and translocation) are characteristic changes in one of the diseases as mentioned above. Accordingly, the diseases as mentioned above can be diagnosed by measuring the pattern of bands to hybridize with the probe by Southern hybridization.

When a DNA fragment is used as a probe, Southern hybridization can be carried out using 2–6×SSC (a 0.15 M sodium chloride solution, a 0.015 M sodium citrate solution) at 65–70° C.

Practically, hybridization is carried out by selecting the optimal conditions depending on the purpose of the experiment, kinds of probe, DNA to be hybridized with or the like. Conditions for the hybridization can be found in "Manual for Gene Manipulation" edited by Yasuyuki Takagi, Kodansha, Tokyo, Japan, 1982.

(3) PCR method

Diagnosis can also be carried out by using PCR method (Saiki, R. K. et al., Science, 239, 487–491, 1988) in stead of Southern hybridization, in which a gene sample (e.g., chromosomes, genomic DNAs, poly (A)$^+$ RNAs or mRNAs) is taken from a patient and the degree of amplification of gene fragment or the degree of mRNA expression is measured. In PCA method (including RT-PCR method), a pair of primers (primer pair) is hybridized with DNA or RNA which act as a template, and the resultant DNA fragment is amplified using polymerase or reverse transcriptase. A pair of the probes as mentioned above can be used as a primer for PCR. PCR method can be carried out using the gene sample taken from the patient as a template using such primer pair to amplify whole or a part of the mDia gene or mDia mRNA. Amplified DNA is analyzed by electrophoresis, nucleotide sequence analysis or the like, to detect the mutations (e.g., deletion, amplification, recombination, translocation and base substitution) of the mDia gene or the degree of expression of mDia mRNA.

For example, when a gene sample taken from a patient which has mDia gene deletion is applied to the PCR method, the specified region is not amplified. Accordingly, the deletion of the mDia gene can be detected by examining the absence or presence of amplified fragments.

For example, when a gene sample of a patient which has the amplification of the mDia gene is applied to PCR method, the specified region is amplified in a larger scale as compared to healthy samples. Accordingly, acceleration of amplification of the mDia gene or expression of mDia mRNA can be detected by examining the amount of amplified fragments.

PCR method can be performed, for example, using Takara LA tag kit ver. 2 with 30 cycles of reaction: at 98° C. for 10 seconds, at 55° C. for 30 seconds and at 72° C. for 3 minutes. Practically, PCR method is carried out by selecting the optimal conditions depending on the purpose of the experiment, kinds of the probe, the gene sample to be used as a template or the like. Conditions for PCR amplification can be found in Saiki, R. K. et al., Science 239, 487–491, 1988.

As mentioned above, the mutations in the mDia gene are characteristic to respiratory tract hypersensitivity, bronchial asthma, acute myelocytic leukemia (AML) and myelodysplasia syndrome (MDS). Accordingly, the diagnostic drug according to the present invention can be used for these diseases.

According to the present invention, a method for detecting mutations in the mDia gene of a mammal wherein the probe according to the present invention hybridizes with a gene sample obtained from the mammal and the degree of the hybridization is measured. This detection method can be carried out in the same manner as described for the use of the diagnostic drug.

Screening Method

The present invention provides a method for screening a material which inhibits the binding between the activated Rho protein and the protein according to the present invention, comprising:

(1) placing a material to be screened in a screening system containing the activated Rho protein and the protein according to the present invention, and (2) measuring the degree of inhibition of the binding between the activated Rho protein and the protein of the present invention.

The present invention also provides a method for screening a material which inhibits the binding between profilin and the protein of the present invention, comprising:

(1) placing a material to be screened in a screening system containing profilin and the protein according to the present invention, and (2) measuring the degree of inhibition of the binding between profilin and the protein of the present invention.

Examples of the method for "measuring degree of inhibition of binding" include a method to measure by immunoblotting using antibody to the protein of the present invention, the two hybrid system (M. Kawabata, Experimental Medicine, 13, 2111–2120, 1995; A. B. Vojetk et al., Cell 74, 205–214, 1993), a method to measure using an overlay assay (Ishizaki, T. et al., EMBO J., 15, 1885–1893, 1996), a method to measure using a protein translated in vitro (Shibata, H. et al., FEBS Lett., 385, 221–224, 1996) and a method to measure the binding in a cell-free system (Amano, M., et al., Science, 271, 648–650, 1996). For example, the degree of the binding inhibition can be measured as described in Examples 1, 5 and 6.

The term "material which inhibits the binding" in the present invention refers to a material which is recognized to inhibit the binding by those skilled in the art; such that no binding with the activated Rho protein or profilin is recognized under the same conditions as described in Example 1, 5 or 6.

The term "measuring degree of inhibition of binding" includes measuring the presence or absence of the binding. The term "screening" includes assay.

The screening system may be either a cell system or a cell-free system. Examples of the cell system include yeast cells, COS cells, *Escherichia coli*, insect cells, nematode cells, lymphocytes, fibroblasts, CHO cells, blood cells and tumor cells.

The material to be screened includes, but is not limited to, for example, peptides, analogues of peptides, microorganism cultures and organic compounds.

EXAMPLE

Example 1

Screening of RhoA Binding Peptide Fragment Using Yeast Two Hybrid System

A novel Rho binding protein was screened by a yeast two hybrid system using $N^{19}$-RhoAΔC ($Rho^{Asn19}$ truncated at $Ala^{181}$ of the C terminal) fused to LexA DNA binding protein as a bait. The yeast two hybrid system was carried out according to the method described previously (Vojtek, A. et al., Cell, 74, 205–214, 1993; Modaule, P. et al., FEBS Lett., 377, 243–248, 1995; Watanabe, G. et al., Science, 271, 645–648, 1996; Reid, T. et al., J. Biol. Chem., 271, 13556–13560, 1996).

Plasmids pBTM116 and pVP16 (Vojtek, A. et al., Cell, 74, 205–214, 1993) used in the two hybrid system were obtained from Stan Hollenberg, Rolf Sternglanz, Stan Fields and Paul Bartel. pBTM-RhoA (pBTMl16 containing cDNA coding for RhoA) was prepared by the method described previously (Watanabe, G. et al., Science, 271, 645–648, 1996). In order to induce a mutation at $Val^{14}$ or $Asn^{19}$ on RhoA, BamHI-EcoRV fragment of pGEX-RhoA coding for the N terminal of RhoA was inserted into pBluescript (Staratagene), and the mutation was induced by the method of Kunkel (Kunkel, T., Proc. Natl. Acad. Sci. USA, 82, 488–492, 1985). Next, corresponding wild-type fragments of pGEX-RhoA (Morii, N. et al., J. Biol. Chem., 268, 27160–27163, 1993) were substituted by individual mutation-induced fragments to construct pGEX-$V^{14}$RhoA and pGEX-$N^{19}$RhoA.

BamHI-EcoRI fragments encoding the total length of coding region of the mutant RhoA were excised from pGEX-$V^{14}$RhoA and pGEX-$N^{19}$RhoA and inserted in pBTM116 to obtain pBTM-$V^{14}$RhoA and pBTM-$N^{19}$RhoA. pBTM116 plasmids with an insertion of C-terminal deletion at $Ala^{181}$ (pBTM-$V^{14}$RhoAΔC and pBTM-$N^{19}$RhoAΔC) were prepared according to the method described previously (Reid, T. et al., J. Biol. Chem., 1966).

Yeast strain L40 (MATa trp1 leu2 his3 LYS::lexA-HIS3 URA3::lexA-lacZ) (Vojtek, A. et al., Cell, 74, 205–214, 1993) harboring pBTM-$N^{19}$RhoAΔC was transformed with pVP16 (Vojtek, A. et al., Cell, 74, 205–214, 1993) fused with a mouse embryo cDNA library (Kakizuka, A. et al., 1993, cDNA Library Construction (edited by Stein, C. and Holland, P.), Essential Developmental Biology: A Practical Approach, 223–232, IRL Press, Oxford). Initial transformation efficiency was $2.2 \times 10^7$, which replicated 7 times during incubation for 6 hours before plating on HIS(−) plates. Among $1.5 \times 10^8$ transformants, 978 clones were isolated as His+ and lacZ positive, and 220 clones were subjected to segregation to eliminate the bait plasmid. Interactions with other proteins were evaluated by mating with yeast strain AMR70 harboring various test baits. Of the 220 clones, 55 clones exhibited positive LacZ activity with $N^{19}$-RhoAΔC, but negative with lamin used as a negative control. All the 55 clones isolated in this manner had a cDNA insert of the same size and results of sequencing some of the clones showed that they have the same nucleotide sequence.

These clones were mated with AMR70 having LexA fused to various RhoA mutants. All of them bound strongly with $RhoA^{Val14}$, weakly with $RhoA^{Asn19}$ and almost negligibly with the wild-type RhoA, although they retained strong binding with $N^{19}$-RhoAΔC or the wild-type RhoAΔC. A similar result was confirmed by the experiment described below.

To examine the specificity of the interaction in the two hybrid system, a pVP16 plasmid recovered from yeast clone 50 (pVP-cl.50) was co-transformed into L40 strain with pBTM116 plasmids having CDNA of various proteins. The interaction was examined by the LacZ assay. Plasmids used for the experiment were prepared as previously described, i.e., pBTM-RhoAΔC and pBTM-lamin (Watanabe, G. et al., Science, 271, 645–648, 1966) and pBTM-Rac and pBTM-Cdc42H (Reid, T. et al., J. Biol. Chem., 271, 13556–13560, 1996).

Figure 1:
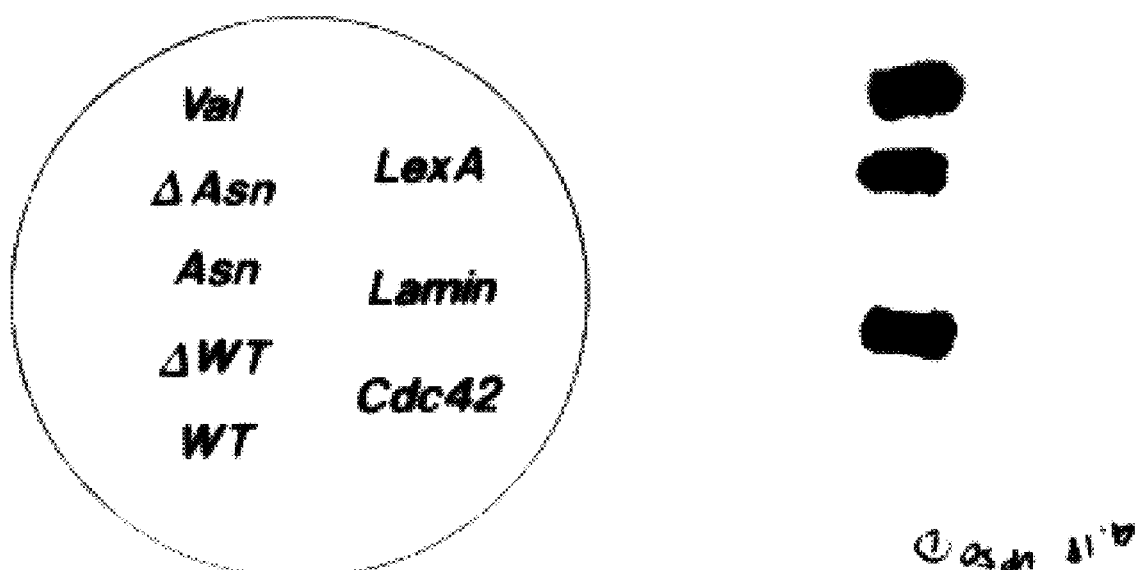

As a result, the specificity of binding was confirmed by co-transforming strain L40 with a plasmid recovered from a representative clone (clone 50) and various LexA-mutant RhoA fusion constructs (FIG. 1). Namely, it was revealed that when strain L40 was co-transformed with the plasmid recovered from clone 50 and a LexA-Rac fusion construct or a LexA-Cdc42H fusion construct, the peptide encoded by this clone specifically binds to neither Rac nor Cdc42H. These results indicate that the peptide encoded by this clone specifically binds to RhoA.

Example 2
Cloning of Full Length of cDNA of Mouse mDia

To obtain the full length of the coding sequence, the present inventors screened two mouse brain libraries (936309 in ramdaZAP II (Stratagene) and ML3000a in λgt-10 (Clontech)) using the 0.6 Kbp cDNA insert obtained from clone 50 (the $^{32}$P-labeled 0.6 Kbp cDNA insert of pVP-cl.50) as a probe, and then screened a mouse embryo library (Kakizuka, A. et al., 1993, cDNA Library Construction (Stein, C. and Holland, P. ed.), Essential Developmental Biology: A Practical Approach, 223–232, IRL Press, Oxford) using the two cDNA fragments obtained from the first screening as probes.

Six overlapping clones were isolated by this procedure (FIG. 2). One positive clone (clone 502) and two positive clones (clones 503 and 504) were obtained from the former and latter libraries respectively. Clones E51, E52 and E73 were isolated from the mouse embryo library using the 5' site of 504 and the 3' site of 503 as probes.

Nucleotide sequences of these clones were determined using the dideoxy chain termination method. The complete cDNA sequence determined from these clones contained an open reading frame of 3,765 bp, which encoded a protein of 1,255 amino acids having a calculated molecular weight of 139,336 Da (FIG. 3). The initial cDNA obtained from clone 50 codes for the sequence of 198 amino acids (amino acid sequence 63–260) containing the Rho binding domain in the N-terminal. In the middle of the molecule between amino acids 571 and 737, there is a proline-rich region that is characterized by 14 repeats of IPPPPPLPG (G/S/A/V) SEQ ID NO: 8 or homologous sequences. In comparison of the extrapolated amino acid sequence with other sequences in the data bases, several homologous proteins are identified, all of which share the proline-rich region (FIG. 4). These proteins belong to the family of formin-like molecules, which share two homologous regions, i.e., a proline-rich FH-1 region and an FH-2 region. An FH-2 region was also found in the extrapolated sequence between amino acids 945 and 1010. A protein most homologous to the present sequence is *Drosophila diaphanous*, a protein known to be required for cytokinesis, which showed about 30% homology in the N-terminal side of the proline-rich region and about 39% homology in the C-terminal side. This protein also showed about 32% and 57% homology to the identified protein in the putative Rho-binding domain and the FH-2 region respectively. Based on these results, the protein identified by the inventors was concluded to be a mammalian homolog of *Drosophila diaphanous* and designated as mDia (mammalian Diaphanous, hereinafter referred to as "mDia").

mDia also showed significant homology in the entire region to *Saccharomyces cerevisiae* Bni1p, which is involved in yeast cell budding. On the other hand, mDia showed homology only in the C-terminal half to formin and *Drosophila cappuccino*. While the Rho-binding domain was mapped in the N-terminal region in mDia, as described above, no sequence analogous to the Rho-binding domain was found in formin or cappuccino. These results suggest that these proteins (containing no Rho-binding domain, i.e., formin and cappuccino) exert similar functions in the cells as the identified protein but only mDia, diaphanous and Bni1p exert their functions in a Rho-dependent manner.

Example 3
Search for Tissues that Express mDia

Northern blot analysis was carried out to search for tissues that express mDia. Poly (A)$^+$ RNA was prepared from various tissues of adult mice using oligo-dT latex beads (Pharmacia Biotech Inc.) according to the standard procedure (Sambrook, J. et al., 1989, Molecular Cloning: Laboratory Manual, 2nd Edition, Cold Spring Harbor Laboratory Press, Cold Spring Harbor). 6 μg each of poly (A)$^+$ RNA were separated on a 1.0% agarose gel containing 2.1% formaldehyde and transferred to a Biodyne A filter (Pall BioSuport). The filter was then hybridized with a $^{32}$P-labeled 0.6 Kbp cDNA fragment of cl.50. Finally, the filter was washed with 0.4×SSC and 0.1% SDS at 65° C., and subjected to autoradiography.

As a result, a major 6.3 kb transcript was ubiquitously detected in all tissues examined but highly expressed in the lung, testis, thymus, liver and stomach. An additional 5 kb transcript was found in the testis and lung (FIG. 5).

Example 4
Preparation of Anti-mDia Antibody

In order to examine localization of mDia in the cell and its binding with other proteins, a peptide encoded by clone 50 cDNA (including amino acid sequence 63–260 in SEQ ID NO: 1) was expressed as a His-tagged protein and an antibody specific to mDia was obtained by producing the antibody against this peptide. The experiment was carried out as follows:

cl.50 cDNA was ligated into vectors pQE11 (QIAGEN) and pGEX-3X (Pharmacia) using the BamHI and EcoRI sites of pVP-cl.50 flanking the CDNA insert. His6-tagged cl.50 was expressed in *Escherichia coli* strain JM109 and purified using Ni-NTA resin (QIAGEN) according to the manufacturer's protocol. The purified protein was mixed with Freund's adjuvant and injected into rabbits. The antibody was affinity-purified using GST-cl.50 fusion protein immobilized on nitrocellulose membranes according to the method described in Reid, T. et al., J. Biol. Chem., 271, 13556–13560, 1992. In more detail, inclusion bodies containing GST-cl.50 were isolated from *E. coli*, solubilized in Laemmli's buffer, separated by SDS-PAGE, and transferred to the nitrocellulose membranes. A band of GST-cl.50 was excised as a strip, and antibodies absorbed to this strip were eluted at 4 C successively with 100 mM glycine-HCl buffer (pH 2.3), 100 mM monoethanolamine buffer (pH 11.5) and 100 mM glycine-HCl buffer containing 10% 1,4-dioxane (pH 2.5). The eluates were immediately neutralized with 0.25 volume of 250 mM sodium phosphate buffer (pH 8.8 for the first and third eluates and pH 7.0 for the second eluate). These eluates were combined and used as the affinity-purified antibody, AP50. For a control immunofluorescence study, the antibody-depleted AP50 was prepared by incubating an aliquot of AP50 successively with 5 pieces of GST-cl.50 blotted membranes.

The specificity of the polyclonal antibody obtained was verified by its reactivity with a protein having an expected molecular weight of 50 kDa and its degradation products found in *E. coli* lysates after IPTG induction (lanes 1 and 2 in FIG. 6). AP50 antibody detected a single protein of about 160 kDa in Swiss 3T3 cell lysates. This protein apparently corresponds to endogenous mDia (lanes 3 and 4 in FIG. 6).

Example 5
Detection of Binding of Rho Protein and mDia in Vitro

Binding of wild-type Rho family low-molecular-weight G proteins and natural mDia was examined in vitro using AP50 antibody. The experiment was carried out as follows:

GDP- or GTP-binding type GST-small G proteins (GST-Rho, Rac and Cdc42H) were prepared according to the method described previously (Reid, T. et al., J. Biol. Chem., 271, 13556–13560, 1992). Approximately 1×10$^7$ of Swiss 3T3 confluent cells were collected and ultrasonically disrupted (5 seconds, 4 times) in 3.2 ml of buffer A [10 mM Mes (pH 6.5), 150 mM NaCl, 2 mM MgCl$_2$, 0.5 mM EDTA, 0.5% Triton X-100, 5 mM DTT, 1 mM PMSF, 5 ug/ml leupeptin]. The ultrasonicated homogenate was centrifuged at 10,000 g for 20 minutes and the resultant supernatant was saved. Loading of each nucleotide was carried out by incubating 10 μM GST-low-molecular-weight G protein with 1 mM nucleotide according to the method described previously (Ishizaki, T. et al., EMBO J., 15, 1885–1893, 1996). Next, a 1/10 volume of the supernatant was incubated with 400 pmol of each GST-low-molecular-weight G protein loaded with either GTPγS or GDP. After incubation at 30° C. for 30 minutes, 5 μl of glutathione-Sepharose were added and the admixture was incubated at 4° C. for 1 hour. Immunocomplex was recovered by centrifugation, washed twice with 1 ml of buffer A and then boiled in Laemmli's sample buffer. The solubilized extract was subjected to SDS-PAGE and separated proteins were transferred to a PVDF membrane. Immunoblotting was performed with anti cl.50 antiserum AP50 according to the procedure described previously (Kumagai, N. et al., J. Biol. Chem., 268, 4535–24538).

Results are shown in FIG. 7. mDia was precipitated only with GTPγS-bound Rho but not with its GDP-bound Rho or by either GTPγS-bound Rac or Cdc42. These results support the results in the two hybrid system, and show that mDia selectively binds to the activated form of Rho.

Example 6
Detection of Binding of Profilin with mDia in Vitro

It has been shown that mDia has repetitive poly-proline stretches while profilin binds to poly-L-proline sequences. Therefore, the present inventors examined whether profilin binds to mDia and whether this binding is dependent on Rho. The experiment was carried out as follows:

Human platelet profilin was purified using poly-L-proline affinity chromatography as described previously (Janmey, P. A., Ann. Rev. Physiol., 56, 169–191, 1994). Briefly, 250 mg of poly-L-proline (PLP, MW=12,000, Sigma) was coupled to CNBr-activated Sepharose 4B (Pharmacia). Washed human platelets were prepared from the buffy coat fraction of 100 units blood as described previously (Ishizaki, T. et al., EMBO J., 15, 1885–1893, 1996). The platelets were ultrasonically disrupted in 200 ml of extraction buffer [20 mM Tris (pH 7.4), 150 mM KCl, 0.2 mM ATP, 1 mM DTT, 1 mM PMSF] plus 50 mM benzamidine and 1 mg/ml aprotinin. After centrifugation at 100,000×g for 1 hour, the supernatant was applied to a PLP-Sepharose column. The column was washed with 4 M urea and then profilin was eluted with 7 M urea. The homogenous preparation of profilin was obtained by this method. Next, 0.96 mg of profilin was conjugated with 1 ml of NHS-activated Sepharose (Pharmacia) according to the manufacturer's protocol to obtain immobilized profilin beads. As a control, bovine serum albumin was similarly coupled to NHS-activated Sepharose.

Confluent Swiss 3T3 cells obtained from twelve 6-cm culture plates were solubilized in 2.4 ml of buffer C. The resultant lysate was centrifuged at 10,000×g for 10 minutes to recover the supernatant. A 1/10 volume aliquot of the supernatant was incubated with or without GST-low-molecular-weight G proteins, free GTPγS or free GDP. 20 μl of immobilized profilin were also added. The resultant admixture was incubated at 25° C. for 30 minutes and then the beads were spun down at 1,000×g for 2 minutes. The supernatant was saved and the beads were washed once with 100 μl of buffer C containing 300 mM NaCl in place of 100 mM NaCl. 50 μl of Laemmli's sample buffer were added to the beads, and a 1/10 volume aliquot of the supernatant was mixed with a 1/5 volume of 5×Laemmli buffer. The samples were boiled, applied to SDS-PAGE and transferred to a nitrocellulose membrane. Immunoblotting was carried out as described above except that the detection was performed using ECL system (Amersham).

Results are shown in FIG. 8. mDia in Swiss 3T3 cell lysate was nearly quantitatively precipitated by the addition of profilin-agarose, while no precipitation was observed with BSA-agarose. This binding, however, was not affected either by the addition of exogenous RhoA or by the addition of GTPγS.

Example 7
Co-localization of RhoA, mDia and Profilin in Membrane Ruffles of Spreading Locomotive Cells and in Cleavage Furrows of Dividing Cells Distribution of mDia, profilin and endogenous Rho and their possible co-localization in vivo were studied in HT1080 cultured human fibrosarcoma cells, Swiss 3T3 cells, sMDCK2 cells, which stably express myc-tagged RhoA (K. Takaishi, K. et al., Oncogene, 11, 39–48, 1995), or HeLa cells by fluorescence microscopy using antibodies specific to each protein.

Cells were grown in Dulbecco's modified Eagle's medium (DMEM) supplemented with 10% fetal calf serum (FCS). HT1080 cells were seeded at a density of 5×10$^4$ cells/35-mm dish, incubated overnight and subjected to the analysis. For the analysis of sMDCK2 cells, cells were seeded on a glass coverslip at a density of 1×10$^4$ cells/35-mm dish in DMEM containing 10% FCA, and incubated for 16 hours. The medium was then changed to DMEM without FCS and the incubation was continued for 24 hours. Serum-starved cells were stimulated with or without 1×10$^7$ M phorbol ester (phorbol myristate acetate (PMA)) at 37° C. for 15 minutes and fixed.

For indirect immunofluorescence, the cells were fixed in phosphate-buffered saline (PBS) containing 3.7% paraformaldehyde at room temperature for 20 minutes, and then permeabilized by treating with PBS containing 0.2% Triton-X 100 for 10 minutes. After washing several times with PBS, the cells were incubated in buffer B [20 mM Tris (pH 7.4), 50 mM NaCl] containing 5% BSA at room temperature for more than 30 minutes. For mDia staining, the cells were incubated with a 1:10 dilution of A50 in a blocking solution at room temperature for 1 hour and then washed 3 times with buffer B containing 0.1% Triton X-100. Next, cells were stained Cy2-labeled goat anti-rabbit IgG antibody (Amersham Life Science). For actin staining, rhodamine phalloidin (Molecular Probe) was added with the second antibody at a 1:200 dilution. For Myc-epitope staining, 9E10 monoclonal anti-Myc antibody was added at a concentration of 10 μg/ml with AP50 in the first incubation. Rhodamine anti-mouse IgG antibody was then added at a 1:50 dilution for detection.

Results were as follows: The majority of fluorescence obtained by anti-mDia antibody was localized in the thicker part of the HT1080 cells, i.e., in the cytoplasm of the perinuclear region. However, prominent fluorescence was also observed in peripheral regions known to be highly motile, e.g., leading lamellas and membrane ruffles of spreading locomotive cells (FIG. 9A). Marked lack of mDia staining was observed between the perinuclear cytoplasm region and the leading edges. Binding of mDia with focal adhesions and stress fibers was not observed. A similar pattern of distribution was observed in cultured Swiss 3T3 cells (FIG. 9E).

Double immunofluorescence microscopic observation using monoclonal anti-profilin antibody (2H11) detected accumulation of profilin in the perinuclear cytoplasmic region of HT1080 cells and expanded lamellas and veils, which overlapped with distribution of mDia (FIG. 9B). This profilin distribution was consistent with the previous study with rat fibroblasts (Buβ, F. et al., Cell Mot. Cytoskeleton, 22, 51–61, 1992). Interestingly, double immunofluorescence study with the profilin antibody and polyclonal anti-RhoA antibody revealed that a part of endogenous RhoA also accumulates with profilin in the membrane veils of the motile cells (FIGS. 9C and 9D). These findings suggested that mDia, profilin and RhoA co-localized in the highly motile structures of the cells. Furthermore, distribution of mDia was examined in Swiss 3T3 cells and compared with distribution of F-actin. mDia was also localized in these cells in the extended lamellas where actin ribs were well developed (FIG. 9E and 9F).

Co-localization of mDia, profilin and RhoA was also demonstrated in sMDCK cells that stably express myc-tagged RhoA and extend membranes in response to phorbol ester (Takaishi, K. et al., Oncogene, 11, 39–48, 1995). As shown in FIG. 10, both Myc-RhoA and mDia were present rather homogeneously in the cytoplasm in the thicker parts of the resting cells. After stimulation by PMA for 2 minutes, a part of Myc-RhoA was moved to the peripheral membrane ruffles where mDia was co-localized. A part of profilin also was revealed to move to the membrane ruffles to co-localize with RhoA. Since membrane extension of these cells induced by phorbol ester is known to occur in a Rho-dependent manner (Takaishi, K. et al., Oncogene, 11, 39–48, 1995), these results suggest that the recruitments of mDia and profilin are also Rho-dependent.

In cells in interphase, the majority of mDia was present in the cytoplasm, some being translocated to the plasma membrane of spreading edges. On the other hand, in mitotic cells, no mDia localization was observed before the cytoplasmic division. At this time, a part of mDia was concentrated in the plasma membrane in the cleavage furrows and appeared as a ring-like structure (FIGS. 11A and 11C). This concentration disappeared at the end of the cytokinesis and the staining moved to the surrounding area of the plasma membrane. No staining was observed at the sustained intercellular bridges connecting daughter cells. During these processes, profilin showed a staining pattern almost overlapping with mDia (FIG. 11D).

Example 8
RhoA and mDia Cluster Around Fibronectin (FN)-coated Beads

Recent studies indicate that both Rho activation and ligation of extracellular matrix proteins with integrin are required for cell spreading and adhesion to substrates (Hotchin, N. A. and Hall, A., J. Cell Biol., 131, 1857–1865, 1995) and that integrin ligation by beads coated with either fibronectin or anti-integrin antibody recruited Rho to the plasma membrane right under the beads (Burbelo, P. et al., J. Biol. Chem., 270, 30919–30926, 1995). The present inventors, therefore, examined whether mDia was also recruited with Rho to the plasma membrane by these beads, and if so, whether this recruitment was depend on the activated Rho.

Polystyrene latex beads (average diameter: 11.9 μm, Sigma) were coated with 50 μg/ml human fibronectin (Collaborative Research, Inc.) or 100 pg/ml poly-L-lysine (Sigma) as described (Grinnel and Geiger, Exp. Cell Res., 162, 449–461, 1986). Trypsinized Swiss 3T3 cells were plated on the poly-lysine-coated glass slips and allowed to bind to the slips in DMEM containing 10% FCS at 37° C. for 2 hours. Each different type of beads were then placed onto the cells. After incubation at 37° C. for 15 minutes, the cells were fixed. mDia was stained as described above. For immunostaining of endogenous RhoA, a rabbit anti-RhoA antibody (Santa Cruz) was used at a 1:40 dilution. The antibody was visualized using Cy2-labeled goat anti-rabbit IgG antibody as described above.

Results are as follows: First, it was confirmed that the endogenous Rho was accumulated beneath the fibronectin (FN)-coated beads (FIG. 12b) but not beneath the poly-lysine-coated beads (FIG. 12d). Under this condition, mDia was also recruited beneath the FN-coated beads and a ring-like accumulation was observed around the beads (FIG. 12a). From the abovementioned results (i.e., accumulations of both Rho and mDia) and the fact that these accumulations were inhibited when the cells were treated in advance with C3 extracellular enzymes, these recruitments were revealed to be dependent on the activated Rho (data not shown). Similarly, it was observed that profilin was also co-localized with mDia and Rho (data not shown).

Example 9
Induction of Actin Polymerization by Excessive Expression of mDia

In order to examine functions of mDia, cDNA of mDia (amino acid sequence of 1–1255 in SEQ ID NO: 1) and/or cDNA of other proteins were temporally expressed in COS7 cells and the resultant cells were fixed and stained with anti-mDia antibody according to the method described previously (Ishizaki, T. et al., EMBO J., 15, 1885–1893, 1996).

Cells were subjected for transfection for 40 hours and then stained with anti-mDia antibody. The cells were well stained and thus expression of mDia was confirmed. Stain was observed in the perinucleotide region in the non-transfected cells. In contrast, the transfected cells were evenly stained to give sharp outlines of the cells, which showed that mDia was localized in the whole plasma membrane when this molecule was excessively expressed (FIG. 13A). When stained with phalloidin, stress fibers disappeared and actin staining was enhanced in accord with the plasma membrane of the cells (FIG. 13B), which suggested that mDia was translocated to the membrane where actin polymerization was induced. When mDia was expressed with the C3 extracellular enzyme, more marked results were obtained. Namely, when the cells were transfected with the C3 extracellular enzyme gene alone, almost all of the actin fibers in the cells disappeared and the cells became round (FIGS. 13C and 13D). When transfected with the mDia gene and the C3 extracellular enzyme gene, the infected cells retained their shape and the fibrous staining, similar to that observed in the cells transfected with the mDia gene alone, was observed (data not shown).

Furthermore, mDia was co-expressed along with Rho$^{Val14}$ or wild-type Rho. When Rho$^{Val14}$ or wild-type Rho was expressed alone, stress fibers and induction of contraction were observed. However, when mDia was co-expressed with Rho$^{Val14}$ or wild-type Rho, the abovementioned characteristics for mDia expression (i.e., disappearance of stress fibers and actin staining in accord with plasma membrane of the cells) were more apparent than those manifested in the case of single Rho expression (i.e., stress fibers or induction of contraction), and stress fibers or induction of contraction was hardly observed (data not shown). These results shows that when expressed excessively, mdia translocates to the plasma membrane spontaneously. Namely, the results suggests that mDia translocates independently from the actin polymerization by Rho protein.

Example 10

Cloning of Human mDia cDNA

PCR primers (SEQ ID NO: 9) [5'-TGG AGG TAC AGG TAT ACC ACC ACC ACC TCC-3' (base sequence of 2127–2156 in SEQ ID NO: 2) and a sequence complementary to (SEQ ID NO: 10) 5'-GTT CTC ACT CTT ACG CAG CTC TTC GCA TGC-3' (base sequence of 2929–2958 in SEQ ID NO: 2)] were prepared based on the part of the base sequence of mouse mDia that is structurally conserved as compared with the base sequence of yeast BNI1. Using these primers, a partial cDNA fragment of human mDia was amplified using 2 μl of QUICK-CLONE cDNA Human Brain (Clontech) as a template and Takara LA PCR kit Ver. 2 (Takara). The reaction was cycled at 98° C. for 10 seconds, 55° C. for 30 seconds and 72° C. for 30 minutes for 30 cycles. The amplified cDNA fragment was subcloned to pBluescript II SK-to determine the base sequence and confirmed to be the human mDia gene. Using this partial cDNA fragment of human mDia as a probe, a human brain λ ZAP cDNA library (1.0×10$^6$ plaques) was screened. This screening was carried out according to the method described previously (J. Sambrook et al., Molecular Cloning: A Laboratory Manual, Cold Spring Harbor Laboratory, Cold Spring Harbor, N.Y., 1989). Prehybridization was carried out at 65° C. for 3 hours in 6×SSC, 10× Denhardt's solution, 1% SDS and 200 μg/ml. The human mDia cDNA fragment was labeled with $^{32}$P using Primie-it II RandomPrimer Labeling Kit (Stratagene), and hybridization was carried out using this probe at 65° C. overnight. Washing was carried out 4 times at room temperature using 2×SSC and 0.1% SDS. As a result, two human mDia cDNA clones (clone 140-10 (base sequence 2194–5822 in SEQ ID NO: 4) and clone 140-12 (base sequence 866–2253 in SEQ ID NO: 4) were obtained.

In order to obtain a missing part of the 5'-terminal region of the human mDia cDNA, a human brain λgt10 cDNA library (1.0×10$^6$ plaques) (Clontech) was screened. This screening was carried out according to the method described previously (J. Sambrook et al., Molecular Cloning: A Laboratory Manual, Cold Spring Harbor Laboratory, Cold Spring Harbor, N.Y., 1989). Prehybridization was carried out at 65° C. for 3 hours in 6×SSC, 10× Denhardt's solution, 1% SDS and 200 mg/ml. In the 5'-terminal region of clone 140-12, the human mDia partial cDNA sequence (base sequence 866–1293 in SEQ ID NO: 4) was PCR-amplified using primers (SEQ ID NO: 11) 5'-CCG TCC CTT CAG GTC ATA GG-3' (corresponding to base sequence 4530–4549 in SEQ ID NO: 5 and base sequence 1274–1293 in SEQ ID NO: 4) and (SEQ ID NO: 12) 5'-CAG GAA ACA GCT ATG ACC ATG-3' (a part of pBluescript II SK-). This cDNA fragment was labeled with $^{32}$P using Primie-it II RandomPrimer Labeling Kit, and hybridization was carried out using this probe at 65° C. overnight. Washing was carried out 4 times at room temperature using 2×SSC and 0.1% SDS. As a result, one cDNA clone [clone 140-12-17 (base sequence 1–1907 in SEQ ID NO: 4, except that A at position 1679 is replaced by C)] that cover the 5'-terminal region was obtained. Alignment deletions were made using Double-stranded Nested Deletion Kit (Pharmacia) to determine base sequences of individual clones using 377 DNA sequencer (ABI).

The base sequence of the full length of the human mDia cDNA was determined as shown in SEQ ID NO: 4, except that the base at position 1679 was C in clone 140-12-17 while it was A in clone 140-12. This difference in the base sequence is believed to be due to the difference in origin of the clones. The cDNA library from which clone 140-12 was cloned (Clontech) is different in its origin from the cDNA library from which clone 140-12-17 was cloned (Stratagene). Thus, of base sequences coding for human mDia, one has base A at position 1679 and the other has base C at position 1679. Such difference in base sequences is considered to reflect polymorphism in humans.

As a result of this difference in base sequences, it is revealed that there are two kinds of human mDia having two different sequences. Namely, one has Asp at position 551 of amino acid sequence (i.e., amino acid sequences of SEQ ID NO: 3 and SEQ ID NO: 4) and the other has Ala at position 551 of the amino acid sequence [human mDia (D551A)].

Deduced human mDia protein consisted of 1315 amino acid residues and an extrapolated molecular weight was about 145 kDa. It showed 87% homology to mouse mDia (Example 2). The Rho binding domain of mouse mDia (amino acid sequence 63–260 in SEQ ID NO: 1) corresponded to amino acid sequence 115–312 of human mDia and they were 94% identical. The proline-rich region (amino acid sequence 571–737 in SEQ ID NO: 1) and the FH-2 region (amino acid sequence 945–1010 in SEQ ID NO: 1) of mouse mDia correspond to amino acid sequence 626–797 and amino acid sequence 1005–1070 of human mDia and their identity was 73% and 94% respectively. FIG. 14 shows contig maps of individual clones obtained. Amino acid sequences of human mDia and mouse mDia are aligned for comparison in FIGS. 15 and 16.

Example 11

Determination of the Position of the Human mDia Gene on Chromosomes (1) FISH analysis In order to find the position of the the human mDia gene on chromosomes, a fluorescence in situ hybridization (FISH) analysis was carried out. Lymphocytes isolated from human blood were incubated in an α-minimum essential medium (MEM) supplemented with 10% fetal calf serum and phytohemagglutinin (PHA) at 37° C. for 68–72 hours. Cultured lymphocytes were treated with BrdU (0.18 mg/ml, Sigma) for synchronization. Synchronized lymphocytes were washed 3 times with a serum-free medium and then incubated in an α-MEM supplemented with thymidine (2.5 mg/ml, Sigma) at 37° C. for 6 hours. The resulting cells were collected to prepare slides. cDNA clone 140-10 containing the 5'-terminal sequence of the human mDia gene (base sequence 2194–5822 in SEQ ID NO: 4) was biotinylated using BioNick labeling kit (Heng et al., 1992). Detection of FISH was carried out according to the method described previously (Heng et al., 1992 and Heng and Tuji, 1993). The slides were heated at 55° C. for 1 hour. After treating with RNase, the slides were treated with 2×SSC containing 70% formaldehyde for 2 minutes for denaturation and then dehydrated at 70° C. with ethanol. The probe was denatured in a hybridization solution (50% formamide, 10% dextran sulphate) at 75° C. for 5 minutes. The probe was placed on the denatured chromosome slides and allowed to stand at 37° C. overnight. The slide was washed 3 times with 50% formamide and 2×SSC for 3 minutes and then 3 times with 2×SSC at 43° C. for 3 minutes to detect signals. FISH signals and DAPI band patterns were photographed separately and the positions on the chromosomes were determined by laying one photograph over another.

As a result of the FISH analysis, a signal was detected on one particular pair of chromosomes in 92 out of 100 dividing cells. Based on the DAPI band, the signal was found to be present on the long arm of chromosome 5. The position on the chromosome was determined more precisely by a thorough examination of 10 photographs (FIG. 17). It was revealed that the human mDia gene was present at 31.2 on the long arm of chromosome 5.

(2) Determination of the position of the human mDia gene on chromosomes using Radiation Panel In order to determine the position of the human mDia gene on chromosomes, an analysis was carried out using GeneBridge 4 Radiation Hybrid Panel (Research Genetics). PCR amplification was carried out for the determination using 25 ng of DNAs as a template using primers specific to the human mDia gene (SEQ ID NO: 13), 5'-ATA TGA GAG TGC AAC TAA A-3' (base sequence 1226–1244 in SEQ ID NO: 4) and (SEQ ID NO: 14) 5'-GAG AAT CTG AAA GAC TTC ATT-3' (base sequence 4476–4496 in SEQ ID NO: 5, corresponding to base sequence 1327–1347 in SEQ ID NO: 4). PCR was carried out using Takara LA PCR kit Ver. 2 for 30 cycles at 98° C. for 10 seconds, 55° C. for 30 seconds and 72° C. for 1 minute. Results of 0.7% agarose gel electrophoresis of the reaction solution showed that a 755 bp DNA fragment specific to the human mDia (base sequence of SEQ ID NO: 6 including a 633 bp intron sequence) was amplified. The intron is present between base 1319 and 1320 of SEQ ID NO: 4. The results were analyzed using WI/MIT Radiation Hybrid Mapper (http: //www-genome.wi.mit.edu/cgi-/bin/contig/rhmapper. p1#instructions). As a result, the human mDia gene was revealed to be present at the position 2.02cR from NIB1948 to the telomere side.

The whole contents of Japanese Patent Application No. 242701/1996 filed on Aug. 26, 1996 and Japanese Patent Application No. 90170/1997 filed on Mar. 25, 1997 are incorporated hereinto by reference.

What is claimed is:

1. An isolated protein comprising the amino acid sequence of SEQ ID NO: 3.

2. An isolated protein comprising the amino acid sequence 115 to 312 in SEQ ID NO: 3 and the amino acid sequence 626 to 797 in SEQ ID NO: 3.

3. An isolated protein comprising a modified amino acid sequence of SEQ ID NO: 3, wherein the amino acid modification is the substitution of the Asp residue at position 551 with an Ala residue.

* * * * *

UNITED STATES PATENT AND TRADEMARK OFFICE
CERTIFICATE OF CORRECTION

PATENT NO. : 6,111,072
DATED : August 29, 2000
INVENTOR(S) : Shuh NARUMIYA, et al.

It is certified that error appears in the above-identified patent and that said Letters Patent is hereby corrected as shown below:

front cover [30] Foreign Application Priority Data delete "August 26, 1996 [JP] 9-242701" and insert --August 26, 1996 [JP] 8-242701--.

Signed and Sealed this

Fifteenth Day of May, 2001

Attest:

NICHOLAS P. GODICI

Attesting Officer

Acting Director of the United States Patent and Trademark Office

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
      (A) LENGTH: 1255 amino acids
      (B) TYPE: amino acid
      (D) TOPOLOGY: linear (ii) MOLECULE TYPE: protein (xi) SEQUENCE DESCRIPTION: SEQ ID NO:1:

```
Met Glu Pro Ser Gly Gly Gly Leu Gly Pro Gly Arg Gly Thr Arg Asp
 1               5                  10                  15

Lys Lys Lys Gly Arg Ser Pro Asp Glu Leu Pro Ala Thr Gly Gly Asp
            20                  25                  30

Gly Gly Lys His Lys Lys Phe Leu Glu Arg Phe Thr Ser Met Arg Ile
        35                  40                  45

Lys Lys Glu Lys Glu Lys Pro Asn Ser Ala His Arg Asn Ser Ser Ala
    50                  55                  60

Ser Tyr Gly Asp Asp Pro Thr Ala Gln Ser Leu Gln Asp Ile Ser Asp
 65                  70                  75                  80

Glu Gln Val Leu Val Leu Phe Glu Gln Met Leu Val Asp Met Asn Leu
                85                  90                  95

Asn Glu Glu Lys Gln Gln Pro Leu Arg Glu Lys Asp Ile Val Ile Lys
            100                 105                 110

Arg Glu Met Val Ser Gln Tyr Leu His Thr Ser Lys Ala Gly Met Asn
        115                 120                 125

Gln Lys Glu Ser Ser Arg Ser Ala Met Met Tyr Ile Gln Glu Leu Arg
    130                 135                 140

Ser Gly Leu Arg Asp Met His Leu Leu Ser Cys Leu Glu Ser Leu Arg
145                 150                 155                 160

Val Ser Leu Asn Asn Pro Val Ser Trp Val Gln Thr Phe Gly Ala
                165                 170                 175

Glu Gly Leu Ala Ser Leu Leu Asp Ile Leu Lys Arg Leu His Asp Glu
            180                 185                 190

Lys Glu Glu Thr Ser Gly Asn Tyr Asp Ser Arg Asn Gln His Glu Ile
        195                 200                 205
```

```
Ile Arg Cys Leu Lys Ala Phe Met Asn Asn Lys Phe Gly Ile Lys Thr
    210                 215                 220
Met Leu Glu Thr Glu Glu Gly Ile Leu Leu Val Arg Ala Met Asp
225                 230                 235                 240
Pro Ala Val Pro Asn Met Met Ile Asp Ala Ala Lys Leu Leu Ser Ala
                245                 250                 255
Leu Cys Ile Leu Pro Gln Pro Glu Asp Met Asn Glu Arg Val Leu Glu
            260                 265                 270
Ala Met Thr Glu Arg Ala Glu Met Asp Glu Val Glu Arg Phe Gln Pro
        275                 280                 285
Leu Leu Asp Gly Leu Lys Ser Gly Thr Ser Ile Ala Leu Lys Val Gly
    290                 295                 300
Cys Leu Gln Leu Ile Asn Ala Leu Ile Thr Pro Ala Glu Glu Leu Asp
305                 310                 315                 320
Phe Arg Val His Ile Arg Ser Glu Leu Met Arg Leu Gly Leu His Gln
                325                 330                 335
Val Leu Gln Glu Leu Arg Glu Ile Glu Asn Glu Asp Met Lys Val Gln
            340                 345                 350
Leu Cys Val Phe Asp Glu Gln Gly Asp Glu Asp Phe Phe Asp Leu Lys
        355                 360                 365
Gly Arg Leu Asp Asp Ile Arg Met Glu Met Asp Phe Gly Glu Val
    370                 375                 380
Phe Gln Ile Ile Leu Asn Thr Val Lys Asp Ser Lys Ala Glu Pro His
385                 390                 395                 400
Phe Leu Ser Ile Leu Gln His Leu Leu Leu Val Arg Asn Asp Tyr Glu
                405                 410                 415
Ala Arg Pro Gln Tyr Tyr Lys Leu Ile Glu Glu Cys Val Ser Gln Ile
            420                 425                 430
Val Leu His Lys Asn Gly Thr Asp Pro Asp Phe Lys Cys Arg His Leu
        435                 440                 445
Gln Ile Asp Ile Glu Arg Leu Val Asp Gln Met Ile Asp Lys Thr Lys
    450                 455                 460
Val Glu Lys Ser Glu Ala Lys Ala Thr Glu Leu Glu Lys Lys Leu Asp
465                 470                 475                 480
Ser Glu Leu Thr Ala Arg His Glu Leu Gln Val Glu Met Lys Lys Met
                485                 490                 495
Glu Asn Asp Phe Glu Gln Lys Leu Gln Asp Leu Gln Gly Glu Lys Asp
            500                 505                 510
Ala Leu Asp Ser Glu Lys Gln Gln Ile Thr Ala Gln Lys Gln Asp Leu
        515                 520                 525
Glu Ala Glu Val Ser Lys Leu Thr Gly Glu Val Ala Lys Leu Ser Lys
    530                 535                 540
Glu Leu Glu Asp Ala Lys Asn Glu Met Ala Ser Leu Ser Ala Val Val
545                 550                 555                 560
Val Ala Pro Ser Val Ser Ser Ala Ala Val Pro Ala Pro Pro
                565                 570                 575
Leu Pro Gly Asp Ser Gly Thr Val Ile Pro Pro Pro Pro Pro
            580                 585                 590
Pro Leu Pro Gly Gly Val Val Pro Ser Pro Pro Leu Pro Pro Gly
        595                 600                 605
Thr Cys Ile Pro Pro Pro Pro Leu Pro Gly Gly Ala Cys Ile Pro
    610                 615                 620
```

```
Pro Pro Pro Gln Leu Pro Gly Ser Ala Ala Ile Pro Pro Pro Pro
625                 630                 635                 640

Leu Pro Gly Val Ala Ser Ile Pro Pro Pro Pro Leu Pro Gly Ala
            645                 650                 655

Thr Ala Ile Pro Pro Pro Pro Leu Pro Gly Ala Thr Ala Ile Pro
            660                 665                 670

Pro Pro Pro Pro Leu Pro Gly Gly Thr Gly Ile Pro Pro Pro Pro
            675                 680                 685

Pro Leu Pro Gly Ser Val Gly Val Pro Pro Pro Pro Leu Pro Gly
690                 695                 700

Gly Pro Gly Leu Pro Pro Pro Pro Phe Pro Gly Ala Pro Gly
705                 710                 715                 720

Ile Pro Pro Pro Pro Gly Met Gly Val Pro Pro Pro Pro Phe
                725                 730                 735

Gly Phe Gly Val Pro Ala Ala Pro Val Leu Pro Phe Gly Leu Thr Pro
                740                 745                 750

Lys Lys Val Tyr Lys Pro Glu Val Gln Leu Arg Arg Pro Asn Trp Ser
            755                 760                 765

Lys Phe Val Ala Glu Asp Leu Ser Gln Asp Cys Phe Trp Thr Lys Val
770                 775                 780

Lys Glu Asp Arg Phe Glu Asn Asn Glu Leu Phe Ala Lys Leu Thr Leu
785                 790                 795                 800

Ala Phe Ser Ala Gln Thr Lys Thr Ser Lys Ala Lys Lys Asp Gln Glu
                805                 810                 815

Gly Gly Glu Glu Lys Lys Ser Val Gln Lys Lys Val Lys Glu Leu
                820                 825                 830

Lys Val Leu Asp Ser Lys Thr Ala Gln Asn Leu Ser Ile Phe Leu Gly
            835                 840                 845

Ser Phe Arg Met Pro Tyr Gln Glu Ile Lys Asn Val Ile Leu Glu Val
            850                 855                 860

Asn Glu Ala Val Leu Thr Glu Ser Met Ile Gln Asn Leu Ile Lys Gln
865                 870                 875                 880

Met Pro Glu Pro Glu Gln Leu Lys Met Leu Ser Glu Leu Lys Glu Glu
                885                 890                 895

Tyr Asp Asp Leu Ala Glu Ser Glu Gln Phe Gly Val Val Met Gly Thr
            900                 905                 910

Val Pro Arg Leu Arg Pro Arg Leu Asn Ala Ile Leu Phe Lys Leu Gln
            915                 920                 925

Phe Ser Glu Gln Val Glu Asn Ile Lys Pro Glu Ile Val Ser Val Thr
930                 935                 940

Ala Ala Cys Glu Glu Leu Arg Lys Ser Glu Asn Phe Ser Ser Leu Leu
945                 950                 955                 960

Glu Leu Thr Leu Leu Val Gly Asn Tyr Met Asn Ala Gly Ser Arg Asn
                965                 970                 975

Ala Gly Ala Phe Gly Phe Asn Ile Ser Phe Leu Cys Lys Leu Arg Asp
            980                 985                 990

Thr Lys Ser Ala Asp Gln Lys Met Thr Leu Leu His Phe Leu Ala Glu
            995                 1000                1005

Leu Cys Glu Asn Asp His Pro Glu Val Leu Lys Phe Pro Asp Glu Leu
            1010                1015                1020

Ala His Val Glu Lys Ala Ser Arg Val Ser Ala Glu Asn Leu Gln Lys
1025                1030                1035                1040

Ser Leu Asp Gln Met Lys Lys Gln Ile Ala Asp Val Glu Arg Asp Val
```

-continued

```
                1045                1050                1055
Gln Asn Phe Pro Ala Ala Thr Asp Glu Lys Asp Lys Phe Val Glu Lys
                1060                1065                1070

Met Thr Ser Phe Val Lys Asp Ala Gln Glu Gln Tyr Asn Lys Leu Arg
            1075                1080                1085

Met Met His Ser Asn Met Glu Thr Leu Tyr Lys Glu Leu Gly Asp Tyr
        1090                1095                1100

Phe Val Phe Asp Pro Lys Lys Leu Ser Val Glu Glu Phe Phe Met Asp
1105                1110                1115                1120

Leu His Asn Phe Arg Asn Met Phe Leu Gln Ala Val Lys Glu Asn Gln
            1125                1130                1135

Lys Arg Arg Glu Thr Glu Glu Lys Met Arg Arg Ala Lys Leu Ala Lys
        1140                1145                1150

Glu Lys Ala Glu Lys Glu Arg Leu Glu Lys Gln Gln Lys Arg Glu Gln
            1155                1160                1165

Leu Ile Asp Met Asn Ala Glu Gly Asp Glu Thr Gly Val Met Asp Ser
        1170                1175                1180

Leu Leu Glu Ala Leu Gln Ser Gly Ala Ala Phe Arg Arg Lys Arg Gly
1185                1190                1195                1200

Pro Arg Gln Val Asn Arg Lys Ala Gly Cys Ala Val Thr Ser Leu Leu
            1205                1210                1215

Ala Ser Glu Leu Thr Lys Asp Asp Ala Met Ala Pro Gly Pro Val Lys
            1220                1225                1230

Val Pro Lys Lys Ser Glu Gly Val Pro Thr Ile Leu Glu Glu Ala Lys
            1235                1240                1245

Glu Leu Val Gly Arg Ala Ser
        1250                1255

(2) INFORMATION FOR SEQ ID NO:2:

(i) SEQUENCE CHARACTERISTICS:
        (A) LENGTH: 4399 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Mouse (ix) FEATURE:
        (A) NAME/KEY: CDS
        (B) LOCATION: 94..3858

(xi) SEQUENCE DESCRIPTION: SEQ ID NO:2:

GAAGGCTGCT GGGCGGCGGC GGTGGTTGCT GGCTCGGGGC AGCCGGGCGC GAGCGGCGTA        60

GACAAGGGGT CACTTGCCGG CGCTAATCAG GAC ATG GAG CCG TCC GGC GGG GGC        114
                                    Met Glu Pro Ser Gly Gly Gly
                                     1               5

CTG GGG CCC GGC CGC GGT ACC CGG GAC AAG AAG AAG GGT CGG AGC CCG        162
Leu Gly Pro Gly Arg Gly Thr Arg Asp Lys Lys Lys Gly Arg Ser Pro
         10                  15                  20

GAT GAG CTG CCT GCG ACG GGC GGC GAC GGC GGC AAA CAT AAG AAA TTT        210
Asp Glu Leu Pro Ala Thr Gly Gly Asp Gly Gly Lys His Lys Lys Phe
    25                  30                  35

CTG GAG AGA TTT ACC AGC ATG AGG ATT AAG AAG GAG AAA GAA AAG CCC        258
Leu Glu Arg Phe Thr Ser Met Arg Ile Lys Lys Glu Lys Glu Lys Pro
 40                  45                  50                  55
```

```
AAT TCT GCT CAT AGA AAC TCC TCT GCA TCG TAC GGA GAT GAC CCC ACT      306
Asn Ser Ala His Arg Asn Ser Ser Ala Ser Tyr Gly Asp Asp Pro Thr
            60                  65                  70

GCT CAG TCA TTG CAG GAC ATC TCA GAC GAG CAA GTT CTT GTC CTC TTT      354
Ala Gln Ser Leu Gln Asp Ile Ser Asp Glu Gln Val Leu Val Leu Phe
                75                  80                  85

GAG CAG ATG CTG GTG GAT ATG AAC CTG AAT GAG GAG AAG CAG CAG CCT      402
Glu Gln Met Leu Val Asp Met Asn Leu Asn Glu Glu Lys Gln Gln Pro
                    90                  95                 100

TTG CGA GAG AAG GAC ATT GTC ATC AAG AGG GAG ATG GTG TCG CAA TAT      450
Leu Arg Glu Lys Asp Ile Val Ile Lys Arg Glu Met Val Ser Gln Tyr
           105                 110                 115

CTG CAC ACT TCC AAG GCT GGC ATG AAC CAG AAA GAG AGC TCT AGG TCT      498
Leu His Thr Ser Lys Ala Gly Met Asn Gln Lys Glu Ser Ser Arg Ser
120                 125                 130                 135

GCC ATG ATG TAC ATC CAG GAG CTG AGG TCG GGC TTG CGG GAT ATG CAC      546
Ala Met Met Tyr Ile Gln Glu Leu Arg Ser Gly Leu Arg Asp Met His
                140                 145                 150

CTG CTT AGC TGC CTT GAG TCC CTT CGA GTC TCT CTC AAC AAT AAC CCT      594
Leu Leu Ser Cys Leu Glu Ser Leu Arg Val Ser Leu Asn Asn Asn Pro
                155                 160                 165

GTC AGT TGG GTG CAG ACA TTT GGT GCT GAG GGC CTA GCC TCC TTA TTG      642
Val Ser Trp Val Gln Thr Phe Gly Ala Glu Gly Leu Ala Ser Leu Leu
            170                 175                 180

GAC ATC CTC AAA CGA CTC CAT GAT GAG AAA GAG GAG ACT TCT GGA AAC      690
Asp Ile Leu Lys Arg Leu His Asp Glu Lys Glu Glu Thr Ser Gly Asn
185                 190                 195

TAC GAC AGC CGA AAC CAG CAT GAG ATT ATC CGC TGT TTG AAG GCT TTC      738
Tyr Asp Ser Arg Asn Gln His Glu Ile Ile Arg Cys Leu Lys Ala Phe
200                 205                 210                 215

ATG AAC AAC AAG TTT GGA ATC AAA ACT ATG TTG GAG ACG GAA GAA GGA      786
Met Asn Asn Lys Phe Gly Ile Lys Thr Met Leu Glu Thr Glu Glu Gly
                220                 225                 230

ATC CTA CTG CTG GTC AGA GCC ATG GAT CCT GCT GTT CCC AAT ATG ATG      834
Ile Leu Leu Leu Val Arg Ala Met Asp Pro Ala Val Pro Asn Met Met
                235                 240                 245

ATT GAT GCA GCA AAG CTG CTG TCT GCC CTC TGT ATC CTG CCG CAG CCG      882
Ile Asp Ala Ala Lys Leu Leu Ser Ala Leu Cys Ile Leu Pro Gln Pro
            250                 255                 260

GAG GAC ATG AAT GAA CGA GTT CTA GAG GCA ATG ACA GAG AGA GCT GAA      930
Glu Asp Met Asn Glu Arg Val Leu Glu Ala Met Thr Glu Arg Ala Glu
265                 270                 275

ATG GAT GAG GTC GAA CGC TTC CAG CCA CTT CTG GAC GGA TTA AAA AGT      978
Met Asp Glu Val Glu Arg Phe Gln Pro Leu Leu Asp Gly Leu Lys Ser
280                 285                 290                 295

GGG ACC TCT ATT GCC CTC AAA GTG GGA TGC CTA CAG CTC ATC AAT GCT     1026
Gly Thr Ser Ile Ala Leu Lys Val Gly Cys Leu Gln Leu Ile Asn Ala
                300                 305                 310

CTC ATC ACT CCA GCT GAG GAA CTG GAC TTC CGA GTT CAC ATC CGA AGT     1074
Leu Ile Thr Pro Ala Glu Glu Leu Asp Phe Arg Val His Ile Arg Ser
            315                 320                 325

GAG CTG ATG CGC CTG GGG CTG CAT CAG GTG TTG CAG GAG CTT CGA GAG     1122
Glu Leu Met Arg Leu Gly Leu His Gln Val Leu Gln Glu Leu Arg Glu
                330                 335                 340

ATT GAA AAT GAA GAT ATG AAA GTA CAG CTG TGC GTG TTT GAT GAA CAA     1170
Ile Glu Asn Glu Asp Met Lys Val Gln Leu Cys Val Phe Asp Glu Gln
345                 350                 355

GGG GAT GAA GAT TTC TTT GAT CTG AAG GGA CGG CTG GAT GAT ATC CGC     1218
Gly Asp Glu Asp Phe Phe Asp Leu Lys Gly Arg Leu Asp Asp Ile Arg
360                 365                 370                 375
```

```
ATG GAG ATG GAT GAC TTT GGT GAA GTT TTT CAG ATT ATT TTA AAC ACA        1266
Met Glu Met Asp Asp Phe Gly Glu Val Phe Gln Ile Ile Leu Asn Thr
                    380                 385                 390

GTG AAA GAT TCA AAG GCA GAG CCA CAC TTC CTG TCT ATC TTG CAG CAT        1314
Val Lys Asp Ser Lys Ala Glu Pro His Phe Leu Ser Ile Leu Gln His
                395                 400                 405

CTC CTG TTG GTC CGA AAT GAT TAT GAA GCC AGG CCA CAG TAC TAT AAA        1362
Leu Leu Leu Val Arg Asn Asp Tyr Glu Ala Arg Pro Gln Tyr Tyr Lys
            410                 415                 420

CTG ATT GAA GAA TGT GTT TCT CAG ATA GTT CTA CAC AAA AAT GGA ACT        1410
Leu Ile Glu Glu Cys Val Ser Gln Ile Val Leu His Lys Asn Gly Thr
        425                 430                 435

GAT CCT GAC TTC AAG TGC CGA CAC CTG CAG ATT GAT ATT GAG AGA TTG        1458
Asp Pro Asp Phe Lys Cys Arg His Leu Gln Ile Asp Ile Glu Arg Leu
440                 445                 450                 455

GTT GAT CAA ATG ATT GAT AAA ACA AAG GTG GAA AAA TCT GAG GCC AAA        1506
Val Asp Gln Met Ile Asp Lys Thr Lys Val Glu Lys Ser Glu Ala Lys
                460                 465                 470

GCT ACA GAG CTG GAA AAA AAG TTG GAT TCA GAA TTA ACA GCG CGG CAC        1554
Ala Thr Glu Leu Glu Lys Lys Leu Asp Ser Glu Leu Thr Ala Arg His
                475                 480                 485

GAG TTA CAA GTA GAA ATG AAA AAG ATG GAA AAT GAC TTT GAG CAG AAA        1602
Glu Leu Gln Val Glu Met Lys Lys Met Glu Asn Asp Phe Glu Gln Lys
            490                 495                 500

CTT CAG GAT CTT CAA GGA GAA AAG GAT GCC TTG GAT TCT GAA AAG CAG        1650
Leu Gln Asp Leu Gln Gly Glu Lys Asp Ala Leu Asp Ser Glu Lys Gln
        505                 510                 515

CAG ATC ACT GCA CAG AAA CAA GAC CTG GAG GCA GAG GTG TCC AAG CTG        1698
Gln Ile Thr Ala Gln Lys Gln Asp Leu Glu Ala Glu Val Ser Lys Leu
520                 525                 530                 535

ACA GGA GAG GTT GCC AAG CTG TCA AAA GAA CTA GAA GAT GCC AAG AAT        1746
Thr Gly Glu Val Ala Lys Leu Ser Lys Glu Leu Glu Asp Ala Lys Asn
                540                 545                 550

GAA ATG GCT TCT CTC TCT GCT GTG GTT GTT GCA CCT TCT GTT TCT AGC        1794
Glu Met Ala Ser Leu Ser Ala Val Val Val Ala Pro Ser Val Ser Ser
                555                 560                 565

AGT GCT GCT GTT CCC CCT GCC CCT CCT CTG CCT GGT GAC TCT GGC ACT        1842
Ser Ala Ala Val Pro Pro Ala Pro Pro Leu Pro Gly Asp Ser Gly Thr
            570                 575                 580

GTT ATT CCA CCT CCC CCA CCC CCA CCT CCT CTT CCT GGA GGT GTG GTC        1890
Val Ile Pro Pro Pro Pro Pro Pro Pro Leu Pro Gly Gly Val Val
        585                 590                 595

CCA CCA TCC CCT CCT CTG CCT CCA GGT ACT TGT ATC CCT CCA CCT CCT        1938
Pro Pro Ser Pro Pro Leu Pro Pro Gly Thr Cys Ile Pro Pro Pro Pro
600                 605                 610                 615

CCT TTA CCT GGA GGT GCT TGT ATA CCC CCT CCC CCC CAG TTG CCT GGC        1986
Pro Leu Pro Gly Gly Ala Cys Ile Pro Pro Pro Pro Gln Leu Pro Gly
                620                 625                 630

AGT GCT GCC ATC CCT CCA CCT CCT CCT CTA CCT GGA GTT GCT TCC ATC        2034
Ser Ala Ala Ile Pro Pro Pro Pro Pro Leu Pro Gly Val Ala Ser Ile
                635                 640                 645

CCC CCA CCT CCC CCT TTG CCT GGG GCT ACT GCC ATC CCC CCA CCT CCC        2082
Pro Pro Pro Pro Pro Leu Pro Gly Ala Thr Ala Ile Pro Pro Pro Pro
            650                 655                 660

CCT TTG CCT GGG GCT ACT GCC ATC CCC CCA CCT CCC CCT TTG CCT GGA        2130
Pro Leu Pro Gly Ala Thr Ala Ile Pro Pro Pro Pro Pro Leu Pro Gly
        665                 670                 675

GGT ACA GGT ATA CCA CCA CCA CCT CCT CCT TTG CCT GGA AGT GTT GGC        2178
Gly Thr Gly Ile Pro Pro Pro Pro Pro Pro Leu Pro Gly Ser Val Gly
```

```
                680                 685                 690                 695
GTT CCC CCA CCC CCT CCC TTG CCT GGA GGA CCA GGA CTG CCT CCT CCC         2226
Val Pro Pro Pro Pro Pro Leu Pro Gly Gly Pro Gly Leu Pro Pro Pro
                    700                 705                 710

CCC CCC CCT TTT CCT GGA GCA CCT GGC ATT CCT CCA CCT CCA CCT GGT         2274
Pro Pro Pro Phe Pro Gly Ala Pro Gly Ile Pro Pro Pro Pro Pro Gly
            715                 720                 725

ATG GGC GTG CCT CCA CCT CCC CCC TTT GGA TTT GGG GTT CCT GCG GCC         2322
Met Gly Val Pro Pro Pro Pro Pro Phe Gly Phe Gly Val Pro Ala Ala
        730                 735                 740

CCA GTT CTG CCA TTT GGA TTA ACC CCC AAA AAA GTT TAT AAG CCA GAG         2370
Pro Val Leu Pro Phe Gly Leu Thr Pro Lys Lys Val Tyr Lys Pro Glu
    745                 750                 755

GTG CAG CTC CGG AGG CCA AAC TGG TCC AAG TTT GTG GCT GAG GAC CTT         2418
Val Gln Leu Arg Arg Pro Asn Trp Ser Lys Phe Val Ala Glu Asp Leu
760                 765                 770                 775

TCC CAG GAC TGC TTC TGG ACA AAG GTG AAG GAG GAC CGC TTT GAG AAC         2466
Ser Gln Asp Cys Phe Trp Thr Lys Val Lys Glu Asp Arg Phe Glu Asn
                780                 785                 790

AAT GAA CTT TTT GCC AAA CTT ACC CTT GCC TTC TCC GCC CAG ACC AAG         2514
Asn Glu Leu Phe Ala Lys Leu Thr Leu Ala Phe Ser Ala Gln Thr Lys
            795                 800                 805

ACT TCT AAA GCC AAG AAG GAT CAA GAA GGT GGA GAA GAA AAG AAA TCT         2562
Thr Ser Lys Ala Lys Lys Asp Gln Glu Gly Gly Glu Glu Lys Lys Ser
        810                 815                 820

GTT CAA AAG AAG AAA GTA AAA GAG CTG AAA GTG CTG GAT TCA AAG ACA         2610
Val Gln Lys Lys Lys Val Lys Glu Leu Lys Val Leu Asp Ser Lys Thr
    825                 830                 835

GCG CAG AAT CTC TCA ATC TTT TTG GGT TCA TTC CGC ATG CCC TAT CAA         2658
Ala Gln Asn Leu Ser Ile Phe Leu Gly Ser Phe Arg Met Pro Tyr Gln
840                 845                 850                 855

GAG ATA AAG AAC GTT ATC CTG GAG GTG AAT GAG GCT GTT CTC ACA GAG         2706
Glu Ile Lys Asn Val Ile Leu Glu Val Asn Glu Ala Val Leu Thr Glu
                860                 865                 870

TCT ATG ATC CAG AAC CTC ATT AAA CAG ATG CCA GAG CCA GAG CAG CTA         2754
Ser Met Ile Gln Asn Leu Ile Lys Gln Met Pro Glu Pro Glu Gln Leu
            875                 880                 885

AAG ATG CTC TCT GAA CTG AAG GAG GAG TAC GAT GAT CTG GCT GAG TCA         2802
Lys Met Leu Ser Glu Leu Lys Glu Glu Tyr Asp Asp Leu Ala Glu Ser
        890                 895                 900

GAG CAG TTT GGT GTG GTG ATG GGC ACA GTG CCC CGC CTT CGG CCT CGC         2850
Glu Gln Phe Gly Val Val Met Gly Thr Val Pro Arg Leu Arg Pro Arg
    905                 910                 915

CTC AAC GCC ATC CTC TTC AAG CTA CAG TTC AGT GAG CAA GTT GAG AAC         2898
Leu Asn Ala Ile Leu Phe Lys Leu Gln Phe Ser Glu Gln Val Glu Asn
920                 925                 930                 935

ATC AAG CCA GAG ATC GTG TCT GTC ACC GCC GCA TGC GAA GAG CTG CGT         2946
Ile Lys Pro Glu Ile Val Ser Val Thr Ala Ala Cys Glu Glu Leu Arg
                940                 945                 950

AAG AGT GAG AAC TTC TCC AGC CTC CTG GAG CTC ACA CTG CTG GTC GGA         2994
Lys Ser Glu Asn Phe Ser Ser Leu Leu Glu Leu Thr Leu Leu Val Gly
            955                 960                 965

AAC TAT ATG AAT GCG GGC TCC AGG AAT GCT GGT GCT TTC GGC TTC AAT         3042
Asn Tyr Met Asn Ala Gly Ser Arg Asn Ala Gly Ala Phe Gly Phe Asn
        970                 975                 980

ATC AGC TTC CTT TGT AAG CTT CGA GAC ACC AAG TCT GCA GAT CAG AAG         3090
Ile Ser Phe Leu Cys Lys Leu Arg Asp Thr Lys Ser Ala Asp Gln Lys
    985                 990                 995

ATG ACT CTG TTG CAT TTC TTG GCT GAG TTA TGT GAG AAT GAC CAC CCC         3138
```

```
Met Thr Leu Leu His Phe Leu Ala Glu Leu Cys Glu Asn Asp His Pro
1000             1005                 1010                 1015

GAA GTC CTC AAG TTT CCT GAT GAG CTT GCC CAT GTA GAG AAA GCC AGC      3186
Glu Val Leu Lys Phe Pro Asp Glu Leu Ala His Val Glu Lys Ala Ser
        1020                 1025                 1030

AGA GTC TCT GCT GAG AAC CTG CAG AAG AGC TTA GAT CAG ATG AAG AAG      3234
Arg Val Ser Ala Glu Asn Leu Gln Lys Ser Leu Asp Gln Met Lys Lys
            1035                 1040                 1045

CAG ATT GCG GAC GTG GAG CGC GAT GTT CAG AAT TTC CCA GCT GCC ACT      3282
Gln Ile Ala Asp Val Glu Arg Asp Val Gln Asn Phe Pro Ala Ala Thr
                1050                 1055                 1060

GAC GAG AAG GAC AAG TTT GTT GAG AAG ATG ACC AGC TTT GTG AAG GAT      3330
Asp Glu Lys Asp Lys Phe Val Glu Lys Met Thr Ser Phe Val Lys Asp
    1065                 1070                 1075

GCA CAG GAA CAG TAT AAC AAA CTA CGG ATG ATG CAC TCC AAC ATG GAG      3378
Ala Gln Glu Gln Tyr Asn Lys Leu Arg Met Met His Ser Asn Met Glu
1080                 1085                 1090                 1095

ACC CTC TAT AAG GAG CTA GGT GAC TAC TTC GTC TTT GAC CCT AAG AAG      3426
Thr Leu Tyr Lys Glu Leu Gly Asp Tyr Phe Val Phe Asp Pro Lys Lys
        1100                 1105                 1110

TTG TCT GTA GAG GAA TTC TTT ATG GAT CTG CAC AAC TTT AGG AAT ATG      3474
Leu Ser Val Glu Glu Phe Phe Met Asp Leu His Asn Phe Arg Asn Met
            1115                 1120                 1125

TTT TTG CAA GCA GTC AAG GAA AAC CAG AAG CGC CGG GAA ACA GAA GAA      3522
Phe Leu Gln Ala Val Lys Glu Asn Gln Lys Arg Arg Glu Thr Glu Glu
                1130                 1135                 1140

AAG ATG CGG AGA GCA AAA TTA GCC AAG GAG AAG GCA GAA AAA GAG CGA      3570
Lys Met Arg Arg Ala Lys Leu Ala Lys Glu Lys Ala Glu Lys Glu Arg
    1145                 1150                 1155

CTG GAG AAG CAG CAG AAG CGC GAG CAG CTC ATC GAC ATG AAC GCA GAG      3618
Leu Glu Lys Gln Gln Lys Arg Glu Gln Leu Ile Asp Met Asn Ala Glu
1160                 1165                 1170                 1175

GGG GAT GAG ACA GGT GTG ATG GAC AGT CTT CTA GAA GCT CTG CAG TCA      3666
Gly Asp Glu Thr Gly Val Met Asp Ser Leu Leu Glu Ala Leu Gln Ser
        1180                 1185                 1190

GGG GCA GCA TTC CGA CGG AAG AGA GGG CCC CGG CAG GTC AAC AGG AAG      3714
Gly Ala Ala Phe Arg Arg Lys Arg Gly Pro Arg Gln Val Asn Arg Lys
            1195                 1200                 1205

GCT GGG TGT GCA GTC ACA TCT CTG CTA GCC TCG GAG CTG ACC AAG GAT      3762
Ala Gly Cys Ala Val Thr Ser Leu Leu Ala Ser Glu Leu Thr Lys Asp
                1210                 1215                 1220

GAT GCC ATG GCT CCT GGT CCT GTT AAG GTA CCC AAG AAA AGT GAA GGA      3810
Asp Ala Met Ala Pro Gly Pro Val Lys Val Pro Lys Lys Ser Glu Gly
    1225                 1230                 1235

GTC CCC ACA ATC CTG GAA GAA GCC AAG GAG CTG GTT GGC CGT GCA AGC      3858
Val Pro Thr Ile Leu Glu Glu Ala Lys Glu Leu Val Gly Arg Ala Ser
1240                 1245                 1250                 1255

TAAGCTGGGC TTTATGGCCA TTGCTGCTCC TAGGCGAAGC CCAGACTGTC GACCTGCAGC    3918

ATGGGCCTAA ATGGTCAAGG AGATAGTGGC CACTCCACCA CCTGACCCTG TCTTTCTGTC    3978

TGGCCTGCTG CTCTCTGAAC ACCACATACA GCTTCAGCTG CCTGGAGGCC AAAAGGAAGG    4038

GGCAGTGTAG GAGTGGCCTG AGCCCAGCCC AGCCAGCCCT GGCTGTTGTA TTACCAAAGC    4098

AGGGTCCGTG TTTGCTGCCT TAACCCTGTC TCCTCTATGT TACCCAGAGG TCCTGGTCTC    4158

AGACAGAACC CAGCCTGCTT TCTCAGCCCC ACTCTCTAGT GGGCCTTCCC TAGGTCAATC    4218

TTGCTGCATT TGTGCTTTTC TTTTGTGGTT TCTCTGGCCC TGAGAATAGC ATGGGACTTG    4278

TGAACCTTTG GGCTAGGTCT TTTCACTGCT GTCACCTCTG CTTTTCCTCC TGGCAATTAT    4338
```

```
TTATTACTAG TGCTGTGGCA TTGGGAGCTG CTTCTGCAAA GCAGGAAGCA AATCCCACCC      4398
T                                                                     4399
```

(2) INFORMATION FOR SEQ ID NO:3:

(i) SEQUENCE CHARACTERISTICS:
        (A) LENGTH: 1315 amino acids
        (B) TYPE: amino acid
        (D) TOPOLOGY: linear (ii) MOLECULE TYPE: protein (xi) SEQUENCE DESCRIPTION: SEQ ID NO:3:

```
Met Arg Ala Lys Pro Leu Gly Phe Gln Gly Arg Gly Ala Trp Ala Gly
  1               5                  10                  15

Gly Ala Gly Gly Arg Glu Gly Val Leu Ala Glu Ala Gly Lys Gly Arg
                 20                  25                  30

Arg Gly Pro Gly Ile Pro Gly Gly Val Gly Ala Gly Ser Pro Ala Ser
             35                  40                  45

Val Asn Arg Asp Met Glu Pro Pro Gly Gly Ser Leu Gly Pro Gly Arg
 50                  55                  60

Gly Thr Arg Asp Lys Lys Gly Arg Ser Pro Asp Glu Leu Pro Ser
 65                  70                  75                  80

Ala Gly Gly Asp Gly Gly Lys Ser Lys Lys Phe Leu Glu Arg Phe Thr
                 85                  90                  95

Ser Met Arg Ile Lys Lys Glu Lys Glu Lys Pro Asn Ser Ala His Arg
                100                 105                 110

Asn Ser Ser Ala Ser Tyr Gly Asp Asp Pro Thr Ala Gln Ser Leu Gln
                115                 120                 125

Asp Val Ser Asp Glu Gln Val Leu Val Leu Phe Glu Gln Met Leu Leu
                130                 135                 140

Asp Met Asn Leu Asn Glu Lys Gln Gln Pro Leu Arg Glu Lys Asp
145                 150                 155                 160

Ile Ile Ile Lys Arg Glu Met Val Ser Gln Tyr Leu Tyr Thr Ser Lys
                165                 170                 175

Ala Gly Met Ser Gln Lys Glu Ser Ser Lys Ser Ala Met Met Tyr Ile
                180                 185                 190

Gln Glu Leu Arg Ser Gly Leu Arg Asp Met Pro Leu Leu Ser Cys Leu
                195                 200                 205

Glu Ser Leu Arg Val Ser Leu Asn Asn Asn Pro Val Ser Trp Val Gln
                210                 215                 220

Thr Phe Gly Ala Glu Gly Leu Ala Ser Leu Leu Asp Ile Leu Lys Arg
225                 230                 235                 240

Leu His Asp Glu Lys Glu Glu Thr Ala Gly Ser Tyr Asp Ser Arg Asn
                245                 250                 255

Lys His Glu Ile Ile Arg Cys Leu Lys Ala Phe Met Asn Asn Lys Phe
                260                 265                 270

Gly Ile Lys Thr Met Leu Glu Thr Glu Glu Gly Ile Leu Leu Leu Val
                275                 280                 285

Arg Ala Met Asp Pro Ala Val Pro Asn Met Met Ile Asp Ala Ala Lys
                290                 295                 300

Leu Leu Ser Ala Leu Cys Ile Leu Pro Gln Pro Glu Asp Met Asn Glu
305                 310                 315                 320

Arg Val Leu Glu Ala Met Thr Glu Arg Ala Glu Met Asp Glu Val Glu
                325                 330                 335
```

-continued

```
Arg Phe Gln Pro Leu Leu Asp Gly Leu Lys Ser Gly Thr Thr Ile Ala
                340                 345                 350

Leu Lys Val Gly Cys Leu Gln Leu Ile Asn Ala Leu Ile Thr Pro Ala
            355                 360                 365

Glu Glu Leu Asp Phe Arg Val His Ile Arg Ser Glu Leu Met Arg Leu
        370                 375                 380

Gly Leu His Gln Val Leu Gln Asp Leu Arg Glu Ile Glu Asn Glu Asp
385                 390                 395                 400

Met Arg Val Gln Leu Asn Val Phe Asp Glu Gln Gly Glu Glu Asp Ser
                405                 410                 415

Tyr Asp Leu Lys Gly Arg Leu Asp Asp Ile Arg Met Glu Met Asp Asp
            420                 425                 430

Phe Asn Glu Val Phe Gln Ile Leu Leu Asn Thr Val Lys Asp Ser Lys
        435                 440                 445

Ala Glu Pro His Phe Leu Ser Ile Leu Gln His Leu Leu Leu Val Arg
    450                 455                 460

Asn Asp Tyr Glu Ala Arg Pro Gln Tyr Tyr Lys Leu Ile Glu Glu Cys
465                 470                 475                 480

Ile Ser Gln Ile Val Leu His Lys Asn Gly Ala Asp Pro Asp Phe Lys
                485                 490                 495

Cys Arg His Leu Gln Ile Glu Ile Glu Gly Leu Ile Asp Gln Met Ile
            500                 505                 510

Asp Lys Thr Lys Val Glu Lys Ser Glu Ala Lys Ala Glu Leu Glu
        515                 520                 525

Lys Lys Leu Asp Ser Glu Leu Thr Ala Arg His Glu Leu Gln Val Glu
    530                 535                 540

Met Lys Lys Met Glu Ser Asp Phe Glu Gln Lys Leu Gln Asp Leu Gln
545                 550                 555                 560

Gly Glu Lys Asp Ala Leu His Ser Glu Lys Gln Gln Ile Ala Thr Glu
                565                 570                 575

Lys Gln Asp Leu Glu Ala Glu Val Ser Gln Leu Thr Gly Glu Val Ala
            580                 585                 590

Lys Leu Thr Lys Glu Leu Glu Asp Ala Lys Lys Glu Met Ala Ser Leu
        595                 600                 605

Ser Ala Ala Ile Thr Val Pro Pro Ser Val Pro Ser Arg Ala Pro
    610                 615                 620

Val Pro Pro Ala Pro Pro Leu Pro Gly Asp Ser Gly Thr Ile Ile Pro
625                 630                 635                 640

Pro Pro Pro Ala Pro Gly Asp Ser Thr Thr Pro Pro Pro Pro Pro Pro
                645                 650                 655

Pro Pro Pro Pro Pro Pro Leu Pro Gly Gly Val Cys Ile Ser Ser
            660                 665                 670

Pro Pro Ser Leu Pro Gly Gly Thr Ala Ile Ser Pro Pro Pro Leu
        675                 680                 685

Ser Gly Asp Ala Thr Ile Pro Pro Pro Pro Leu Pro Glu Gly Val
    690                 695                 700

Gly Ile Pro Ser Pro Ser Ser Leu Pro Gly Gly Thr Ala Ile Pro Pro
705                 710                 715                 720

Pro Pro Pro Leu Pro Gly Ser Ala Arg Ile Pro Pro Pro Pro Pro
                725                 730                 735

Leu Pro Gly Ser Ala Gly Ile Pro Pro Pro Pro Pro Leu Pro Gly
            740                 745                 750

Glu Ala Gly Met Pro Pro Pro Pro Pro Leu Pro Gly Gly Pro Gly
```

-continued

```
                755                 760                 765
Ile Pro Pro Pro Pro Phe Pro Gly Gly Pro Gly Ile Pro Pro Pro
    770                 775                 780

Pro Pro Gly Met Gly Met Pro Pro Pro Phe Gly Phe Gly Val
785                 790                 795                 800

Pro Ala Ala Pro Val Leu Pro Phe Gly Leu Thr Pro Lys Lys Leu Tyr
                805                 810                 815

Lys Pro Glu Val Gln Leu Arg Arg Pro Asn Trp Ser Lys Leu Val Ala
                820                 825                 830

Glu Asp Leu Ser Gln Asp Cys Phe Trp Thr Lys Val Lys Glu Asp Arg
                835                 840                 845

Phe Glu Asn Asn Glu Leu Phe Ala Lys Leu Thr Leu Thr Phe Ser Ala
    850                 855                 860

Gln Thr Lys Thr Ser Lys Ala Lys Lys Asp Gln Glu Gly Gly Glu Glu
865                 870                 875                 880

Lys Lys Ser Val Gln Lys Lys Val Lys Glu Leu Lys Val Leu Asp
                885                 890                 895

Ser Lys Thr Ala Gln Asn Leu Ser Ile Phe Leu Gly Ser Phe Arg Met
                900                 905                 910

Pro Tyr Gln Glu Ile Lys Asn Val Ile Leu Glu Val Asn Glu Ala Val
                915                 920                 925

Leu Thr Glu Ser Met Ile Gln Asn Leu Ile Lys Gln Met Pro Glu Pro
    930                 935                 940

Glu Gln Leu Lys Met Leu Ser Glu Leu Lys Asp Glu Tyr Asp Asp Leu
945                 950                 955                 960

Ala Glu Ser Glu Gln Phe Gly Val Val Met Gly Thr Val Pro Arg Leu
                965                 970                 975

Arg Pro Arg Leu Asn Ala Ile Leu Phe Lys Leu Gln Phe Ser Glu Gln
                980                 985                 990

Val Glu Asn Ile Lys Pro Glu Ile Val Ser Val Thr Ala Ala Cys Glu
                995                 1000                1005

Glu Leu Arg Lys Ser Glu Ser Phe Ser Asn Leu Leu Glu Ile Thr Leu
    1010                1015                1020

Leu Val Gly Asn Tyr Met Asn Ala Gly Ser Arg Asn Ala Gly Ala Phe
1025                1030                1035                1040

Gly Phe Asn Ile Ser Phe Leu Cys Lys Leu Arg Asp Thr Lys Ser Thr
                1045                1050                1055

Asp Gln Lys Met Thr Leu Leu His Phe Leu Ala Glu Leu Cys Glu Asn
                1060                1065                1070

Asp Tyr Pro Asp Val Leu Lys Phe Pro Asp Glu Leu Ala His Val Glu
                1075                1080                1085

Lys Ala Ser Arg Val Ser Ala Glu Asn Leu Gln Lys Asn Leu Asp Gln
    1090                1095                1100

Met Lys Lys Gln Ile Ser Asp Val Glu Arg Asp Val Gln Asn Phe Pro
1105                1110                1115                1120

Ala Ala Thr Asp Glu Lys Asp Lys Phe Val Glu Lys Met Thr Ser Phe
                1125                1130                1135

Val Lys Asp Ala Gln Glu Gln Tyr Asn Lys Leu Arg Met Met His Ser
                1140                1145                1150

Asn Met Glu Thr Leu Tyr Lys Glu Leu Gly Glu Tyr Phe Leu Phe Asp
                1155                1160                1165

Pro Lys Lys Leu Ser Val Glu Glu Phe Phe Met Asp Leu His Asn Phe
                1170                1175                1180
```

```
Arg Asn Met Phe Leu Gln Ala Val Lys Glu Asn Gln Lys Arg Arg Glu
1185                1190                1195                1200

Thr Glu Glu Lys Met Arg Arg Ala Lys Leu Ala Lys Glu Lys Ala Glu
            1205                1210                1215

Lys Glu Arg Leu Glu Lys Gln Gln Lys Arg Glu Gln Leu Ile Asp Met
        1220                1225                1230

Asn Ala Glu Gly Asp Glu Thr Gly Val Met Asp Ser Leu Leu Glu Ala
    1235                1240                1245

Leu Gln Ser Gly Ala Ala Phe Arg Arg Lys Arg Gly Pro Arg Gln Ala
        1250                1255                1260

Asn Arg Lys Ala Gly Cys Ala Val Thr Ser Leu Leu Ala Ser Glu Leu
1265                1270                1275                1280

Thr Lys Asp Asp Ala Met Ala Ala Val Pro Ala Lys Val Ser Lys Asn
            1285                1290                1295

Ser Glu Thr Phe Pro Thr Ile Leu Glu Glu Ala Lys Glu Leu Val Gly
        1300                1305                1310

Arg Ala Ser
        1315

(2) INFORMATION FOR SEQ ID NO:4:

(i) SEQUENCE CHARACTERISTICS:
        (A) LENGTH: 5822 base pairs
        (B) TYPE: nucleic acid
        (C) STRANDEDNESS: single
        (D) TOPOLOGY: linear (ii) MOLECULE TYPE: cDNA to mRNA (vi) ORIGINAL SOURCE:
        (A) ORGANISM: Human (ix) FEATURE:
        (A) NAME/KEY: CDS
        (B) LOCATION: 28..3972

(xi) SEQUENCE DESCRIPTION: SEQ ID NO:4:

AATATTGCGA GAGGCGGCGG CGGTGAA ATG CGA GCG AAG CCG CTC GGC TTC            51
                             Met Arg Ala Lys Pro Leu Gly Phe
                               1               5

CAG GGA AGG GGC GCC TGG GCT GGC GGA GCT GGA GGG AGG GAG GGA GTT          99
Gln Gly Arg Gly Ala Trp Ala Gly Gly Ala Gly Gly Arg Glu Gly Val
        10                  15                  20

CTC GCA GAA GCA GGA AAG GGG AGG AGG GGG CCC GGA ATT CCG GGC GGC         147
Leu Ala Glu Ala Gly Lys Gly Arg Arg Gly Pro Gly Ile Pro Gly Gly
 25                  30                  35                  40

GTA GGC GCG GGG TCG CCG GCC AGC GTG AAC CGG GAC ATG GAG CCG CCC         195
Val Gly Ala Gly Ser Pro Ala Ser Val Asn Arg Asp Met Glu Pro Pro
                45                  50                  55

GGC GGG AGC CTG GGG CCC GGC CGC GGG ACC CGG GAC AAG AAG AAG GGC         243
Gly Gly Ser Leu Gly Pro Gly Arg Gly Thr Arg Asp Lys Lys Lys Gly
            60                  65                  70

CGG AGC CCA GAT GAG CTG CCC TCG GCG GGC GGC GAC GGC GGC AAA TCT         291
Arg Ser Pro Asp Glu Leu Pro Ser Ala Gly Gly Asp Gly Gly Lys Ser
        75                  80                  85

AAG AAA TTT CTG GAG AGA TTT ACC AGC ATG AGA ATT AAG AAG GAG AAG         339
Lys Lys Phe Leu Glu Arg Phe Thr Ser Met Arg Ile Lys Lys Glu Lys
    90                  95                 100

GAA AAG CCC AAT TCT GCT CAT AGA AAT TCT TCT GCA TCA TAT GGG GAT         387
Glu Lys Pro Asn Ser Ala His Arg Asn Ser Ser Ala Ser Tyr Gly Asp
105                 110                 115                 120
```

```
GAT CCC ACA GCA CAG TCA TTG CAA GAT GTT TCA GAT GAA CAA GTG CTG            435
Asp Pro Thr Ala Gln Ser Leu Gln Asp Val Ser Asp Glu Gln Val Leu
            125                 130                 135

GTT CTC TTT GAA CAG ATG CTG CTG GAT ATG AAC CTG AAT GAG GAG AAA            483
Val Leu Phe Glu Gln Met Leu Leu Asp Met Asn Leu Asn Glu Glu Lys
            140                 145                 150

CAG CAA CCT TTG AGG GAG AAG GAC ATC ATC ATC AAG AGG GAG ATG GTG            531
Gln Gln Pro Leu Arg Glu Lys Asp Ile Ile Ile Lys Arg Glu Met Val
            155                 160                 165

TCC CAA TAC TTG TAC ACC TCC AAG GCT GGC ATG AGC CAG AAG GAG AGC            579
Ser Gln Tyr Leu Tyr Thr Ser Lys Ala Gly Met Ser Gln Lys Glu Ser
170                 175                 180

TCT AAG TCT GCC ATG ATG TAT ATT CAG GAG TTG AGG TCA GGC TTG CGG            627
Ser Lys Ser Ala Met Met Tyr Ile Gln Glu Leu Arg Ser Gly Leu Arg
185                 190                 195                 200

GAT ATG CCT CTG CTC AGC TGC CTG GAG TCC CTT CGT GTG TCT CTC AAC            675
Asp Met Pro Leu Leu Ser Cys Leu Glu Ser Leu Arg Val Ser Leu Asn
            205                 210                 215

AAC AAC CCT GTC AGT TGG GTG CAA ACA TTT GGT GCT GAA GGC TTG GCC            723
Asn Asn Pro Val Ser Trp Val Gln Thr Phe Gly Ala Glu Gly Leu Ala
            220                 225                 230

TCC TTA TTG GAC ATT CTT AAA CGA CTT CAT GAT GAG AAA GAA GAG ACT            771
Ser Leu Leu Asp Ile Leu Lys Arg Leu His Asp Glu Lys Glu Glu Thr
            235                 240                 245

GCT GGG AGT TAC GAT AGC CGG AAC AAG CAT GAG ATC ATT CGC TGC TTG            819
Ala Gly Ser Tyr Asp Ser Arg Asn Lys His Glu Ile Ile Arg Cys Leu
250                 255                 260

AAA GCT TTT ATG AAC AAC AAG TTT GGA ATC AAG ACC ATG TTG GAG ACA            867
Lys Ala Phe Met Asn Asn Lys Phe Gly Ile Lys Thr Met Leu Glu Thr
265                 270                 275                 280

GAA GAA GGA ATC CTA CTG CTG GTC AGA GCC ATG GAT CCT GCT GTT CCC            915
Glu Glu Gly Ile Leu Leu Leu Val Arg Ala Met Asp Pro Ala Val Pro
            285                 290                 295

AAC ATG ATG ATT GAT GCA GCT AAG CTG CTT TCT GCT CTT TGT ATT CTA            963
Asn Met Met Ile Asp Ala Ala Lys Leu Leu Ser Ala Leu Cys Ile Leu
            300                 305                 310

CCG CAG CCA GAG GAC ATG AAT GAA AGG GTT TTG GAG GCA ATG ACA GAA           1011
Pro Gln Pro Glu Asp Met Asn Glu Arg Val Leu Glu Ala Met Thr Glu
            315                 320                 325

AGA GCT GAG ATG GAT GAA GTG GAA CGT TTC CAG CCG CTG CTG GAT GGA           1059
Arg Ala Glu Met Asp Glu Val Glu Arg Phe Gln Pro Leu Leu Asp Gly
330                 335                 340

TTA AAA AGT GGA ACC ACT ATT GCA CTG AAG GTT GGA TGC CTA CAG CTG           1107
Leu Lys Ser Gly Thr Thr Ile Ala Leu Lys Val Gly Cys Leu Gln Leu
345                 350                 355                 360

ATC AAT GCT CTC ATC ACA CCA GCG GAG GAA CTT GAC TTC CGA GTT CAC           1155
Ile Asn Ala Leu Ile Thr Pro Ala Glu Glu Leu Asp Phe Arg Val His
            365                 370                 375

ATC AGA AGT GAA CTG ATG CGT TTG GGG CTA CAT CAG GTG TTG CAG GAC           1203
Ile Arg Ser Glu Leu Met Arg Leu Gly Leu His Gln Val Leu Gln Asp
            380                 385                 390

CTT CGA GAG ATT GAA AAT GAA GAT ATG AGA GTG CAA CTA AAT GTG TTT           1251
Leu Arg Glu Ile Glu Asn Glu Asp Met Arg Val Gln Leu Asn Val Phe
            395                 400                 405

GAT GAA CAA GGG GAA GAG GAT TCC TAT GAC CTG AAG GGA CGG CTG GAT           1299
Asp Glu Gln Gly Glu Glu Asp Ser Tyr Asp Leu Lys Gly Arg Leu Asp
410                 415                 420

GAC ATT CGC ATG GAG ATG GAT GAC TTT AAT GAA GTC TTT CAG ATT CTC           1347
Asp Ile Arg Met Glu Met Asp Asp Phe Asn Glu Val Phe Gln Ile Leu
```

-continued

| | | | | |
|---|---|---|---|---|
| 425 | 430 | 435 | 440 | |
| TTA AAC ACA GTG AAG GAT TCA AAG GCA GAG CCA CAC TTC CTT TCC ATC<br>Leu Asn Thr Val Lys Asp Ser Lys Ala Glu Pro His Phe Leu Ser Ile<br>445 450 455 | | | | 1395 |
| CTG CAG CAC TTA CTC TTG GTC CGA AAT GAC TAT GAG GCC AGA CCT CAG<br>Leu Gln His Leu Leu Leu Val Arg Asn Asp Tyr Glu Ala Arg Pro Gln<br>460 465 470 | | | | 1443 |
| TAC TAT AAG TTG ATT GAA GAA TGT ATT TCC CAG ATA GTT CTG CAC AAG<br>Tyr Tyr Lys Leu Ile Glu Glu Cys Ile Ser Gln Ile Val Leu His Lys<br>475 480 485 | | | | 1491 |
| AAC GGG GCT GAT CCT GAC TTC AAG TGC CGG CAC CTC CAG ATT GAG ATT<br>Asn Gly Ala Asp Pro Asp Phe Lys Cys Arg His Leu Gln Ile Glu Ile<br>490 495 500 | | | | 1539 |
| GAG GGA TTA ATT GAT CAA ATG ATT GAT AAG ACA AAG GTG GAG AAA TCT<br>Glu Gly Leu Ile Asp Gln Met Ile Asp Lys Thr Lys Val Glu Lys Ser<br>505 510 515 520 | | | | 1587 |
| GAA GCC AAA GCT GCA GAG CTG GAA AAG AAG TTG GAC TCA GAG TTA ACA<br>Glu Ala Lys Ala Ala Glu Leu Glu Lys Lys Leu Asp Ser Glu Leu Thr<br>525 530 535 | | | | 1635 |
| GCC CGA CAT GAG CTA CAG GTG GAA ATG AAA AAG ATG GAA AGT GAC TTT<br>Ala Arg His Glu Leu Gln Val Glu Met Lys Lys Met Glu Ser Asp Phe<br>540 545 550 | | | | 1683 |
| GAG CAG AAG CTT CAA GAT CTT CAG GGA GAA AAA GAT GCA CTG CAT TCT<br>Glu Gln Lys Leu Gln Asp Leu Gln Gly Glu Lys Asp Ala Leu His Ser<br>555 560 565 | | | | 1731 |
| GAA AAG CAG CAA ATT GCC ACA GAG AAA CAG GAC CTG GAA GCA GAG GTG<br>Glu Lys Gln Gln Ile Ala Thr Glu Lys Gln Asp Leu Glu Ala Glu Val<br>570 575 580 | | | | 1779 |
| TCC CAG CTC ACA GGA GAG GTT GCC AAG CTG ACA AAG GAA CTG GAA GAT<br>Ser Gln Leu Thr Gly Glu Val Ala Lys Leu Thr Lys Glu Leu Glu Asp<br>585 590 595 600 | | | | 1827 |
| GCC AAG AAA GAA ATG GCT TCC CTC TCT GCG GCA GCT ATT ACT GTA CCT<br>Ala Lys Lys Glu Met Ala Ser Leu Ser Ala Ala Ala Ile Thr Val Pro<br>605 610 615 | | | | 1875 |
| CCT TCT GTT CCT AGT CGT GCT CCT GTT CCC CCT GCC CCT CCT TTA CCT<br>Pro Ser Val Pro Ser Arg Ala Pro Val Pro Pro Ala Pro Pro Leu Pro<br>620 625 630 | | | | 1923 |
| GGT GAC TCT GGC ACT ATT ATT CCA CCA CCA CCT GCT CCT GGG GAT AGT<br>Gly Asp Ser Gly Thr Ile Ile Pro Pro Pro Ala Pro Gly Asp Ser<br>635 640 645 | | | | 1971 |
| ACC ACT CCT CCT CCT CCT CCT CCT CCT CCT CCT CCA CCT CCT TTG<br>Thr Thr Pro Pro Pro Pro Pro Pro Pro Pro Pro Pro Pro Pro Leu<br>650 655 660 | | | | 2019 |
| CCT GGG GGT GTT TGC ATC TCC TCA CCC CCT TCT TTA CCT GGA GGT ACT<br>Pro Gly Gly Val Cys Ile Ser Ser Pro Pro Ser Leu Pro Gly Gly Thr<br>665 670 675 680 | | | | 2067 |
| GCT ATC TCT CCA CCC CCT CCT TTG TCT GGG GAT GCT ACC ATC CCT CCA<br>Ala Ile Ser Pro Pro Pro Leu Ser Gly Asp Ala Thr Ile Pro Pro<br>685 690 695 | | | | 2115 |
| CCC CCT CCT TTG CCT GAG GGT GTT GGC ATC CCT TCA CCC TCT TCT TTG<br>Pro Pro Pro Leu Pro Glu Gly Val Gly Ile Pro Ser Pro Ser Ser Leu<br>700 705 710 | | | | 2163 |
| CCT GGA GGT ACT GCC ATC CCC CCA CCT CCT CCT TTG CCT GGG AGT GCT<br>Pro Gly Gly Thr Ala Ile Pro Pro Pro Pro Leu Pro Gly Ser Ala<br>715 720 725 | | | | 2211 |
| AGA ATC CCC CCA CCA CCA CCT CCT TTG CCT GGG AGT GCT GGA ATT CCC<br>Arg Ile Pro Pro Pro Pro Pro Leu Pro Gly Ser Ala Gly Ile Pro<br>730 735 740 | | | | 2259 |
| CCC CCA CCT CCT CCC TTG CCT GGA GAA GCA GGA ATG CCA CCT CCT CCT | | | | 2307 |

```
Pro Pro Pro Pro Pro Leu Pro Gly Glu Ala Gly Met Pro Pro Pro
745                 750                 755                 760

CCC CCT CTT CCT GGT GGT CCT GGA ATC CCT CCA CCT CCT CCA TTT CCC      2355
Pro Pro Leu Pro Gly Gly Pro Gly Ile Pro Pro Pro Pro Pro Phe Pro
                765                 770                 775

GGA GGC CCT GGC ATT CCT CCA CCT CCA CCC GGA ATG GGT ATG CCT CCA      2403
Gly Gly Pro Gly Ile Pro Pro Pro Pro Pro Gly Met Gly Met Pro Pro
            780                 785                 790

CCT CCC CCA TTT GGA TTT GGA GTT CCT GCA GCC CCA GTT CTG CCA TTT      2451
Pro Pro Pro Phe Gly Phe Gly Val Pro Ala Ala Pro Val Leu Pro Phe
        795                 800                 805

GGA TTA ACC CCC AAA AAG CTT TAT AAG CCA GAG GTG CAG CTC CGG AGG      2499
Gly Leu Thr Pro Lys Lys Leu Tyr Lys Pro Glu Val Gln Leu Arg Arg
    810                 815                 820

CCA AAC TGG TCC AAG CTT GTG GCT GAG GAC CTC TCC CAG GAC TGC TTC      2547
Pro Asn Trp Ser Lys Leu Val Ala Glu Asp Leu Ser Gln Asp Cys Phe
825                 830                 835                 840

TGG ACA AAG GTG AAG GAG GAC CGC TTT GAG AAC AAT GAA CTT TTC GCC      2595
Trp Thr Lys Val Lys Glu Asp Arg Phe Glu Asn Asn Glu Leu Phe Ala
                845                 850                 855

AAA CTT ACC CTT ACC TTC TCT GCC CAG ACC AAG ACT TCC AAA GCC AAG      2643
Lys Leu Thr Leu Thr Phe Ser Ala Gln Thr Lys Thr Ser Lys Ala Lys
            860                 865                 870

AAG GAT CAA GAA GGT GGA GAA GAA AAG AAA TCT GTG CAA AAG AAA AAA      2691
Lys Asp Gln Glu Gly Gly Glu Glu Lys Lys Ser Val Gln Lys Lys Lys
        875                 880                 885

GTA AAA GAG TTA AAG GTG TTG GAT TCA AAG ACA GCC CAG AAT CTC TCA      2739
Val Lys Glu Leu Lys Val Leu Asp Ser Lys Thr Ala Gln Asn Leu Ser
    890                 895                 900

ATC TTT TTG GGT TCC TTC CGC ATG CCC TAT CAA GAG ATT AAG AAT GTC      2787
Ile Phe Leu Gly Ser Phe Arg Met Pro Tyr Gln Glu Ile Lys Asn Val
905                 910                 915                 920

ATC CTG GAG GTG AAT GAG GCT GTT CTG ACT GAG TCT ATG ATC CAG AAC      2835
Ile Leu Glu Val Asn Glu Ala Val Leu Thr Glu Ser Met Ile Gln Asn
                925                 930                 935

CTC ATT AAG CAA ATG CCA GAG CCA GAG CAG TTA AAA ATG CTT TCT GAA      2883
Leu Ile Lys Gln Met Pro Glu Pro Glu Gln Leu Lys Met Leu Ser Glu
            940                 945                 950

CTG AAG GAT GAA TAT GAT GAC CTG GCT GAG TCA GAG CAG TTT GGC GTG      2931
Leu Lys Asp Glu Tyr Asp Asp Leu Ala Glu Ser Glu Gln Phe Gly Val
        955                 960                 965

GTG ATG GGC ACT GTG CCC CGA CTG CGG CCT CGC CTC AAT GCC ATT CTC      2979
Val Met Gly Thr Val Pro Arg Leu Arg Pro Arg Leu Asn Ala Ile Leu
    970                 975                 980

TTC AAG CTA CAA TTC AGC GAG CAA GTG GAG AAT ATC AAG CCA GAG ATT      3027
Phe Lys Leu Gln Phe Ser Glu Gln Val Glu Asn Ile Lys Pro Glu Ile
985                 990                 995                 1000

GTG TCT GTC ACT GCT GCA TGT GAG GAG TTA CGT AAG AGT GAG AGC TTT      3075
Val Ser Val Thr Ala Ala Cys Glu Glu Leu Arg Lys Ser Glu Ser Phe
                1005                1010                1015

TCC AAT CTC CTA GAG ATT ACC TTG CTT GTT GGA AAT TAC ATG AAT GCT      3123
Ser Asn Leu Leu Glu Ile Thr Leu Leu Val Gly Asn Tyr Met Asn Ala
            1020                1025                1030

GGC TCC AGA AAT GCT GGT GCT TTT GGC TTC AAT ATC AGC TTC CTC TGT      3171
Gly Ser Arg Asn Ala Gly Ala Phe Gly Phe Asn Ile Ser Phe Leu Cys
        1035                1040                1045

AAG CTT CGA GAC ACC AAG TCC ACA GAT CAG AAG ATG ACG TTG TTA CAC      3219
Lys Leu Arg Asp Thr Lys Ser Thr Asp Gln Lys Met Thr Leu Leu His
    1050                1055                1060
```

| | |
|---|---|
| TTC TTG GCT GAG TTG TGT GAG AAT GAC TAT CCC GAT GTC CTC AAG TTT<br>Phe Leu Ala Glu Leu Cys Glu Asn Asp Tyr Pro Asp Val Leu Lys Phe<br>1065                      1070                      1075                      1080 | 3267 |
| CCA GAC GAG CTT GCC CAT GTG GAG AAA GCC AGC CGA GTT TCT GCT GAA<br>Pro Asp Glu Leu Ala His Val Glu Lys Ala Ser Arg Val Ser Ala Glu<br>                      1085                      1090                      1095 | 3315 |
| AAC TTG CAA AAG AAC CTA GAT CAG ATG AAG AAA CAA ATT TCT GAT GTG<br>Asn Leu Gln Lys Asn Leu Asp Gln Met Lys Lys Gln Ile Ser Asp Val<br>                1100                      1105                      1110 | 3363 |
| GAA CGT GAT GTT CAG AAT TTC CCA GCT GCC ACA GAT GAA AAA GAC AAG<br>Glu Arg Asp Val Gln Asn Phe Pro Ala Ala Thr Asp Glu Lys Asp Lys<br>1115                      1120                      1125 | 3411 |
| TTT GTT GAA AAA ATG ACC AGC TTT GTG AAG GAT GCA CAG GAA CAG TAT<br>Phe Val Glu Lys Met Thr Ser Phe Val Lys Asp Ala Gln Glu Gln Tyr<br>                1130                      1135                      1140 | 3459 |
| AAC AAG CTG CGG ATG ATG CAT TCT AAC ATG GAG ACC CTC TAT AAG GAG<br>Asn Lys Leu Arg Met Met His Ser Asn Met Glu Thr Leu Tyr Lys Glu<br>1145                      1150                      1155                      1160 | 3507 |
| CTG GGC GAG TAC TTC CTC TTT GAC CCC AAG AAG TTG TCT GTT GAA GAA<br>Leu Gly Glu Tyr Phe Leu Phe Asp Pro Lys Lys Leu Ser Val Glu Glu<br>                      1165                      1170                      1175 | 3555 |
| TTT TTC ATG GAT CTT CAC AAT TTT CGG AAT ATG TTT TTG CAA GCA GTC<br>Phe Phe Met Asp Leu His Asn Phe Arg Asn Met Phe Leu Gln Ala Val<br>                1180                      1185                      1190 | 3603 |
| AAG GAG AAC CAG AAG CGG CGG GAG ACA GAA GAA AAG ATG AGG CGA GCA<br>Lys Glu Asn Gln Lys Arg Arg Glu Thr Glu Glu Lys Met Arg Arg Ala<br>                      1195                      1200                      1205 | 3651 |
| AAA CTA GCC AAG GAG AAG GCA GAG AAG GAG CGG CTA GAG AAG CAG CAG<br>Lys Leu Ala Lys Glu Lys Ala Glu Lys Glu Arg Leu Glu Lys Gln Gln<br>                1210                      1215                      1220 | 3699 |
| AAG AGA GAG CAA CTC ATA GAC ATG AAT GCA GAG GGC GAT GAG ACA GGT<br>Lys Arg Glu Gln Leu Ile Asp Met Asn Ala Glu Gly Asp Glu Thr Gly<br>1225                      1230                      1235                      1240 | 3747 |
| GTG ATG GAC AGT CTT CTA GAA GCC CTG CAG TCA GGG GCA GCA TTC CGA<br>Val Met Asp Ser Leu Leu Glu Ala Leu Gln Ser Gly Ala Ala Phe Arg<br>                1245                      1250                      1255 | 3795 |
| CGG AAG AGA GGG CCC CGT CAA GCC AAC AGG AAG GCC GGG TGT GCA GTC<br>Arg Lys Arg Gly Pro Arg Gln Ala Asn Arg Lys Ala Gly Cys Ala Val<br>                      1260                      1265                      1270 | 3843 |
| ACA TCT CTG CTA GCT TCG GAG CTG ACC AAG GAT GAT GCC ATG GCT GCT<br>Thr Ser Leu Leu Ala Ser Glu Leu Thr Lys Asp Asp Ala Met Ala Ala<br>                1275                      1280                      1285 | 3891 |
| GTT CCT GCC AAG GTG TCC AAG AAC AGT GAG ACA TTC CCC ACA ATC CTT<br>Val Pro Ala Lys Val Ser Lys Asn Ser Glu Thr Phe Pro Thr Ile Leu<br>                      1290                      1295                      1300 | 3939 |
| GAG GAA GCC AAG GAG TTG GTT GGC CGT GCA AGC TAATGTGGGT CCTGTGACCG<br>Glu Glu Ala Lys Glu Leu Val Gly Arg Ala Ser<br>1305                      1310                      1315 | 3992 |
| CGGCAGCTCC TCAGCGGAGC CGCAGACTGT CCTGCCCTGC AGCATGTGCC TAAAGGCTCA | 4052 |
| AGGGGATATT CCTCTGGGGT GGCCACTCCC ACCACCCTGA CCCTGTCTTT CTCTCTGGCC | 4112 |
| TGCTGCTCTC TCAACATCAC ATACAGCTTC AGCTGCCTGG AGGCCAGAAG GAAAGGGCAG | 4172 |
| TGCAGGGGAG GCCTGAGCCC GACTTAGCCA GCCCTGGCTG TTGTATTACC AAAGCAGGGT | 4232 |
| CCATGTTTGC TGCCTTAACC CTGTCTCCTC TCTGTTACTC AGAGGGCCTC ATCTCAGACA | 4292 |
| AGGCCCAGCC TGCTTTTTCT CAGCCCTGAC TTTCTAATGG GCTTTCCCCC CTAGGTCAGT | 4352 |
| CTTGCTGGAT TTGTGCTTTT CTTTTGTGGT TTCTCTGGCC CTGAGAATAG CATGGGGCTT | 4412 |
| GTAAACCTTT GGGCTAGATC CCTCCTTTCA TTGCTGTTGT CTCTGCTCTT CCCTCTCCTG | 4472 |

-continued

```
GCTGTGGTTA TTTATTATTA GTGGTGTGGC ACTGGGAGCT GCTCCTAAGG AAGCAGGGAG      4532

CAAATCCCAC CTTTACCCCA CCTTCCTGGG AAAGGCCTCC AAAGCAAAGG ATCTGGACCA      4592

GTTTCCCTGC TGTGCTGTGG CCCAGGCCAG AGCCTGTGGG CAGGCAGGCA GGGCATAGCG      4652

ACAGTGTGGG ACCTGCCCCC AGCTTCTGCC ACGCTTTATG CCCTTGCCTC TCTGGACGCT      4712

CTGCACCAAC CCCAGGCTAC TGAGCCACCT TCCCTCCTCA TGCCTTCCCT GAGCTTTGGT      4772

GCATCTCATC TGGACTATGG GTTGTACTGT GACCATCCCA ACACCTCACC CTCTGTCTAC      4832

AAGGAAATGG GAGGTGGAGC CTCCTGGCTG AGAAATTGTT TTGCAAATGG ATCTATTTTT      4892

GTATGAAAAA AAAAATTTTT TTAAAGAAAA CTGTTCCTTC CCCCTTTCCC CTCCATAATG      4952

TAAGAAGCTT TGGTGGCAGG TTACAGAGTT CTGGGATTTC TTCTCACAGG CCCAATCCTG      5012

AATGTGCCCC TGGACCTTCT GGACCCTTGA GTCCAAGGCA GATCCTCTCT CCCAGGGAAT      5072

CCGACACAGG AGGAACCCCT TCTCTGGTTG AGCTGGGCCA GGCCTAAGAG TAGCAGGAAC      5132

TCTAAGACCA CAGAGTTTTT TATAAATGTA TAAATGTATC AAGCCAAATG TGCAGATGCT      5192

AACTGGACAT TCTGGGGAAC TGGGCACCAG GAGTGCCTTC ATACACTGTA CCCCAGCTCT      5252

CTTCTAAAAG AGAAGTGGGT GGGCACACTG AACTGTTTGG TGGCCCCAAC CACAGGAAGC      5312

TGCAATTCTC TGGCTTAGGG TGATACTTTT GCCCTCCTTG TGCCCCTCTC AGCTTTCCAT      5372

CCCCAGCTAG GAAGAAAGAA TGGCACTCTT GGGCTTGGCC CAGAATTAGA GTTATTAGAG      5432

CAAGAGAGAG CTTAGGAAGC ATGAGGGCAA CTATAGTGAG GCCTTATTGC CAGGAGGGAG      5492

GGTTTTGGTT GCTGGCGCTT GTGTATAAAG GGGCAAGAGC AGCTCCTTTG GACTATTCCT      5552

GGGAGGACTC TGATGCAGGG CGTCTGTTGC TCCCCTGGGT CACCTCCTCC CTGCTCGCTG      5612

ACATCTGGGG CTTTGACCCT TTCTTTTTTA ATCTACTTTT GCTAAGATGC ATTTAATAAA      5672

AAAAAAGAGA GAGAGAGAGA GGTGTGAGGG ACAAAATGCA AACCTATTTC CCTTGCCTCA      5732

TAGGCTTCTG GGATGTCATC ACCTCCAGTT TGTTGGTTTT GTTTCCAACT GTTAATAAAG      5792

CATTGAAACA GTAAAAAAAA AAAAAAAAA                                       5822

(2) INFORMATION FOR SEQ ID NO:5:

(i) SEQUENCE CHARACTERISTICS:
        (A) LENGTH: 5822 base pairs
        (B) TYPE: nucleic acid
        (C) STRANDEDNESS: single
        (D) TOPOLOGY: linear (ii) MOLECULE TYPE: cDNA to mRNA (iv) ANTI-SENSE: YES (vi) ORIGINAL SOURCE:
        (A) ORGANISM: Human (xi) SEQUENCE DESCRIPTION: SEQ ID NO:5:

TTTTTTTTTT TTTTTTTTAC TGTTTCAATG CTTTATTAAC AGTTGGAAAC AAAACCAACA        60

AACTGGAGGT GATGACATCC CAGAAGCCTA TGAGGCAAGG GAAATAGGTT TGCATTTTGT       120

CCCTCACACC TCTCTCTCTC TCTCTTTTTT TTTATTAAAT GCATCTTAGC AAAAGTAGAT       180

TAAAAAGAA AGGGTCAAAG CCCCAGATGT CAGCGAGCAG GGAGGAGGTG ACCCAGGGGA        240

GCAACAGACG CCCTGCATCA GAGTCCTCCC AGGAATAGTC CAAAGGAGCT GCTCTTGCCC       300

CTTTATACAC AAGCGCCAGC AACCAAAACC CTCCCTCCTG GCAATAAGGC CTCACTATAG       360

TTGCCCTCAT GCTTCCTAAG CTCTCTCTTG CTCTAATAAC TCTAATTCTG GGCCAAGCCC       420
```

-continued

```
AAGAGTGCCA TTCTTTCTTC CTAGCTGGGG ATGGAAAGCT GAGAGGGGCA CAAGGAGGGC      480

AAAAGTATCA CCCTAAGCCA GAGAATTGCA GCTTCCTGTG GTTGGGGCCA CCAAACAGTT      540

CAGTGTGCCC ACCCACTTCT CTTTTAGAAG AGAGCTGGGG TACAGTGTAT GAAGGCACTC      600

CTGGTGCCCA GTTCCCCAGA ATGTCCAGTT AGCATCTGCA CATTTGGCTT GATACATTTA      660

TACATTTATA AAAAACTCTG TGGTCTTAGA GTTCCTGCTA CTCTTAGGCC TGGCCCAGCT      720

CAACCAGAGA AGGGGTTCCT CCTGTGTCGG ATTCCCTGGG AGAGAGGATC TGCCTTGGAC      780

TCAAGGGTCC AGAAGGTCCA GGGGCACATT CAGGATTGGG CCTGTGAGAA GAAATCCCAG      840

AACTCTGTAA CCTGCCACCA AAGCTTCTTA CATTATGGAG GGGAAGGGG GAAGGAACAG       900

TTTTCTTTAA AAAAATTTTT TTTTTCATAC AAAAATAGAT CCATTTGCAA AACAATTTCT      960

CAGCCAGGAG GCTCCACCTC CCATTTCCTT GTAGACAGAG GGTGAGGTGT TGGGATGGTC     1020

ACAGTACAAC CCATAGTCCA GATGAGATGC ACCAAAGCTC AGGGAAGGCA TGAGGAGGGA     1080

AGGTGGCTCA GTAGCCTGGG GTTGGTGCAG AGCGTCCAGA GAGGCAAGGG CATAAAGCGT     1140

GGCAGAAGCT GGGGGCAGGT CCCACACTGT CGCTATGCCC TGCCTGCCTG CCCACAGGCT     1200

CTGGCCTGGG CCACAGCACA GCAGGGAAAC TGGTCCAGAT CCTTTGCTTT GGAGGCCTTT     1260

CCCAGGAAGG TGGGGTAAAG GTGGGATTTG CTCCCTGCTT CCTTAGGAGC AGCTCCCAGT     1320

GCCACACCAC TAATAATAAA TAACCACAGC CAGGAGAGGG AAGAGCAGAG ACAACAGCAA     1380

TGAAAGGAGG GATCTAGCCC AAAGGTTTAC AAGCCCCATG CTATTCTCAG GCCAGAGAA      1440

ACCACAAAAG AAAAGCACAA ATCCAGCAAG ACTGACCTAG GGGGGAAAGC CCATTAGAAA     1500

GTCAGGGCTG AGAAAAAGCA GGCTGGGCCT TGTCTGAGAT GAGGCCCTCT GAGTAACAGA     1560

GAGGAGACAG GGTTAAGGCA GCAAACATGG ACCCTGCTTT GGTAATACAA CAGCCAGGGC     1620

TGGCTAAGTC GGGCTCAGGC CTCCCCTGCA CTGCCCTTTC CTTCTGGCCT CCAGGCAGCT     1680

GAAGCTGTAT GTGATGTTGA GAGAGCAGCA GGCCAGAGAG AAAGACAGGG TCAGGGTGGT     1740

GGGAGTGGCC ACCCCAGAGG AATATCCCCT TGAGCCTTTA GGCACATGCT GCAGGGCAGG     1800

ACAGTCTGCG GCTCCGCTGA GGAGCTGCCG CGGTCACAGG ACCCACATTA GCTTGCACGG     1860

CCAACCAACT CCTTGGCTTC CTCAAGGATT GTGGGGAATG TCTCACTGTT CTTGGACACC     1920

TTGGCAGGAA CAGCAGCCAT GGCATCATCC TTGGTCAGCT CCGAAGCTAG CAGAGATGTG     1980

ACTGCACACC CGGCCTTCCT GTTGGCTTGA CGGGGCCCTC TCTTCCGTCG GAATGCTGCC     2040

CCTGACTGCA GGGCTTCTAG AAGACTGTCC ATCACACCTG TCTCATCGCC CTCTGCATTC     2100

ATGTCTATGA GTTGCTCTCT CTTCTGCTGC TTCTCTAGCC GCTCCTTCTC TGCCTTCTCC     2160

TTGGCTAGTT TTGCTCGCCT CATCTTTTCT TCTGTCTCCC GCCGCTTCTG GTTCTCCTTG     2220

ACTGCTTGCA AAAACATATT CCGAAAATTG TGAAGATCCA TGAAAAATTC TTCAACAGAC     2280

AACTTCTTGG GGTCAAAGAG GAAGTACTCG CCCAGCTCCT TATAGAGGGT CTCCATGTTA     2340

GAATGCATCA TCCGCAGCTT GTTATACTGT TCCTGTGCAT CCTTCACAAA GCTGGTCATT     2400

TTTTCAACAA ACTTGTCTTT TTCATCTGTG GCAGCTGGGA AATTCTGAAC ATCACGTTCC     2460

ACATCAGAAA TTTGTTTCTT CATCTGATCT AGGTTCTTTT GCAAGTTTTC AGCAGAAACT     2520

CGGCTGGCTT TCTCCACATG GGCAAGCTCG TCTGGAAACT TGAGGACATC GGGATAGTCA     2580

TTCTCACACA ACTCAGCCAA GAAGTGTAAC AACGTCATCT TCTGATCTGT GGACTTGGTG     2640

TCTCGAAGCT TACAGAGGAA GCTGATATTG AAGCCAAAAG CACCAGCATT TCTGGAGCCA     2700

GCATTCATGT AATTTCCAAC AAGCAAGGTA ATCTCTAGGA GATTGGAAAA GCTCTCACTC     2760

TTACGTAACT CCTCACATGC AGCAGTGACA GACACAATCT CTGGCTTGAT ATTCTCCACT     2820
```

```
TGCTCGCTGA ATTGTAGCTT GAAGAGAATG GCATTGAGGC GAGGCCGCAG TCGGGGCACA    2880

GTGCCCATCA CCACGCCAAA CTGCTCTGAC TCAGCCAGGT CATCATATTC ATCCTTCAGT    2940

TCAGAAAGCA TTTTTAACTG CTCTGGCTCT GGCATTTGCT TAATGAGGTT CTGGATCATA    3000

GACTCAGTCA GAACAGCCTC ATTCACCTCC AGGATGACAT TCTTAATCTC TTGATAGGGC    3060

ATGCGGAAGG AACCCAAAAA GATTGAGAGA TTCTGGGCTG TCTTTGAATC CAACACCTTT    3120

AACTCTTTTA CTTTTTTCTT TTGCACAGAT TTCTTTTCTT CTCCACCTTC TTGATCCTTC    3180

TTGGCTTTGG AAGTCTTGGT CTGGGCAGAG AAGGTAAGGG TAAGTTTGGC GAAAAGTTCA    3240

TTGTTCTCAA AGCGGTCCTC CTTCACCTTT GTCCAGAAGC AGTCCTGGGA GAGGTCCTCA    3300

GCCACAAGCT TGGACCAGTT TGGCCTCCGG AGCTGCACCT CTGGCTTATA AGCTTTTTG     3360

GGGGTTAATC CAAATGGCAG AACTGGGCT GCAGGAACTC CAAATCCAAA TGGGGAGGT      3420

GGAGGCATAC CCATTCCGGG TGGAGGTGGA GGAATGCCAG GGCCTCCGGG AAATGGAGGA    3480

GGTGGAGGGA TTCCAGGACC ACCAGGAAGA GGGGGAGGAG GAGGTGGCAT TCCTGCTTCT    3540

CCAGGCAAGG GAGGAGGTGG GGGGGGAATT CCAGCACTCC CAGGCAAAGG AGGTGGTGGT    3600

GGGGGGATTC TAGCACTCCC AGGCAAAGGA GGAGGTGGGG GGATGGCAGT ACCTCCAGGC    3660

AAAGAAGAGG GTGAAGGGAT GCCAACACCC TCAGGCAAAG GAGGGGGTGG AGGGATGGTA    3720

GCATCCCCAG ACAAAGGAGG GGGTGGAGAG ATAGCAGTAC CTCCAGGTAA AGAAGGGGGT    3780

GAGGAGATGC AAACACCCCC AGGCAAAGGA GGTGGAGGAG GAGGAGGAGG AGGAGGAGGA    3840

GGAGGAGTGG TACTATCCCC AGGAGCAGGT GGTGGTGGAA TAATAGTGCC AGAGTCACCA    3900

GGTAAAGGAG GGGCAGGGGG AACAGGAGCA CGACTAGGAA CAGAAGGAGG TACAGTAATA    3960

GCTGCCGCAG AGAGGGAAGC CATTTCTTTC TTGGCATCTT CCAGTTCCTT TGTCAGCTTG    4020

GCAACCTCTC CTGTGAGCTG GGACACCTCT GCTTCCAGGT CCTGTTTCTC TGTGGCAATT    4080

TGCTGCTTTT CAGAATGCAG TGCATCTTTT TCTCCCTGAA GATCTTGAAG CTTCTGCTCA    4140

AAGTCACTTT CCATCTTTTT CATTTCCACC TGTAGCTCAT GTCGGGCTGT TAACTCTGAG    4200

TCCAACTTCT TTTCCAGCTC TGCAGCTTTG GCTTCAGATT TCTCCACCTT TGTCTTATCA    4260

ATCATTTGAT CAATTAATCC CTCAATCTCA ATCTGGAGGT GCCGGCACTT GAAGTCAGGA    4320

TCAGCCCCGT TCTTGTGCAG AACTATCTGG GAAATACATT CTTCAATCAA CTTATAGTAC    4380

TGAGGTCTGG CCTCATAGTC ATTTCGGACC AAGAGTAAGT GCTGCAGGAT GGAAAGGAAG    4440

TGTGGCTCTG CCTTTGAATC CTTCACTGTG TTTAAGAGAA TCTGAAAGAC TTCATTAAAG    4500

TCATCCATCT CCATGCGAAT GTCATCCAGC CGTCCCTTCA GGTCATAGGA ATCCTCTTCC    4560

CCTTGTTCAT CAAACACATT TAGTTGCACT CTCATATCTT CATTTTCAAT CTCTCGAAGG    4620

TCCTGCAACA CCTGATGTAG CCCCAAACGC ATCAGTTCAC TTCTGATGTG AACTCGGAAG    4680

TCAAGTTCCT CCGCTGGTGT GATGAGAGCA TTGATCAGCT GTAGGCATCC AACCTTCAGT    4740

GCAATAGTGG TTCCACTTTT TAATCCATCC AGCAGCGGCT GGAAACGTTC CACTTCATCC    4800

ATCTCAGCTC TTTCTGTCAT TGCCTCCAAA ACCCTTTCAT TCATGTCCTC TGGCTGCGGT    4860

AGAATACAAA GAGCAGAAAG CAGCTTAGCT GCATCAATCA TCATGTTGGG AACAGCAGGA    4920

TCCATGGCTC TGACCAGCAG TAGGATTCCT TCTTCTGTCT CCAACATGGT CTTGATTCCA    4980

AACTTGTTGT TCATAAAAGC TTTCAAGCAG CGAATGATCT CATGCTTGTT CCGGCTATCG    5040

TAACTCCCAG CAGTCTCTTC TTTCTCATCA TGAAGTCGTT TAAGAATGTC CAATAAGGAG    5100

GCCAAGCCTT CAGCACCAAA TGTTTGCACC CAACTGACAG GGTTGTTGTT GAGAGACACA    5160
```

-continued

| | |
|---|---|
| CGAAGGGACT CCAGGCAGCT GAGCAGAGGC ATATCCCGCA AGCCTGACCT CAACTCCTGA | 5220 |
| ATATACATCA TGGCAGACTT AGAGCTCTCC TTCTGGCTCA TGCCAGCCTT GGAGGTGTAC | 5280 |
| AAGTATTGGG ACACCATCTC CCTCTTGATG ATGATGTCCT TCTCCCTCAA AGGTTGCTGT | 5340 |
| TTCTCCTCAT TCAGGTTCAT ATCCAGCAGC ATCTGTTCAA AGAGAACCAG CACTTGTTCA | 5400 |
| TCTGAAACAT CTTGCAATGA CTGTGCTGTG GGATCATCCC CATATGATGC AGAAGAATTT | 5460 |
| CTATGAGCAG AATTGGGCTT TTCCTTCTCC TTCTTAATTC TCATGCTGGT AAATCTCTCC | 5520 |
| AGAAATTTCT TAGATTTGCC GCCGTCGCCG CCCGCCGAGG GCAGCTCATC TGGGCTCCGG | 5580 |
| CCCTTCTTCT TGTCCCGGGT CCCGCGGCCG GGCCCAGGC TCCCGCCGGG CGGCTCCATG | 5640 |
| TCCCGGTTCA CGCTGGCCGG CGACCCCGCG CCTACGCCGC CCGGAATTCC GGGCCCCCTC | 5700 |
| CTCCCCTTTC CTGCTTCTGC GAGAACTCCC TCCCTCCCTC CAGCTCCGCC AGCCCAGGCG | 5760 |
| CCCCTTCCCT GGAAGCCGAG CGGCTTCGCT CGCATTTCAC CGCCGCCGCC TCTCGCAATA | 5820 |
| TT | 5822 |

(2) INFORMATION FOR SEQ ID NO:6:

(i) SEQUENCE CHARACTERISTICS:
        (A) LENGTH: 755 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Human (xi) SEQUENCE DESCRIPTION: SEQ ID NO:6:

| | |
|---|---|
| ATATGAGAGT GCAACTAAAT GTGTTTGATG AACAAGGGGA AGAGGATTCC TATGACCTGA | 60 |
| AGGGACGGCT GGATGACATT CGCATGGAGA TGGAATATCC TTTTGCTGAC TAGGTTCAAG | 120 |
| GCAGATGAGA CATTCATTGT ATTTAGTTCC CTGATCCCTG TGTGGAATGG TTTGGGAGAT | 180 |
| GATGACTCAG AACAGAGCAT CAGGCTTATG TGTCTTCTCA TTAAATAAGG CAGGTGTATT | 240 |
| TTTATTGCGC TGGCTTTACT TAGCTTATCA TAGATCAGGG AAGTCAGTAA AGGTGATCTG | 300 |
| AGGGTTGTTG AGCATGGAAG CCATCAAAAT CAGTGTAAAC TTCCTAGAAT GTGATAGCTT | 360 |
| AGCTTACTAA GATGTAGAAC TGGCTTTTAG AGATGTTTGG ACTGACAGAG GGAGTAATTT | 420 |
| AGTTACCTGT TAATATTTTC AGTAAGTGAC TTTGAGGCAG TTACCTCTTA TTTTCTGTCT | 480 |
| ACTGCCTGAT CTTCAAGCCA AGTACTTACT AGGAATCCTC TGTGTGTATA GTACCACCCA | 540 |
| ATTCACTGGT CCCTTAAAGG ACGTTTTAGA AAGCTTAAAG TTTCTGGTGA TGTTTACAGG | 600 |
| AAGAACAGCC AGTAGAATGG AAGTGGTGTC TTGCTACTTT TCCCTAGCTT TTTCAAGAGT | 660 |
| TAAATAAGCC ACCTGTCAAA CATAATTTCT GCATATTTGC TTTCCTTAGC CTATTTCCCT | 720 |
| TTTCCACTGA CTTTAATGAA GTCTTTCAGA TTCTC | 755 |

(2) INFORMATION FOR SEQ ID NO:7:

(i) SEQUENCE CHARACTERISTICS:
        (A) LENGTH: 755 base pairs
        (B) TYPE: nucleic acid
        (C) STRANDEDNESS: single
        (D) TOPOLOGY: linear (ii) MOLECULE TYPE: DNA (genomic)

(iv) ANTI-SENSE: YES (vi) ORIGINAL SOURCE:
    (A) ORGANISM: Human (xi) SEQUENCE DESCRIPTION: SEQ ID NO:7:

| | | | | | |
|---|---|---|---|---|---|
| GAGAATCTGA | AAGACTTCAT | TAAAGTCAGT | GGAAAAGGGA | AATAGGCTAA | GGAAAGCAAA | 60 |
| TATGCAGAAA | TTATGTTTGA | CAGGTGGCTT | ATTTAACTCT | TGAAAAAGCT | AGGGAAAAGT | 120 |
| AGCAAGACAC | CACTTCCATT | CTACTGGCTG | TTCTTCCTGT | AAACATCACC | AGAAACTTTA | 180 |
| AGCTTTCTAA | AACGTCCTTT | AAGGGACCAG | TGAATTGGGT | GGTACTATAC | ACACAGAGGA | 240 |
| TTCCTAGTAA | GTACTTGGCT | TGAAGATCAG | GCAGTAGACA | GAAAATAAGA | GGTAACTGCC | 300 |
| TCAAAGTCAC | TTACTGAAAA | TATTAACAGG | TAACTAAATT | ACTCCCTCTG | TCAGTCCAAA | 360 |
| CATCTCTAAA | AGCCAGTTCT | ACATCTTAGT | AAGCTAAGCT | ATCACATTCT | AGGAAGTTTA | 420 |
| CACTGATTTT | GATGGCTTCC | ATGCTCAACA | ACCCTCAGAT | CACCTTTACT | GACTTCCCTG | 480 |
| ATCTATGATA | AGCTAAGTAA | AGCCAGCGCA | ATAAAAATAC | ACCTGCCTTA | TTTAATGAGA | 540 |
| AGACACATAA | GCCTGATGCT | CTGTTCTGAG | TCATCATCTC | CCAAACCATT | CCACACAGGG | 600 |
| ATCAGGGAAC | TAAATACAAT | GAATGTCTCA | TCTGCCTTGA | ACCTAGTCAG | CAAAAGGATA | 660 |
| TTCCATCTCC | ATGCGAATGT | CATCCAGCCG | TCCCTTCAGG | TCATAGGAAT | CCTCTTCCCC | 720 |
| TTGTTCATCA | AACACATTTA | GTTGCACTCT | CATAT | | | 755 |

(2) INFORMATION FOR SEQ ID NO:8:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 10
        (D) OTHER INFORMATION: /product= "G/S/A/V"

(xi) SEQUENCE DESCRIPTION: SEQ ID NO:8:

Ile Pro Pro Pro Pro Pro Leu Pro Gly Xaa
1               5                   10

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

TGGAGGTACA GGTATACCAC CACCACCTCC                                    30

(2) INFORMATION FOR SEQ ID NO:10:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

GTTCTCACTC TTACGCAGCT CTTCGCATGC                                    30

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:11:

CCGTCCCTTC AGGTCATAGG                                               20

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

CAGGAAACAG CTATGACCAT G                                             21

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

ATATGAGAGT GCAACTAAA                                                19

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

GAGAATCTGA AAGACTTCAT T                                             21